United States Patent
Pham et al.

(10) Patent No.: US 8,658,364 B2
(45) Date of Patent: Feb. 25, 2014

(54) ISOLATION OF POLYMERASE-NUCLEIC ACID COMPLEXES

(75) Inventors: Thang Pham, Mountain View, CA (US); Arunashree Bhamidipati, Palo Alto, CA (US); Kevin Travers, Menlo Park, CA (US); Eric Olivares, Union City, CA (US); Tyson A. Clark, Menlo Park, CA (US); Jonas Korlach, Newark, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 13/427,725

(22) Filed: Mar. 22, 2012

(65) Prior Publication Data

US 2012/0322666 A1     Dec. 20, 2012

Related U.S. Application Data

(60) Provisional application No. 61/466,747, filed on Mar. 23, 2011, provisional application No. 61/531,530, filed on Sep. 6, 2011.

(51) Int. Cl.
*C12Q 1/68*       (2006.01)
*C40B 30/04*     (2006.01)

(52) U.S. Cl.
USPC .............................. 435/6.11; 506/9

(58) Field of Classification Search
USPC ........................... 435/6.1; 506/2, 9
See application file for complete search history.

(56) References Cited

U.S. PATENT DOCUMENTS

| | | | |
|---|---|---|---|
| 5,001,050 A | 3/1991 | Blanco et al. | |
| 5,143,854 A | 9/1992 | Pirrung et al. | |
| 5,198,543 A | 3/1993 | Blanco et al. | |
| 5,424,186 A | 6/1995 | Fodor et al. | |
| 5,547,839 A | 8/1996 | Dower et al. | |
| 5,576,204 A | 11/1996 | Blanco et al. | |
| 5,624,711 A | 4/1997 | Sundberg et al. | |
| 5,648,245 A | 7/1997 | Fire et al. | |
| 5,674,716 A | 10/1997 | Tabor et al. | |

(Continued)

FOREIGN PATENT DOCUMENTS

| | | |
|---|---|---|
| WO | 9106678 A1 | 5/1991 |
| WO | 9627025 A1 | 9/1996 |
| WO | 9905315 A2 | 2/1999 |
| WO | 2011031313 A2 | 3/2011 |

OTHER PUBLICATIONS

Eid, J. et al. "Real-time DNA Sequencing from Single Polymerase Molecules" Science (2009) 323:133-138.

(Continued)

*Primary Examiner* — Samuel Woolwine
*Assistant Examiner* — Kaijiang Zhang
(74) *Attorney, Agent, or Firm* — Robert H. Reamey

(57) ABSTRACT

Compositions, methods and systems are provided for the isolation of polymerase-nucleic acid complexes. Complexes can be separated from free enzyme by using hook molecules to target single stranded regions on the nucleic acid. Active complexes can be isolated from mixtures having both active and inactive complexes by initiating nucleic acid synthesis so as to open up a portion of a double stranded region rendering that region single stranded. Hook molecules are targeted to bind the sequences that are thus exposed. The hook molecules bound to active polymerase-nucleic acid complex are isolated, and the active polymerase-nucleic acid complexes released.

19 Claims, 23 Drawing Sheets

(56) References Cited

U.S. PATENT DOCUMENTS

| | | | |
|---|---|---|---|
| 5,714,320 | A | 2/1998 | Kool |
| 5,919,523 | A | 7/1999 | Sundberg et al. |
| 6,210,896 | B1 | 4/2001 | Chan |
| 6,255,083 | B1 | 7/2001 | Williams |
| 6,261,808 | B1 | 7/2001 | Auerbach |
| 6,787,308 | B2 | 9/2004 | Balasubramanian et al. |
| 6,917,726 | B2 | 7/2005 | Levene et al. |
| 7,013,054 | B2 | 3/2006 | Levene et al. |
| 7,056,661 | B2 | 6/2006 | Korlach et al. |
| 7,170,050 | B2 | 1/2007 | Turner et al. |
| 7,476,503 | B2 | 1/2009 | Turner et al. |
| 7,486,865 | B2 | 2/2009 | Foquet et al. |
| 7,763,423 | B2 | 7/2010 | Roitman et al. |
| 7,901,889 | B2 | 3/2011 | Christians et al. |
| 7,906,284 | B2 | 3/2011 | Turner et al. |
| 7,907,800 | B2 | 3/2011 | Foquet et al. |
| 7,931,867 | B2 | 4/2011 | Korlach |
| 7,932,035 | B2 | 4/2011 | Korlach |
| 7,935,310 | B2 | 5/2011 | Korlach |
| 7,993,891 | B2 | 8/2011 | Roitman et al. |
| 8,003,330 | B2 | 8/2011 | Henier et al. |
| 8,137,942 | B2 | 3/2012 | Roitman et al. |
| 8,153,375 | B2 | 4/2012 | Travers et al. |
| 8,193,123 | B2 | 6/2012 | Rank et al. |
| 2003/0096253 | A1 | 5/2003 | Nelson et al. |
| 2003/0190647 | A1 | 10/2003 | Odera |
| 2003/0215862 | A1 | 11/2003 | Parce et al. |
| 2004/0048300 | A1 | 3/2004 | Sood et al. |
| 2004/0152119 | A1 | 8/2004 | Sood et al. |
| 2004/0224319 | A1 | 11/2004 | Sood et al. |
| 2004/0259082 | A1 | 12/2004 | Williams |
| 2008/0108082 | A1 | 5/2008 | Rank et al. |
| 2009/0118129 | A1 | 5/2009 | Turner |
| 2009/0186349 | A1* | 7/2009 | Gunderson et al. ............ 435/6 |
| 2010/0009872 | A1 | 1/2010 | Eid et al. |
| 2010/0093555 | A1 | 4/2010 | Bjornson et al. |
| 2010/0099100 | A1 | 4/2010 | Zaccarin et al. |
| 2010/0112645 | A1 | 5/2010 | Clark et al. |
| 2011/0059505 | A1 | 3/2011 | Hanzel et al. |
| 2011/0117637 | A1 | 5/2011 | Gray et al. |
| 2011/0183409 | A1 | 7/2011 | Newby et al. |
| 2011/0189659 | A1 | 8/2011 | Clark et al. |
| 2011/0222179 | A1 | 9/2011 | Monadgemi |
| 2011/0256618 | A1 | 10/2011 | Eid et al. |
| 2011/0257040 | A1 | 10/2011 | Turner et al. |
| 2012/0034602 | A1 | 2/2012 | Emig et al. |
| 2012/0071359 | A1 | 3/2012 | Sun et al. |
| 2012/0115736 | A1 | 5/2012 | Bjornson et al. |
| 2012/0196279 | A1 | 8/2012 | Underwood et al. |

OTHER PUBLICATIONS

Hong at al., "Self-Assembly of a Dendron through Multiple Ionic Interaction to Give. Mesospacing between Reactive Amine Groups on the Surface". (2003) Langmuir 19:2357-2365.

Levene, M.J. et al "Zero-mode waveguides for single-molecule analysis at high concentrations" Science (2003) 299:682-686.

U.S. Appl. No. 61/593,569, filed Feb. 1, 2011, Kamtekar et al.

U.S. Appl. No. 13/182,433, filed Jun. 16, 2011, Bayandorian et al.

U.S. Appl. No. 13/429,019, filed Mar. 23, 2012, Pham et al.

International Search Report and Written Opinion dated Oct. 30, 2012 for related PCT/US2012/029830.

International Preliminary Report on Patentability dated Oct. 3, 2013 for related PCT/US2012/029830.

Choi et al., "An On-Chip Magnetic Bead Separator Using Spiral Electromagnetics with Semi-Encapsulated Permalloy," Biosens. Bioelectron (2001) 16;409-416.

Harris et al., "Single-Molecule DNA Sequencing of a Viral Genomic," Science (2008) 320:106-109.

Shikida et al., "Using Wettability and Interfacial Tension to Handle Droplets of Magnetic Beads in a Micro-Chemicai-Analysis System," Sens. Actuators B Chem. (2006) 113:563-569.

* cited by examiner

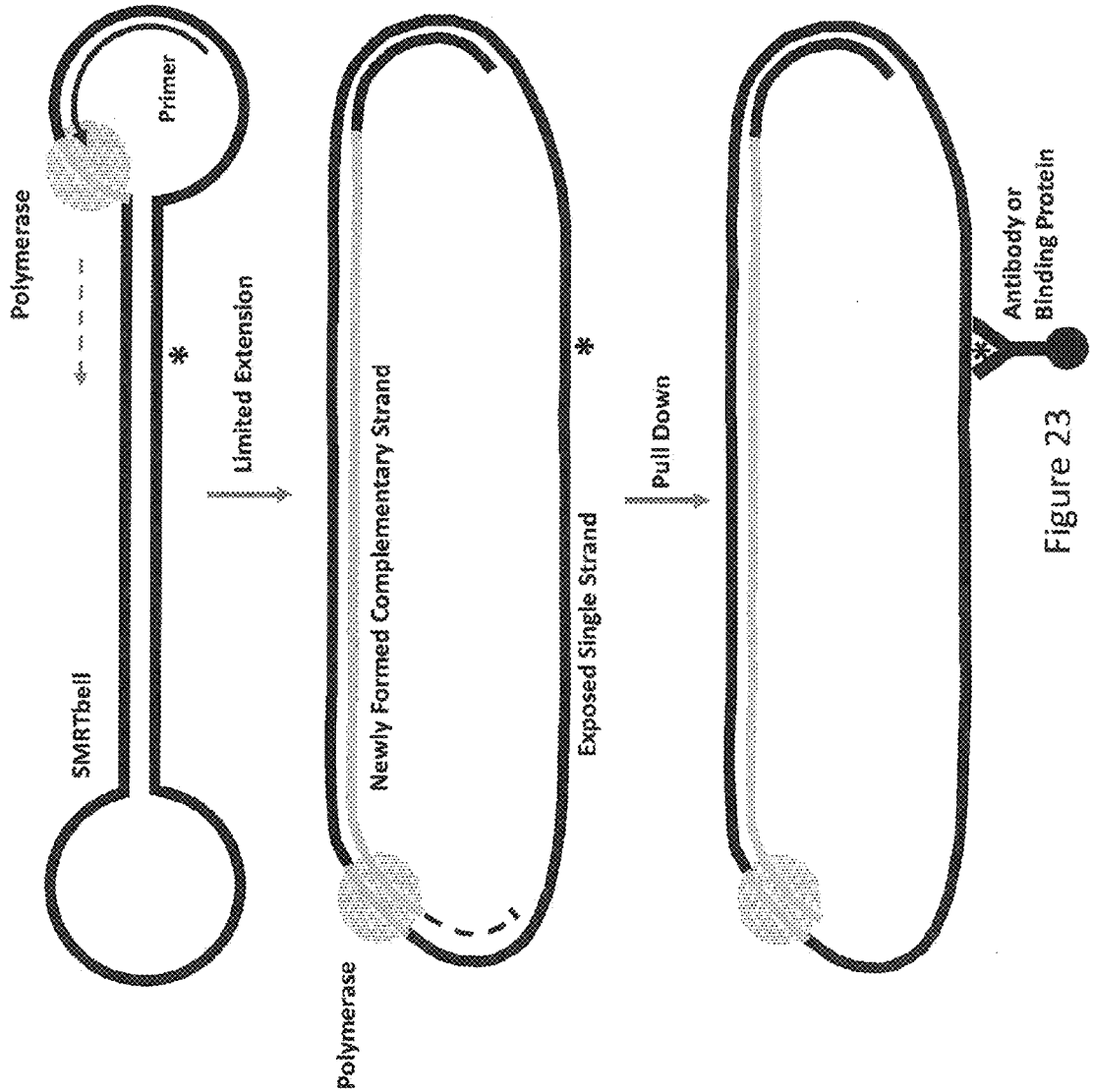

ISOLATION OF POLYMERASE-NUCLEIC ACID COMPLEXES

CROSS-REFERENCE TO RELATED APPLICATIONS

This application claims the benefit of priority to Provisional Application No. 61/466,747, filed Mar. 23, 2011, and Provisional Application No. 61/531,530, filed Sep. 6, 2011, the full disclosures of which are incorporated herein by reference in their entirety for all purposes.

STATEMENT REGARDING FEDERALLY SPONSORED RESEARCH

Not Applicable.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only one 3 KB file (01013003_2012-08-23_SequenceListingUpdated.txt).

BACKGROUND OF THE INVENTION

The ability to read the genetic code has opened countless opportunities to benefit humankind. Whether it involves the improvement of food crops and livestock used for food, the identification of the causes of disease, the generation of targeted therapeutic methods and compositions, or simply the better understanding of what makes us who we are, a fundamental understanding of the blueprints of life is an integral and necessary component.

A variety of techniques and processes have been developed to obtain genetic information, including broad genetic profiling or identifying patterns of discrete markers in genetic codes and nucleotide level sequencing of entire genomes. With respect to determination of genetic sequences, while techniques have been developed to read, at the nucleotide level, a genetic sequence, such methods can be time-consuming and extremely costly.

Approaches have been developed to sequence genetic material with improved speed and reduced costs. Many of these methods rely upon the identification of nucleotides being incorporated by a polymerization enzyme during a template sequence-dependent nucleic acid synthesis reaction. In particular, by identifying nucleotides incorporated against a complementary template nucleic acid strand, one can identify the sequence of nucleotides in the template strand. A variety of such methods have been previously described. These methods include iterative processes where individual nucleotides are added one at a time, washed to remove free, unincorporated nucleotides, identified, and washed again to remove any terminator groups and labeling components before an additional nucleotide is added. Still other methods employ the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added (See, e.g., Eid, J. et al., Science, 323(5910), 133-138 (2009)).

In any of the enzyme mediated template-dependent processes, the overall fidelity, processivity and/or accuracy of the incorporation process can have direct impacts on the sequence identification process, e.g., lower accuracy may require multiple fold coverage to identify the sequence with a high level of confidence.

The present invention provides methods, systems and compositions that provide for increased performance of such polymerization based sequencing methods, among other benefits.

BRIEF SUMMARY OF THE INVENTION

In some aspects, the invention provides a method for isolating a polymerase-nucleic acid complex comprising: forming a polymerase-nucleic acid complex by mixing: (a) a polymerase enzyme comprising strand displacement activity, and (b) a nucleic acid comprising a double stranded portion comprising a first strand and a complementary second strand; initiating nucleic acid synthesis by the polymerase enzyme to produce a nascent strand complementary to the first strand, thereby displacing a portion of the second strand; halting or reducing the rate of nucleic acid synthesis; hybridizing a hook oligonucleotide to the complex through a capture region on the hook oligonucleotide that is complementary to at least some of the displaced portion of the second strand; and isolating the complex using the hook oligonucleotide.

In some embodiments, the invention further includes loading the isolated complex onto a substrate.

In some embodiments, the invention further includes carrying out single-molecule nucleic acid sequencing with the polymerase-nucleic acid complex on the substrate.

In some embodiments the nucleic acid is a circular nucleic acid. In some embodiments the nucleic acid comprises a double stranded central region and single stranded hairpin end regions. In some embodiments the nucleic acid comprises a linear nucleic acid comprising a linear double-stranded adaptor. In some embodiments the hook nucleotide also has a retrieval region having a sequence that allows the hook nucleotide to be bound and retrieved from a reaction mixture. In some embodiments the retrieval region is complementary to a sequence attached to beads, and the beads are used for the isolation of the nucleic acid.

In some embodiments the beads are magnetic beads. In some embodiments the retrieval region comprises poly(A), poly(dA), poly(T) or poly(dT). In some embodiments the hook comprises a member of a binding pair providing for removal of the hook oligonucleotide bound to the nucleic acid in order to isolate the nucleic acid or polymerase-nucleic acid complex to which it is bound. In some embodiments the binding pair comprises biotin, digoxigenin, a protein, or an antibody.

In some embodiments halting or rate reduction comprises adding a limiting amount of polymerase synthesis reagents. In some embodiments the limiting reagents comprise nucleotides or nucleotide analogs. In some embodiments halting or rate reduction comprises adding reagents to stop the polymerization reaction after a time.

In some embodiments the capture region comprises a universal capture region. In some embodiments the capture region comprises a sequence that is specific for isolation of a desired template molecule. Throughout the application, either the term isolation or the term removal is used to separating a component from other components in a mixture. For example, in some cases there is removal of the hook oligonucleotide by a bead. The removal of the hook oligonucleotide results in isolation of the compound to which the hook oligonucleotide is attached. The hook oligonucleotide can be bound to a molecule-of-interest including a polymerase-nucleic acid complex.

In some embodiments a plurality of hook oligonucleotides are added, each having a specific capture sequence that is specific for isolation of a polymerase-nucleic acid complex comprising a desired template molecule. In some embodiments a first hook oligonucleotide having a first capture sequence that is specific for isolation of a polymerase-nucleic acid complex comprising desired set of template molecules is added, and the complex is isolated, then a second hook oligonucleotide having a second capture sequence is added for the isolation of a polymerase-nucleic acid complex comprising desired template molecules comprising regions complementary to both the first and second sequences. In some embodiments the first strand of the nucleic acid comprises a single-stranded upstream of the double stranded region, and the polymerase-nucleic acid complex further comprises a primer complementary to the single stranded portion of the first strand.

In some aspects, the invention provides a method comprising: fragmenting a double stranded DNA sample into double stranded fragments; ligating to each end of the double stranded fragments a hairpin to produce a population of circular DNA templates having a central double stranded region and hairpin regions on each end; exposing the population of circular DNA templates to a primer complementary to the single stranded portion of a hairpin region of the template and to a DNA polymerase enzyme having strand displacement activity under conditions in which a population of polymerase-template-primer complexes are formed; initiating polymerase mediated DNA synthesis to extend the primer, whereby the primer is extended into the double stranded region, displacing the portion of the double strand; halting or reducing the rate of synthesis of DNA; adding to the population of complexes a hook oligonucleotide comprising a capture region complementary to a portion of the double strand under conditions where hybridization occurs; using the hook oligonucleotide to isolate the complexes to which it hybridized; thereby isolating complexes having active polymerase enzyme from complexes that are not active.

In some embodiments the hook nucleotide also has a retrieval region having a sequence that allows the hook oligonucleotide to be bound and retrieved from a reaction mixture. In some embodiments the retrieval region is complementary to a sequence attached to beads, and the beads are used for the isolation of the nucleic acid. In some embodiments the retrieval region comprises poly(A), poly(dA), poly(T) or poly(dT). In some embodiments the hook comprises a member of a binding pair providing for removal of the hook nucleotide bound to the nucleic acid, resulting in isolation of then polymerase-nucleic acid complex. In some embodiments the binding pair comprises biotin, digoxigenin, a protein, or an antibody.

In some embodiments halting or rate reduction comprises adding a limiting amount of polymerase synthesis reagents. In some embodiments the limiting reagents comprise nucleotides. In some embodiments halting or rate reduction comprises adding reagents to stop the polymerization reaction after a time. In some embodiments the capture region comprises a universal capture region. In some embodiments the universal capture region of the hook oligonucleotide comprises a portion of the single stranded region of the hairpin and a portion of the double stranded region of the hairpin that is displaced. In some embodiments the capture region comprises a sequence that is specific for isolation of complexes comprising a desired template molecule. In some embodiments the capture region comprises a sequence that is specific for isolation of complexes comprising a desired template molecule.

In some embodiments a plurality of hook oligonucleotides are added, each having a specific capture sequence that is specific for isolation of complexes comprising a desired template molecule. In some embodiments a first hook oligonucleotide having a first capture sequence that is specific for removal of a desired template molecule is added, and the complex is isolated, then a second hook oligonucleotide having a second capture sequence is added for the removal of desired template molecules comprising regions complementary to both the first and second sequences.

In some embodiments one of the capture sequences is directed to one of the template strands, and the other capture sequence is directed to the other template strand. In some embodiments prior to isolating the polymerase-nucleic acid complexes, a polymerase trap is added to remove uncomplexed polymerase enzyme. In some embodiments the polymerase trap comprises heparin.

In some aspects, the invention provides a method for DNA sequencing comprising isolating active complexes, loading the active complexes onto a substrate such that single complexes can be individually optically resolved; exposing the active complexes to a plurality of differentially labeled nucleotide analogs whose labels are cleaved upon incorporation, and initiating DNA synthesis and observing each complex to determine the time sequence of nucleotides that are incorporated.

In some embodiments the substrate comprises an array of zero mode waveguides. In some embodiments the complexes are bound to the substrate through a biotin-avidin or a biotin-streptavidin linkage.

In some aspects, the invention provides a method for loading polymerase-nucleic acid complexes onto a substrate comprising: providing a solution of beads, individual beads having bound thereto a plurality of polymerase-nucleic acid complexes; exposing the solution to a substrate comprising coupling groups selective for coupling the polymerase-nucleic acid complexes to the substrate; and applying a field to draw the particles to the substrate and to move the particles across the surface of the substrate, whereby polymerase-nucleic acid complexes become bound to the substrate through the coupling groups.

In some cases, rather than having a plurality of polymerase-nucleic acid complexes, there is one polymerase-nucleic acid complex for each bead. In this manner, the beads can be used to deposit a single polymerase-nucleic acid complex in a given region of the substrate, for example, one polymerase-nucleic acid complex per zero mode waveguide on the substrate.

In some embodiments, the invention further includes removing the beads from the substrate, leaving the bound polymerase-nucleic acid complexes on the substrate.

In some embodiments the field is a magnetic, electric, or gravitational field. In some embodiments the field to draw the particles to the substrate and the field to move the polymerase-nucleic acid complexes comprise different fields. In some embodiments the field comprises a magnetic field.

In some embodiments the magnetic field is applied using one or more permanent magnets that are moved with respect to the substrate. In some embodiments the magnetic field is applied using one or more electromagnets. In some embodiments the substrate comprises an array of zero mode waveguides. In some embodiments the beads have diameters that are greater than the diameter of the zero mode waveguide.

In some embodiments, after applying the field, a portion of the zero mode waveguides have a single polymerase-nucleic acid complex attached thereto.

In some aspects, the invention provides a method for loading active polymerase-nucleic acid complexes onto a substrate comprising: providing a solution of magnetic beads having polymerase-nucleic acid complexes bound thereto, each polymerase-nucleic acid complex comprising a polymerase enzyme, and a template nucleotide; contacting the solution of magnetic beads with the top of a substrate comprising an array of nanoscale wells having bases, wherein the bases of the wells have coupling agent bound thereto; and applying a dynamic magnetic field to move the magnetic beads in solution down to the top of the substrate, whereby the dynamic magnetic field causes the particles to be moved across the top surface of the substrate, whereby some polymerase-nucleic acid complexes become bound to the coupling groups on the bases of the nanoscale wells.

In some embodiments the polymerase-nucleic acid complexes are bound to the magnetic bead via hybridization between an oligonucleotide attached to the magnetic bead and a sequence on the template nucleic acid. In some embodiments the magnetic bead is attached to a hook oligonucleotide comprising a retrieval sequence that is complimentary to an oligonucleotide attached to the magnetic bead and a capture sequence that is complementary to the template nucleic acid. In some embodiments the oligonucleotide attached to the magnetic bead comprises a poly(dA), poly(A), poly(dT) or poly(T) sequence.

In some embodiments the relative binding strength of each of i) the magnetic bead to the hook oligo, ii) the hook oligo to the template nucleic acid, and iii) the polymerase-nucleic acid complex to the substrate are controlled such that when the polymerase-nucleic acid complex becomes bound to the substrate while applying the dynamic magnetic field, the attachment between the hook oligo and the template nucleic acid is broken.

In some embodiments the dynamic magnetic field is produced using one or more moving permanent magnets. In some embodiments the dynamic field is produced using one or more electromagnets. In some embodiments the nanoscale wells are cylindrical, and the diameters of the magnetic beads are greater than the diameter of the nanoscale wells. In some embodiments the coupling agent at the bases of the wells comprises biotin. In some embodiments the polymerase enzyme is attached to streptavidin, neutravidin, or avidin for binding to the coupling agent.

In some aspects, the invention provides an apparatus comprising; a fixture for holding a substrate; a substrate held within the fixture comprising an array of zero mode waveguides on its top surface, and comprising a reservoir for containing a solution in contact with the top surface of the substrate; a solution, in contact with the substrate, comprising magnetic beads having polymerase-nucleic acid complexes attached thereto; a device for generating a dynamic magnetic field disposed below, adjacent to, or above the substrate capable of generating a magnetic field that (i) pulls the magnetic beads to the top surface of the substrate and (ii) moves the magnetic beads across the top surface of the substrate, whereby polymerase-nucleic acid complexes are deposited into the zero mode waveguides on the substrate.

In some embodiments the polymerase-nucleic acid complexes are bound to the magnetic bead via hybridization between an oligonucleotide attached to the magnetic bead and a sequence on the template nucleic acid. In some embodiments the magnetic bead is attached to a hook oligonucleotide comprising a retrieval sequence that is complimentary to an oligonucleotide attached to the magnetic bead and a capture sequence that is complementary to the template nucleic acid. In some embodiments the oligonucleotide attached to the magnetic bead comprises a poly(dA), poly(A), poly(dT) or poly(T) sequence.

In some embodiments the relative binding strength of each of i) the magnetic bead to the hook oligo, the hook oligo to the template nucleic acid, and iii) the polymerase-nucleic acid complex to the substrate are controlled such that when the polymerase-nucleic acid complex becomes bound to the substrate while applying the dynamic magnetic field, an attachment between the hook oligo and the template nucleic acid is broken.

In some embodiments the dynamic magnetic field is produced using one or more moving permanent magnets. In some embodiments the dynamic field is produced using one or more electromagnets.

In some embodiments the nanoscale wells are cylindrical, and the diameters of the magnetic beads are greater than the diameters of the nanoscale wells. In some embodiments the coupling agent at the bases of the wells comprises biotin. In some embodiments the polymerase enzyme is attached to streptavidin, neutravidin, or avidin for binding to the coupling agent.

In some aspects, the invention provides a method for depositing molecules-of-interest onto a substrate comprising: providing a solution of beads wherein each bead comprises a plurality of molecules-of-interest linked thereto by a bead to molecule-of-interest linkage; exposing the solution of beads to a substrate, the surface of the substrate comprising binding molecules for binding the molecules-of-interest; using a contacting force to bring the beads into proximity or into physical contact with the substrate and optionally using a distributing force to move the beads across the surface of the substrate; and removing the beads from the substrate, thereby producing a substrate having molecules-of-interest bound to its surface through the binding molecules.

In some embodiments the bead to molecule-of-interest linkage comprises hybridized oligonucleotides. In some embodiments the hybridized oligonucleotides have from about 5 to about 40 complementary bases. In some embodiments the binding molecules comprise biotin, a biotin binding protein, an antigen or an antibody. In some embodiments the contacting force comprises a gravitational, magnetic, electrical, or dielectric, or centrifugal force. In some embodiments the beads comprise magnetic beads and contacting and distributing forces comprise magnetic forces.

In some embodiments the substrate comprises an array of nanoscale wells having binding molecules on the bases of the wells whereby the molecules-of-interest become attached to the bases of the wells. In some embodiments the molecule-of-interest comprises a protein or a nucleic acid. In some embodiments the molecule-of-interest comprises an enzyme.

BRIEF DESCRIPTION OF THE DRAWINGS

FIG. 7 shows some strategies for using reversible stops in a nucleic acid template to control the polymerase walk-in.

FIG. 23 outlines a method for using the walk-in of a polymerase enzyme into a SMRTbell™ template to expose a modified base to a binding protein or antibody for specific capture.

DETAILED DESCRIPTION OF THE INVENTION

Figure 1:
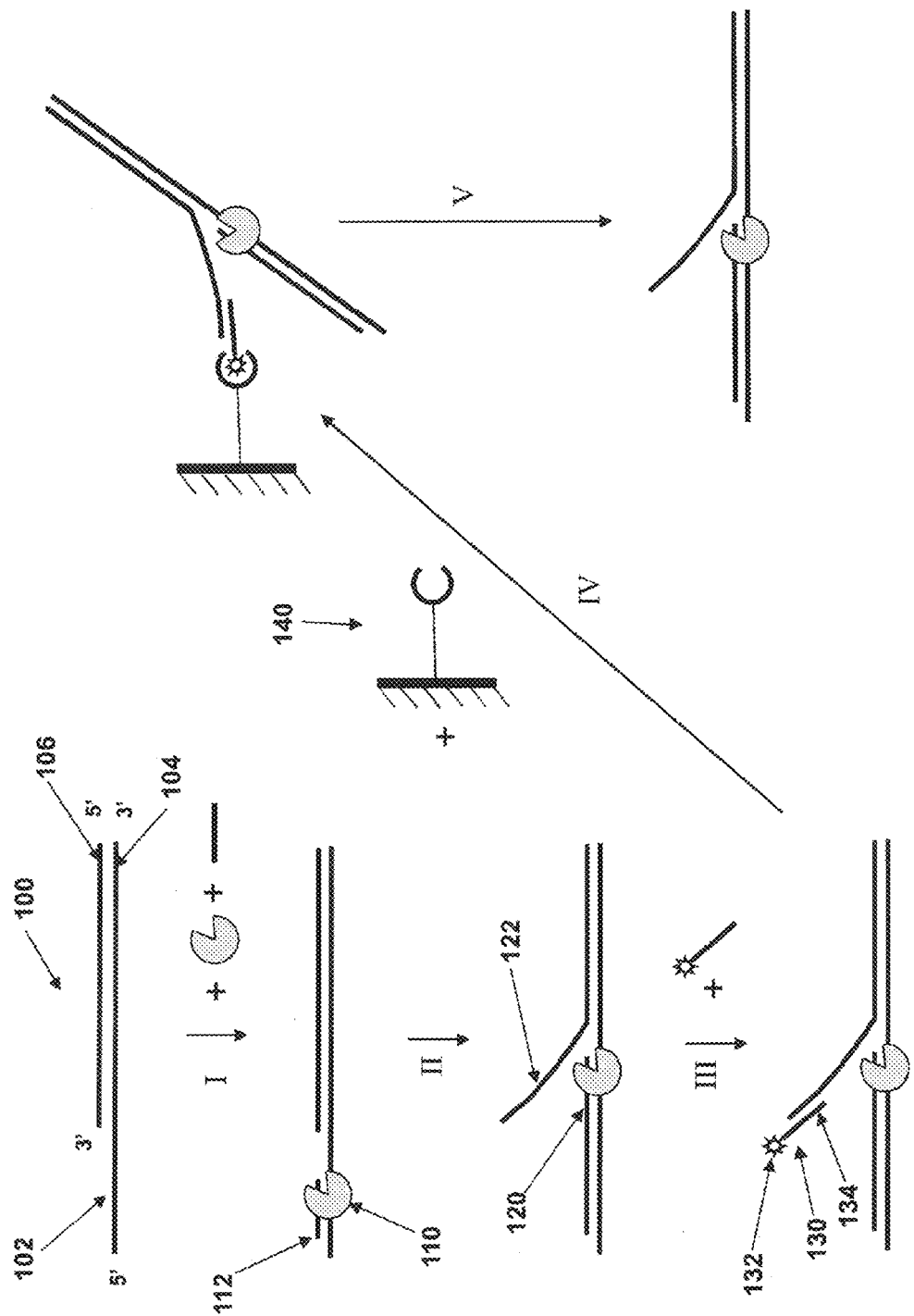
FIG. 1 shows an embodiment of the invention for isolating active polymerase-nucleic acid complexes.

In some aspects, the present invention provides methods and compositions for isolating nucleic acids and polymerase-nucleic acid complexes. Isolation generally involves removing desired nucleic acids or polymerase-nucleic acid complexes from a mixture of other components including undesired components. In other aspects the invention provides methods of loading of polymerase-nucleic acid complexes onto substrates for analysis, for example for nucleic acid sequencing, and in particular for single-molecule nucleic acid sequencing.

When carrying out single-molecule sequencing, it is often desirable to attach a polymerase-nucleic acid complex to the surface of a substrate, where the attachment is either through the polymerase enzyme or through the nucleic acid. When immobilizing these complexes for subsequent sequencing reactions, it is generally desirable that a large fraction of the complexes are active, such that when the sequencing reaction is carried out, the polymerase will carry out nucleic acid synthesis as required for sequencing. An approach to ensuring a high active fraction is to prepare polymerase-enzyme complexes in solution, then to perform a process to separate the active complexes from those which are inactive. Other approaches toward isolating and purifying the active fraction of polymerase-nucleic acid complex is described in copending U.S. patent application entitled Purified Extended Polymerase/Template Complex for Sequencing" 61/385,376, filed Sep. 22, 2010, which is incorporated herein by reference in its entirety for all purposes. We have invented and describe herein an approach that allows for selection of the active fraction within the sample. In addition to purifying the active fraction of polymerase-nucleic acid, the methods and compositions described herein allow for the selection and isolation of specific desired nucleic acid molecules within a population of different molecules. The methods, compositions, and apparatuses of the invention also provide improved methods of loading template-nucleic acid complexes onto a substrate, for example for single-molecule nucleic acid sequencing.

The methods and compositions of the invention that are directed to isolating nucleic acids or polymerase-nucleic acid complexes utilize the ability of a polymerase having strand displacement activity to open up a double stranded region to expose a sequence within the region. This exposed sequence can then be targeted and captured using a molecule for specific capture of the sequence. The molecule is referred to herein as a hook molecule. In some cases, capture is performed using an oligonucleotide in the hook molecule that is complementary to the sequence, referred to herein as a hook oligonucleotide. Because an active enzyme is required to open up the sequence, exposed sequence is only available for hybridization and capture for those nucleic acid molecules complexed with an active polymerase. Where a polymerase-nucleic acid complex is inactive, no sequence from the double-stranded region is exposed, and therefore no capture takes place. Thus the hook oligonucleotide can be used to capture only those complexes that are active, allowing for the isolation of active complexes from those that are inactive.

The methods and compositions of the invention are also directed to the isolation of polymerase enzyme-nucleic acid complexes from other components of a mixture including separating the polymerase enzyme-nucleic acid complexes from free, uncomplexed enzyme. This can be accomplished by using a hook molecule designed to capture a target sequence within the nucleic acid. The hook molecule can be, for example, a hook oligonucleotide that is complementary to a sequence within the nucleic acid in the complex. For this type of capture, the nucleic acid will generally have both a double stranded and a single stranded portion. A hook molecule can be designed to be complementary to the single stranded portion of the nucleic acid, allowing for capture without denaturing or opening the double stranded region of the nucleic acid. In some cases, a library of DNA fragments is formed where each of the DNA fragments may have a unique sequence, and where each of the fragments has a common, or universal, single stranded region. The use of a common or universal region allows for capturing many complexes, each with regions having different sequences. In other cases, the hook oligo can be targeted to regions within portions of the fragments having different sequences. This approach can be used for selectively removing nucleic acids from the population which include a desired sequence. In some cases the single stranded region to which the hook oligonucleotide is complementary comprises a hairpin region of the nucleic acid. The hairpin regions can be the hairpin regions of SMRT Bell™ templates which are described in more detail below. The methods that target a common or universal sequence in single stranded portion of the population of nucleic acids will generally not provide a purification of active from inactive complexes the way that the methods described herein including enzyme walk-in will, but the protocols for this method can be simpler, and still allow for being able to use higher ratios of enzyme to nucleic acid in order to provide higher yields of complex, then providing for removal of the excess, uncomplexed enzyme. This method also allows for greater quantitation by measuring the concentration of complex after the purification from uncomplexed enzyme. The components and conditions, including hook molecules described herein both for methods including enzyme walk-in and those methods not employing walk-in.

The method can comprise, for example, the following steps. First, a polymerase-nucleic acid complex is formed between a polymerase enzyme having strand displacement activity, and a nucleic acid comprising a double stranded portion. The complex usually also includes a primer that is hybridized to one of the strands of the nucleic acid. Once the complex is formed, nucleic acid synthesis is initiated. The synthesis is carried out under the appropriate conditions generally including the presence of four nucleotides and the requisite salts, metals, and buffers. The active polymerase enzymes will produce a nascent strand complementary to the first strand, thereby displacing a portion of the second strand of the double stranded portion. Before the enzyme completes the synthesis of the strand, the nucleic acid synthesis is halted or slowed. This results in the polymerase enzyme being stopped, but remaining part of the sequencing complex.

A hook molecule such as a hook oligonucleotide, having a region that is complementary to the displaced and exposed portion of the nucleic acid is then added. The region of the hook oligonucleotide that is complementary to the exposed portion of the nucleic acid is referred to as the capture region. In addition to the capture portion, the hook molecule has a retrieval portion for isolation of the nucleic acid. The retrieval portion can be an oligonucleotide sequence, a member of a binding pair, or the capture portion can be a solid substrate such as a bead or planar surface. The retrieval portion allows for the isolation of the polymerase-nucleic acid complex from other molecules in the mixture including inactive complexes. In preferred embodiments, the retrieval portion is a magnetic bead, or is used to attach the polymerase-nucleic acid complex to a magnetic bead. The polymerase-nucleic acid complex can then be separated from the other components of the mixture by well known methods of magnetic bead purification. The isolated polymerase-nucleic acid complex can then be removed from the hook molecule for subsequent use, such as for nucleic acid sequencing. For example, where the hook molecule is a hook oligonucleotide that is hybridized to the polymerase-nucleic acid complex, the polymerase-nucleic acid complex can be released by raising the stringency of the solution, for example by lowering the ionic strength or raising the temperature.

These methods and compositions can be used to selectively isolate active complexes from inactive complexes and other components in the mixture used to create the complexes. The methods and compositions can also be used to selectively isolate nucleic acids and polymerase-nucleic acid complexes having specific sequences from a mixture of nucleic acids. For example, for DNA sequencing, genomic DNA can be fragmented into a mixture of double-stranded pieces falling within a desired size range. The fragments can be treated, e.g. by ligation of adapters to the ends of the fragments. These adapters can be used as sites for priming and for formation of polymerase-nucleic acid complexes. With the methods described herein, hooks to universal sequences can be used to either isolate the active fraction from other components in the mixture regardless of the sequence of the nucleic acid fragment, or specific hooks can be used to selectively remove fragments containing desired sequences.

The isolated polymerase-nucleic acid complexes can be used for loading active polymerase-nucleic acid complex onto substrates for nucleic acid (e.g. DNA) sequencing. In some cases, the polymerase-nucleic acid complexes are washed from the hook molecules, e.g. using high stringency, then the solution of polymerase-nucleic acid complexes is added to a substrate for attachment of the complexes. In some cases, we have found that beads onto which the polymerase-nucleic acid complexes are attached can be used to load the complexes onto the surface without prior removal of the complexes from the beads. For example, magnetic beads having polymerase-nucleic acid complexes bound to them by hybridization can be added to a substrate in the form of a solution, and a magnetic field applied to bring the beads down to the substrate, allowing the complexes to contact the surface of the substrate, and become bound to it. We have found that providing a dynamic (as opposed to a static) magnetic field that moves the beads around on the surface of the substrate helps in successful binding of the complexes to the surface. The surface binding can be accomplished by having coupling groups attached to the surface, and having molecules to which the coupling groups bind on the polymerase-nucleic acid complexes. In some embodiments, the polymerase will have a biotin binding protein such as streptavidin, and the surface will have biotin coupling groups attached to it. The strong chemical interaction between the biotin and the binding protein will result in the immobilization of the polymerase. Where there is a relatively weak binding between the hook molecule and the template nucleic acid (e.g. through nucleic acid hybridization) the polymerase-nucleic acid complex can become bound to the surface and the force of the magnetic field will displace the hook from the complex, leaving the bound complex on the surface of the substrate. In preferred embodiments, the substrate comprises an array of zero mode waveguides in the form of nanoscale wells in which the nanoscale wells have coupling groups such as biotin on the bases of the wells, resulting in the deposition of polymerase-nucleic acid complexes in the zero mode waveguides.

FIG. 1 illustrates an embodiment of the invention for the isolation of polymerase-nucleic acid complexes. A nucleic acid having a double stranded nucleic acid region 100 is provided. The double stranded region has a first strand 104, and a second strand 106. In this embodiment, the first strand 104 acts as the template strand, and the second strand 106 is complementary to this strand. The double stranded nucleic acid 100 can be part of a mixture of different sequences, for example from a library of nucleic acid fragments. In preferred embodiments, the nucleic acid is DNA, but it can also comprise RNA residues or RNA strands and can also include non-natural nucleotides. In the embodiment shown in FIG. 1, the nucleic acid 100 has a double stranded region, and also has a single stranded region. The single stranded region provides a place for the hybridization of a primer 112. While a single stranded region is useful for the invention, it is not absolutely required. In some cases, for example, the nucleic acid in one strand can be nicked to provide a starting point for nucleic acid synthesis, and in some cases terminal protein can be used to initiate synthesis in the absence of a primer.

In step (I) a primer 112 and a polymerase enzyme 110 are added to form the polymerase-nucleic acid complex. The appropriate salts, metals, buffers, etc. are added during complex formation. In some cases one or more natural or unnatural nucleotides is added to stabilize the complex by keeping the polymerase enzyme in a conformation that will remain bound to the nucleotide. As is well known in the art, the polymerase enzyme is able to identify and bind to the appropriate location at the 3' end of a primer poised for nucleic acid synthesis. In some cases, it is desirable to add an excess of polymerase enzyme in step (I) to ensure a high yield of complex formation. For example, in some cases, molar ratios of 10:1 to 50:1 of polymerase enzyme to nucleic acid are used. Being able to use such a large excess of polymerase is an advantage of the current method, because the subsequent isolation of the desired nucleic acid complex allows for isolation from the excess added polymerase.

In step (II), nucleic acid polymerization is initiated, resulting in the formation of a nascent strand 120 extended from the primer. In order to initiate polymerization, all of the required components, including all necessary nucleotides are added to the solution containing the complex. The polymerase enzyme that is used has strand displacement activity. This results in the displacement of the second strand 106 that is complementary to the first (template) strand 104, producing a displaced single stranded region of the second strand 122.

In step (III) a hook molecule 130 attaches to a sequence that was exposed by the action of the polymerase enzyme through a capture region 134 on the hook molecule. In preferred embodiments, the hook molecule is a hook oligonucleotide having a capture sequence that is complementary to a sequence on the displaced second strand. The hook molecule also has a retrieval region 132 that allows the hook attached to the polymerase-nucleic acid complex to be separated from other components in the mixture. As shown in FIG. 1, the retrieval region 132 can be a member of a binding pair that will bind to a surface for retrieval. In other cases, the retrieval region can be a bead or solid surface.

In step (IV) an affinity substrate 140 having an affinity for the retrieval portion of the hook molecule is added, the substrate selectively binding the retrieval portions of the hook molecules. The affinity substrates can comprise beads or planar surfaces that have bound to them agents to bind to the retrieval portion of the hook molecules. In some cases, the affinity substrates can comprise magnetic beads. In some cases, magnetic beads having poly(T) sequences are used to hybridize to poly(A) regions on the retrieval portions of the hook molecules. The use of magnetic beads for separation of biomolecules is well developed. Once the polymerase-nucleic acids are attached to the affinity substrates, other components of the solution can be washed away providing isolation of the complexes. In addition to washing away of inactive polymerase-nucleic acid complex, the process can remove other components from the complexation reaction such as removing excess uncomplexed polymerase enzyme.

In some cases, a polymerase trap is added prior to the step of washing away the components of the complex forming reaction. A polymerase trap is used to bind excess free polymerase within the reaction in order to more effectively remove it from the desired polymerase-nucleic acid complex by washing. A useful polymerase trap is heparin, to which polymerases are known to bind. Nucleic acids such as DNA can also be used as polymerase traps to assist in removal of the excess polymerase. In some cases, single stranded DNA such as circular single stranded DNA can be used.

In step (V) the retrieved polymerase-nucleic acid complex is removed from the hook molecule and from the affinity substrate. Where the hook molecule is a hook oligonucleotide having a capture sequence that is hybridized to the polymerase-nucleic acid complex, the polymerase-nucleic acid complex can be removed from the hook oligonucleotide by treatment with high stringency conditions, e.g. low salt concentration and/or higher temperature. The isolation process can provide for adjusting the concentration of the polymerase-nucleic acid complex. For example, where the polymerase-nucleic acid complex is released into a volume that is smaller than the volume it was in prior to isolation, the concentration of the polymerase-nucleic acid can be increased.

The process of FIG. 1 can be used to increase the active fraction of polymerase-nucleic acid complex. Since only active polymerases will displace the second strand to expose the capture sequence, only complexes having an active polymerase will be isolated using the hook molecule. Having a higher fraction of active complex can be valuable for single-molecule sequencing approaches where maximizing the portion of active polymerase-nucleic acid complex can result in a higher yield in the number of sequencing reactions per substrate. In addition to increasing the active fraction of complex, the methods allow for the isolation of the complex from other components in the complex-forming reactions such as excess polymerase enzyme.

In preferred aspects of the invention, the template nucleic acid is in a cyclic form. Performing single-molecule sequencing on a cyclic nucleic acid template is advantageous in that it allows for redundant sequencing of a given region. The accuracy of a sequence determination can be improved significantly by sequencing the same region multiple times. Cyclic nucleic acids that are highly useful for the current invention include SMRT Bell™ templates, which are nucleic acids having a central double-stranded region, and having hairpin regions at each end of the double-stranded region. The preparation and use of cyclic templates such as SMRT Bells™, are described for example in U.S. patent application Ser. No. 12/286,119, filed Sep. 26, 2008, and U.S. patent application Ser. No. 12/383,855, filed Mar. 27, 2009, the full disclosures of which is incorporated herein by reference for all purposes. One advantage of the SMRT Bell™ template is that it can be made from a library of double-stranded nucleic acid, e.g. DNA, fragments. For example, a sample of genomic DNA can be fragmented into a library of DNA fragments, by known methods such as by shearing or by use of restriction enzymes. The library of DNA fragments can be ligated to hairpin adaptors at each end of the fragment to produce a library of SMRT Bell™ templates. The hairpin adaptors provide single stranded regions within the hairpins. By using the same hairpin adaptor for all of the fragments, the hairpin adaptors provide a position for universal priming of all of the sequences.

Figure 2:
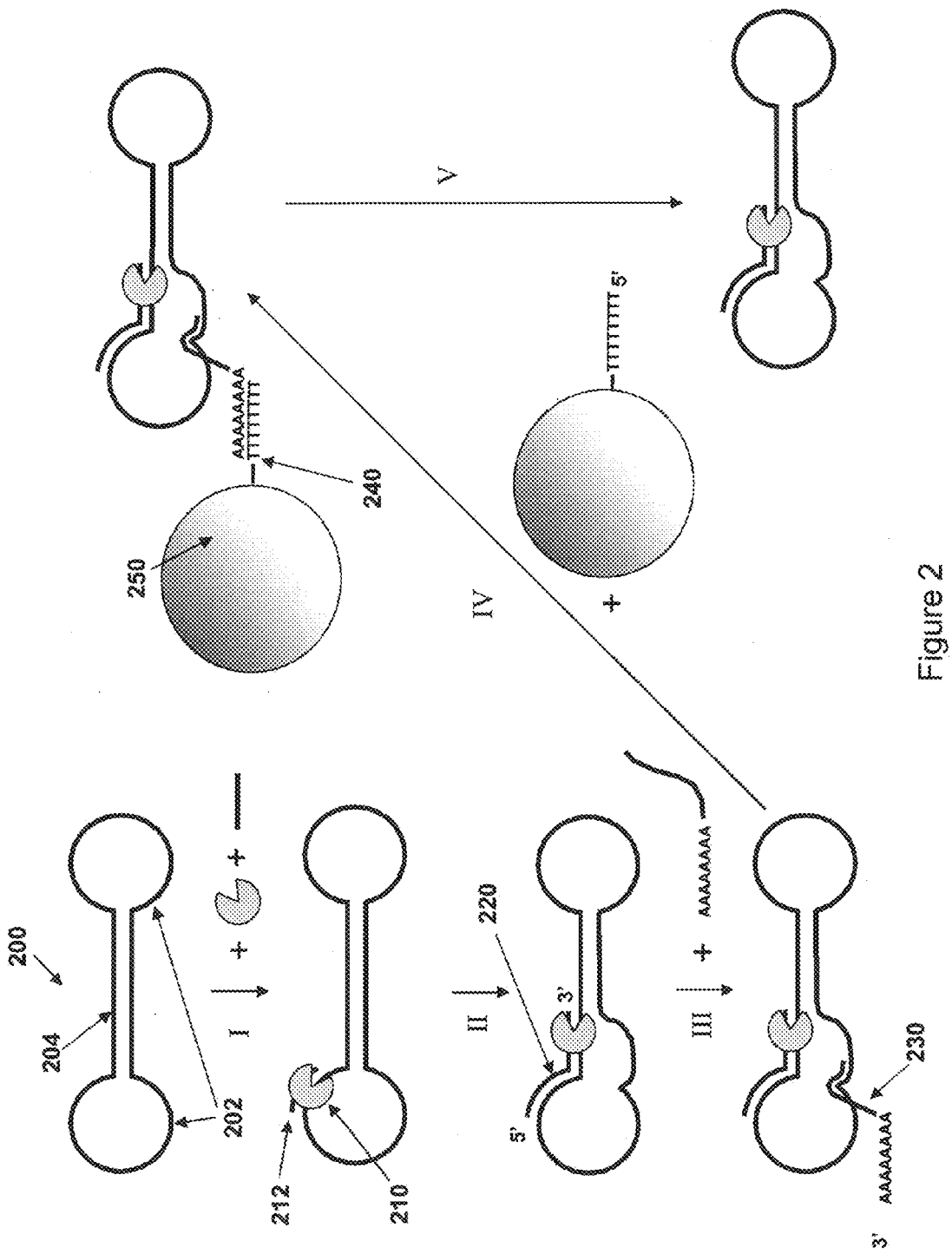
FIG. 2 illustrates the isolation of active complexes using SMRTBell™ templates, a hook oligonucleotide, and beads.

FIG. 2 shows an embodiment of the invention using circular, SMRT Bell™ templates. The SMRT Bell™ templates 200 are provided having a central double stranded region 204 and having hairpin regions 202 on the ends of the double stranded region. In some cases, the SMRT Bell™ can comprise a library of different sequences in the double-stranded region 204. In step (I), a primer 212 is added that is designed to hybridize to the single stranded region of the hairpin region of the template nucleic acid. A polymerase enzyme 210 having strand-displacement activity is also added under conditions in which the polymerase enzyme will form a complex with the template and primer.

In step (II) template directed nucleic acid synthesis is initiated by adding the required reagents under the appropriate conditions. The reagents for carrying out nucleic acid synthesis are well known and include nucleotides, salts, and metals in solution at the appropriate concentrations and pH. As the polymerase enzyme extends the primer, it moves into the double stranded region, displacing the nucleotide strand that is complementary to the strand it is using as a template for synthesis. The polymerase enzyme is then halted or the rate of synthesis is reduced. The rate is reduced such that few, if any, nucleotide units will be added during the subsequent steps of the method. For example, the rate of enzyme synthesis is reduced by a factor of 10, 100, or 1000. In some cases, the enzyme can be halted by adding a limiting amount of reagents. The enzyme can also be halted by allowing the synthesis to proceed for a given amount of time, and then stopping the synthesis by adding an agent that halts synthesis, such as Sr++. We have found that in some cases, it is useful to run the nucleic acid synthesis in the presence of Ca++. Having Ca++ as the divalent metal in the reaction, and very little to no Mg++ or Mn++, the polymerization proceeds, but quite slowly, and in a controlled fashion, allowing for controlling the amount of walk-in before halting synthesis. In some cases, the halting or slowing of rate is accomplished by buffer exchange. The walk-in can also be controlled by including modified nucleotide residues within the template nucleic acid that act to halt or significantly slow nucleic acid synthesis. The modifications which lead to the halting of the synthesis can be made in a reversible fashion, allowing them to be removed for subsequent sequencing reactions. The reversible modifications can be removed by light or by the addition of reagents for their specific removal.

After the polymerase reaction is halted, in step (III) a hook molecule is added. The hook molecule 230 has a capture region that is specific for binding to the portion of the nucleic acid that was exposed upon nucleic acid synthesis and opening up of the double stranded region. In the embodiment of FIG. 2, the hook molecule is a hook oligonucleotide having a capture region that is complementary to and will hybridize specifically with the exposed portion of the nucleotide. In the embodiment of FIG. 2, the hook oligonucleotide capture region has a portion that hybridizes to the single stranded region of the hairpin, and a portion that hybridizes to the previously double-stranded portion that was opened up by the action of the polymerase enzyme. In some cases, the capture region of the hook oligonucleotide will hybridize only to the exposed former double stranded region. The hook oligonucleotide also has a retrieval region, which in the embodiment of FIG. 2 comprises a poly(A) (or poly(dA)) sequence.

In step (IV) beads 250, such as magnetic beads having retrieval moieties such as a plurality of poly(T) oligonucleotides 240 bound to their surfaces are added to the mixture. The poly(T) regions on the beads hybridize with the poly(A) regions on the hook oligonucleotide, specifically trapping onto the beads only the polymerase-nucleic acid complexes bound to the hook oligonucleotide. In the embodiment described here, beads are used. Other solid substrates can also be used, for example the retrieval moities can be part of a column, a filter medium, or can be attached to a flat solid substrate such as a hybridization microarray. During the trapping the stringency of the solution is controlled in order to favor capture, for example by controlling the ionic strength and the temperature of the solution. Once the captured complexes are attached to the beads, the beads can be washed to remove other components within the reaction mixture. For example excess polymerase and un-complexed nucleic acid and primer can be removed. In addition, complex that was formed, but was not active, will not have exposed regions to be captured by the hook molecule, so these inactive complexes can be removed. In some cases, a hook having a specific capture region designed to hybridize with nucleic acids having a desired sequence is used. In these cases, the washing will also remove complexes that do not have the desired sequence even where the complex is active.

In step (V), the desired active polymerase-nucleic acid complex is removed from the hook molecule and the bead. Where a hook oligonucleotide is used, removal can be accomplished by raising the stringency of the solution such that the capture region of the hook oligonucleotide no longer hybridizes to the complex. The concentration of the complex that is isolated can be controlled by controlling the volume into which the oligonucleotide is eluted. By keeping this volume low, the concentration of the complex can be kept relatively high. In some cases, the process can be used to concentrate the isolated complex by using volumes smaller than the original volume into which the complex was dissolved. The complex can also be removed from the beads by physical means such as contacting the beads with a substrate having binding groups that will bind the complex strongly and sever the bond to the bead. In some cases, the beads physically contact the surface of the substrate, in other cases, the beads are brought into proximity with the substrate.

Figure 3:
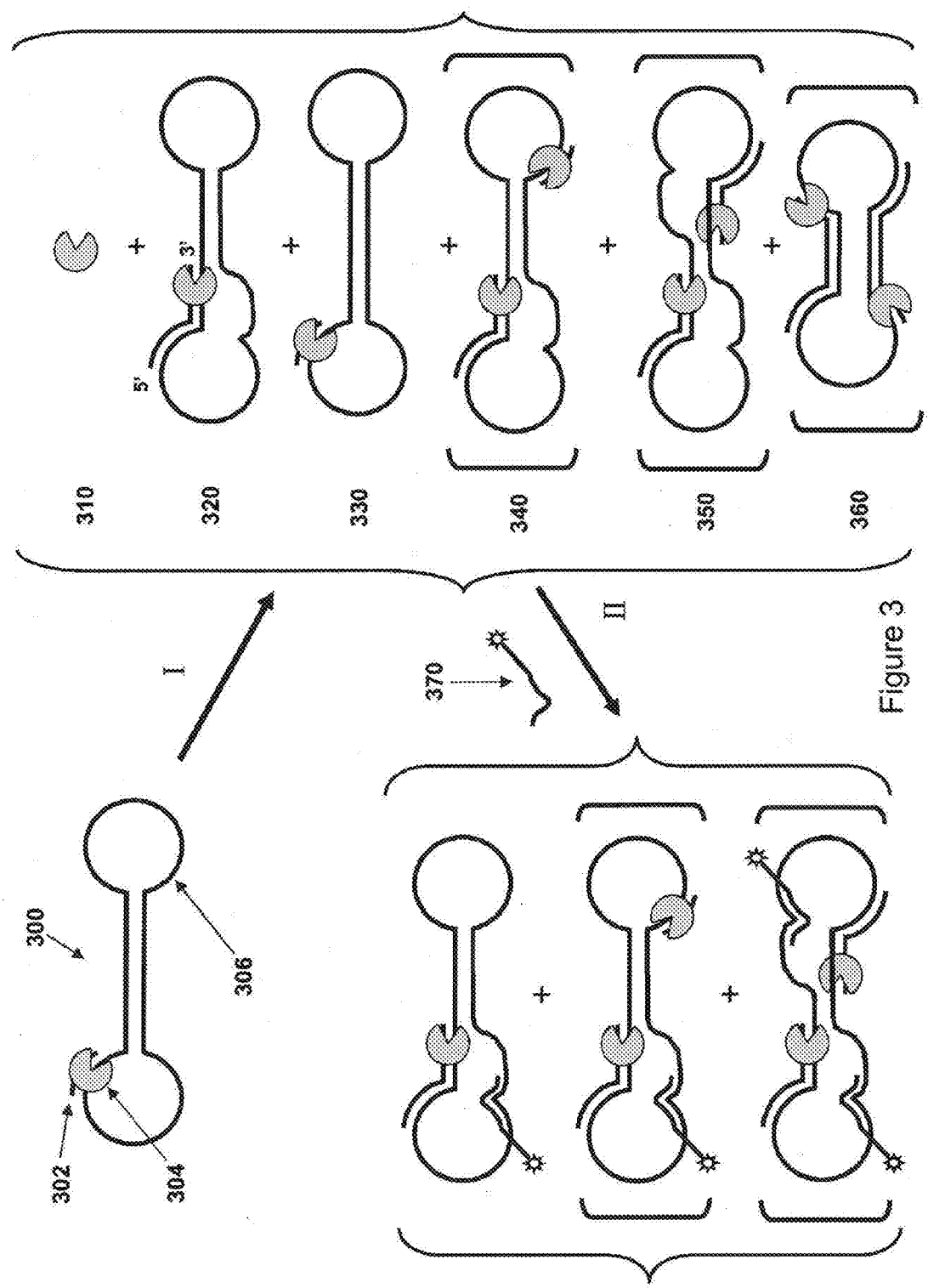
FIG. 3 illustrates some potential species in solution after a polymerase-nucleic acid complex is formed, and the polymerase enzyme has walked-in, and illustrates which of the species can be captured with a hook molecule.

FIG. 3 illustrates some of the species that can be formed in preparing the polymerase-nucleic acid complex and that can be removed using the hook molecule. A polymerase-nucleic acid complex is formed between a SMRTBell™ nucleic acid 306, a polymerase enzyme 304, and a primer 302. As described above, a nucleic acid synthesis reaction is carried out in step (I) to allow the polymerase to walk in, extending the primer to form a nascent strand, and displacing the non-template portion of the double stranded region. The nucleic acid synthesis is halted after the enzyme has replicated a portion of the nucleic acid. At this point, the reaction mixture may have a number of different species. Some of the species are: free, uncomplexed enzyme 310, active polymerase-nucleic acid complex 320, and inactive polymerase-nucleic acid complex 330. In some cases the hairpin regions on each end of the SMRT Bell™ template have the same sequence. Where this is the case, some complex having two polymerase enzymes can be formed. In this case the reaction mixture may also have complex with one active enzyme 340, and complex with two active enzymes 350. In some cases, a different hairpin region is at one end of the double stranded region than on the other end. Where the hairpin regions are different, the formation of species 340, and 350 can be avoided. In addition, in some cases the reaction mixture can have complex in which two active enzymes have completely replicated each of the strands in the central double stranded region 360. This can occur for example, where the double stranded region is relatively short. For the species 360, the region of the nucleic acid that was originally exposed by the enzyme becomes double stranded again as the enzyme completes replication of the strand. These species, while being active, will not be retrieved in the later part of the process.

This illustrates an aspect of the invention which accomplishes size selection. By controlling the amount of walk-in with a circular template, one can exclude the capture of species that are shorter than a certain length by walking in a distance such that the template is fully replicated, because when a circular template is fully replicated, the capture portion of the sequence is double stranded and therefore inaccessible to the hook. This replication of the complete template can be done with two enzymes per template as shown in FIG. 3, or can be done with a single enzyme per template. This can be useful, for example, in cases where short nucleic acids are not desired, which can be the case in sequencing, where longer readlengths are often desired, and where very short fragments are relatively non-productive. It can also be useful for the removal of hairpin adaptor dimers, which will have a very short double stranded region.

In step (II) the hook molecule 370 is added to the mixture. As shown, the hook molecule 370 will bind to the species in which the activity of the polymerase has opened up the double stranded region to expose the sequence to which the hook molecule, e.g. hook oligonucleotide is designed to bind. The hook molecule binds species 320, 340, and 350, which have the requisite exposed regions, but does not bind free polymerase 310, inactive complex 330, and small nucleic acids in which both of the strands in the double stranded region are fully replicated 360. The hook molecule can thus be used, for example by binding to a solid surface and washing, to isolate the bound species from those which are unbound and to isolate bound species from other components of the mixture.

Figure 4:
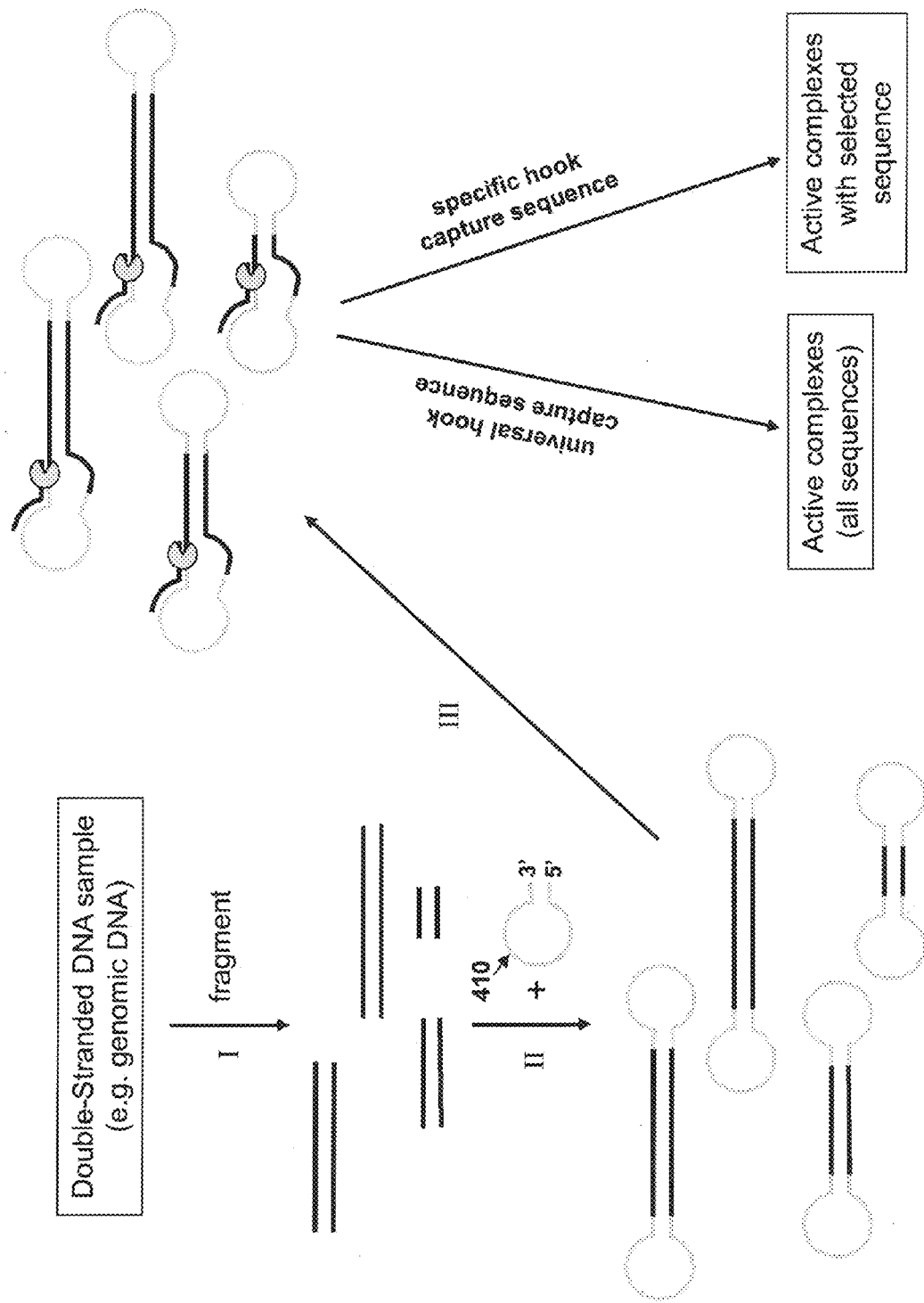
FIG. 4 shows how the invention can be used to isolate active species and to isolate species having selected sequences from a library of nucleic acid fragments.

FIG. 4 illustrates a process for isolating active complexes from a double-stranded nucleic acid sample. A double stranded nucleic acid sample, such as a genomic DNA sample, is fragmented in step (I) into a library of fragments. Fragmentation can be carried out in any suitable manner, including shearing and restriction fragmentation. The library of fragments can then be treated to produce ends that are amenable to further processing. In some cases, enzymes can be added that produce blunt ends. In some cases, the ends will have overhang regions.

In step (II), hairpin adaptors 410 are added to the fragments and ligated onto the ends to produce a SMRTBell™ construct having a central double stranded region and hairpin regions at each end. The hairpin adaptors 410 are oligonucleotides which generally have both a single stranded hairpin region and a double stranded region. As shown here, the hairpin adaptor can function as a universal sequence allowing a single primer to initiate synthesis on all of the fragments even though the fragments can have different sequences. In addition, for the purposes of the present invention, the double stranded region can act as a universal region, providing a capture sequence for attachment to the capture portion of a hook oligonucleotide, allowing all nucleic acids that have this portion of the hairpin adaptor sequence exposed to be captured, regardless of the sequence that derives from the fragment.

In some cases, the hairpin adaptors at each end of the double-stranded central region will be the same. In other cases, a hairpin adaptor comprising one sequence is provided at one end of the double stranded segment, and a hairpin adaptor with a different sequence is provided at the other end. Having different hairpin adaptors at each end generally entails using a more involved protocol, but in some cases, having separate adaptors at each end can be advantageous.

In step (III) nucleic acid synthesis is initiated, such that the polymerase enzyme extends the synthesis of the nascent strand into the double stranded region, exposing a portion of the strand that is not acting as the template. The polymerase reaction is then halted. The resulting polymerase-nucleic acid complexes can then be isolated from the reaction mixture using hook molecules. In some cases it is desired to isolate all active complexes regardless of sequence, in which case the sequence on the hairpin adaptor which is universal for all fragments can be targeted by the capture region of the hook molecule. In some cases, it is desired to select only active complexes having a specific sequence, in which case, a hook molecule having a capture region targeted only to that sequence can be used. This allows for the isolation of only those nucleic acids within the mixture of fragments which have the sequence of interest. Multiple specific hook molecules can be added where it is desired to isolate nucleic acids having any one of a set of sequences targeted by the multiple specific hook molecules.

In some cases hook sequences can be made to target sequences that are not desired, e.g. for background knockdown. There are situations, for example in DNA sequencing in which there are contaminating sequences that it is known are not desired and will use up useful sequencing resources. For example, in some cases, hook molecules can be used to target sequences representing housekeeping genes in order to remove these from the mixture. Thus, in some embodiments, hook oligonucleotides for capturing both desired and undesired sequences will be deployed, with the undesired sequences separated from those desired. This can be done sequentially, e.g. by first exposing the sample to hook oligonucleotides having the undesirable sequences, separating those beads from the sample, then in a second step exposing the sample to hook oligonucleotides targeted to the desired sequences. In some cases, hooks having desired and undesired sequences can be added at the same time. For example the hook molecules having undesired sequences can be attached to non-magnetic beads, and the hook molecules having desired sequences attached to magnetic beads, allowing for selective removal or isolation of only the desired sequences by magnetic isolation.

Figure 5:
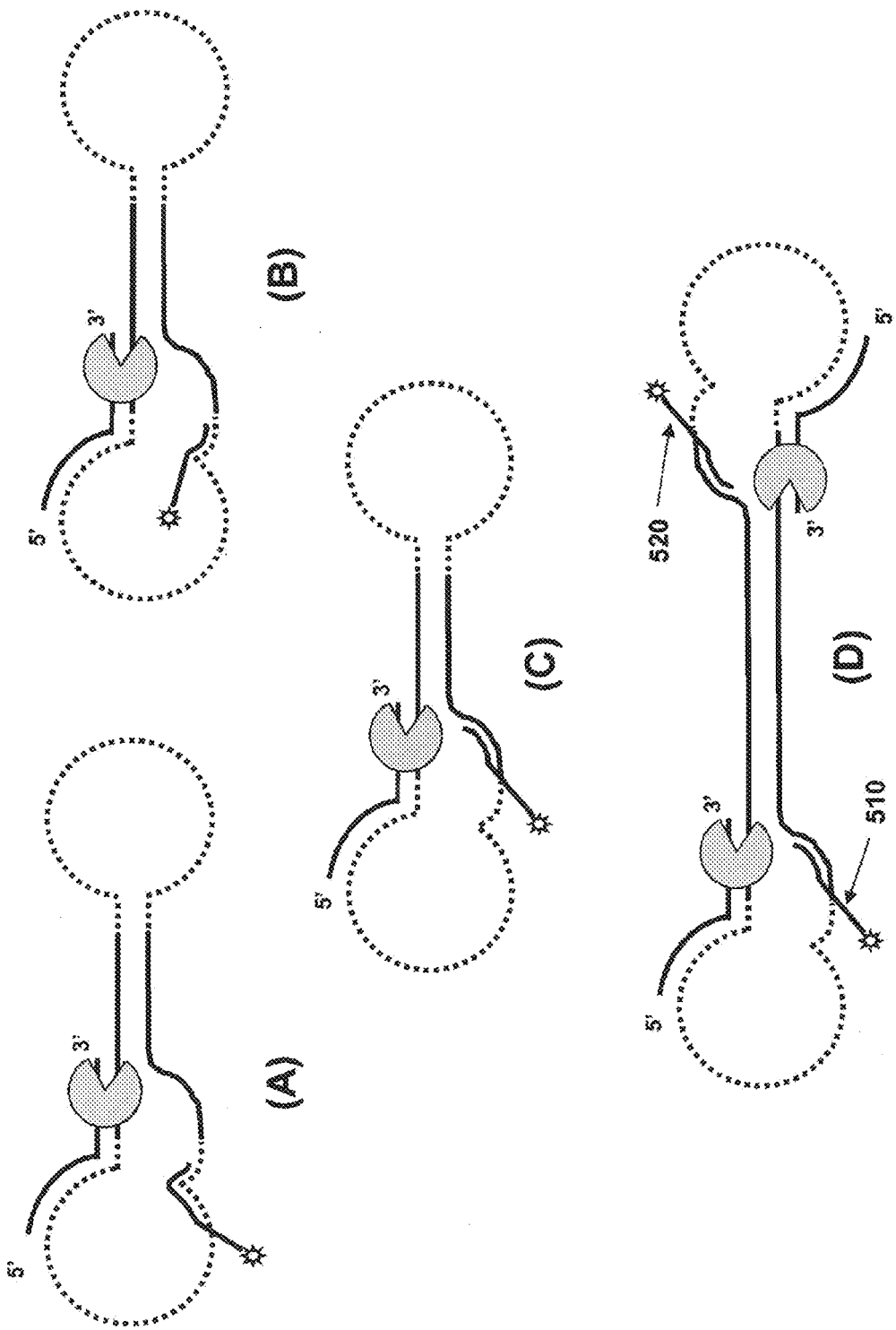
FIG. 5 illustrates regions of a template nucleic acid that can be targeted for capture by a hook molecule.

FIG. 5 illustrates how the hook capture region can be used to target different portions of the nucleic acid comprising the polymerase-nucleic acid complex. Each of FIGS. 5A-5D shows a polymerase-nucleic acid complex comprising a SMRTBell™ type template, in which the polymerase has walked in, producing a nascent strand extending into the formerly double stranded region of the nucleic acid. In FIG. 5A, a capture region is directed to a sequence that spans both the hairpin region and the formerly double-stranded region. This type of capture region is useful for universal capture of all of the active complexes in a mixture of nucleic acids. While a portion of the sequence to which the capture region is directed is in the single stranded region, the length of the capture region, e.g. capture oligonucleotide region, is designed such that hybridization to only the single stranded portion will not provide a tight enough interaction in order to capture the nucleic acid, requiring capture to an exposed double stranded region for removal or isolation.

In FIG. 5B, the capture portion of the hook molecule is directed only at the portion of the hairpin adaptor that was formerly double stranded. This approach can be taken where the double stranded region of the hairpin adaptor is long enough to provide a sequence having adequate binding for capture. In FIG. 5C, the capture portion of the hook molecule is directed to the portion of the nucleic acid from the double stranded fragment, and is not directed to the hairpin adaptor portion of the nucleic acid. This approach allows for the capture of only the nucleic acids within the mixture that contain the specific sequence to be captured. FIG. 5D illustrates that in some cases, multiple sequences within the double stranded region can be targeted. In FIG. 5D, hook oligonucleotide 510 is directed to a sequence on one strand of the fragment, and hook oligonucleotide 520 is directed to a sequence on the other strand of the fragment. In some cases, multiple hook oligonucleotides can be directed to different sequences on the same strand of the fragment. Multiple hooks can be used, for example, in a sequential manner, whereby one hook molecule is used to isolate nucleic acids having a given sequence, then a second hook molecule is used to isolate from that set of nucleic acids the nucleic acids having a second sequence. The polymerase-nucleic acid complexes isolated after this process will be those nucleic acids having both sequences of interest. This process can be extended beyond two sequences for the isolation of sequence having 3, 4, 5, or more sequences.

Once the active polymerase-nucleic acid complexes are attached to beads, we have found that these complexes can be bound onto a substrate directly by contacting the beads with the substrate or by bringing the beads into close proximity with the substrate. This approach allows for loading the complexes onto the substrate without going through a separate step of releasing the complexes from the beads into solution.

Figure 6:
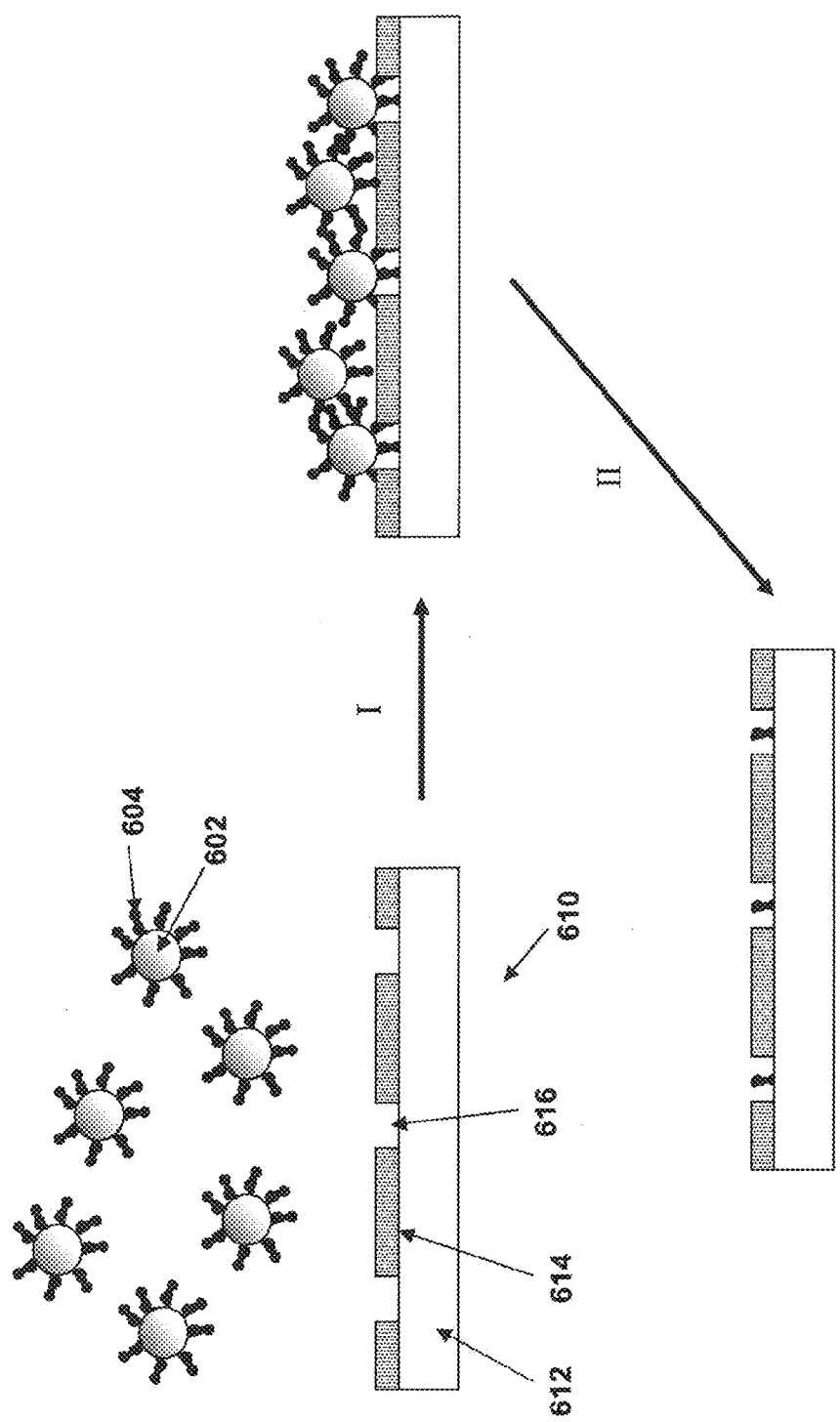
FIG. 6 shows a method of the invention for depositing molecules-of-interest such as polymerase-nucleic acid complexes onto substrates such as zero mode waveguide arrays.

FIG. 6 shows an embodiment of the invention for loading polymerase-nucleic acid complexes onto a substrate directly from beads. A substrate 610 is provided. The substrate will generally have coupling groups that will react with moieties on the polymerase-nucleic acid complexes to bind the complexes to the surface. In the embodiment of FIG. 6, the substrate comprises an array of nanoscale wells or zero mode waveguides 616. The zero mode waveguides 616 on substrate 610 are nanoscale apertures through a cladding layer 614 that has been deposited onto a transparent substrate 612. The thickness of the cladding layer is generally from about 10 nm to about 300 nm. The zero mode waveguides can be, for example, cylindrical holes having diameters from about 10 nm to about 300 nm. Such zero mode waveguide arrays can be used for single molecule analysis such as single molecule sequencing as described herein. The zero mode waveguide can be in any suitable shape including cylinders or cones. The shape can be a channel. The cross sectional shape of the zero mode waveguide can be a circle, a triangle, a square, a rectangle, or an ellipse, or the cross sectional shape can be an arbitrary shape. For performing analysis within zero mode waveguides it is often desirable to have immobilized molecules-of-interest bound to the base of the zero mode waveguide, but to have little to substantially no molecules-of-interest on other parts of the substrate. Methods for treating the surfaces of zero mode waveguides including methods for obtaining selective coupling to the base of the zero mode waveguides are described, for example, in U.S. Pat. Nos. 7,833,398, 7,292,742 and in U.S. patent application Ser. Nos. 11/731,748, filed Mar. 29, 2007, 12/079,922, filed Mar. 27, 2008, and 12/074,716, filed Mar. 5, 2008, the full disclosures of which are incorporated by reference herein for all purposes. In some cases, for example, biotin is selectively coupled to the base of the zero mode waveguide.

Onto the substrate is dispensed a solution of beads 602 having molecules-of-interest, e.g. polymerase-nucleic acid complexes 604 bound to them. The complexes will generally have a binding moiety that will attach to the coupling group deposited onto the substrate surface. For example, where the substrate comprises biotin coupling groups, a biotin binding protein can be bound to the polymerase-nucleic acid complex. The biotin binding protein can be, for example, streptavidin that is bound to the polymerase enzyme. These polymerase-nucleic acid complex coated beads can be made in any suitable manner. In some cases they are made using the hook molecule method described herein. The solution comprising the beads 602 is generally an aqueous solution having the components required for keeping the polymerase-nucleic acid complex together. The beads 602 can be magnetic beads. The size of the beads will depend on the application. In some cases, it is desirable that the beads have a diameter that is larger than the diameter of the zero mode waveguide.

In step (I), the beads are brought into contact with the substrate. This can be accomplished, for example, by applying a field that causes the beads to move down onto the top of the substrate. Where the beads are magnetic, a magnetic field can be used to draw the beads down. In addition to drawing the beads down, we have found that it can be desirable to provide a dynamic field that causes the beads to move across the top of the substrate. This can be accomplished, for example, by moving a permanent magnet under the substrate in a manner that causes the beads to move. One or more permanent magnets can be moved in a rotary fashion such that the beads are swept across the surface. In other cases, one or more fixed electromagnets provided with varying currents can be used to produce the dynamic field. In general, beads are referred to as magnetic beads where a magnetic field can be used to move the beads.

In step (II) the beads are removed from the substrate surface. Where magnetic beads are used, this removal or isolation can be performed by using magnets to the side and from above the sample.

We have found that this process can result in the attachment within the zero mode waveguides of polymerase-nucleic acid complexes. By using this process, we have found that we can achieve the same levels of loading as with diffusion loading of polymerase-nucleic acid complexes in solution with a much smaller amount of complex. We have seen equivalent loading levels for bead assisted loading using complex amounts in solution that are more than an order of magnitude less than for diffusion loading. The methods of the invention can similarly be used to attach other molecules-of-interest, for example biomolecules.

We have determined from these experiments that the attachment between the polymerase-nucleic acid complex and the bead is broken during the process, leaving the complex bound to the surface while the beads are removed. There can be several places where the break in the attachment of the complex to the bead can occur. One aspect of the invention is controlling the place at which the break occurs by designing into the construct linkages having appropriate levels of binding. Various types of linkages are possible, and some types have stronger binding than others. In some embodiments of the invention, a nucleic acid hybridization is used as the weakest link in the chain of binding. In some cases two or more hybridization linkages can occur in the chain of binding, and one can be made to be stronger than another, for example by having a longer region of sequence homology. The strength of the linkage can also be controlled by including modified or non-natural bases, e.g. peptide nucleic acids (PNAs), adding mismatched bases, and by changing the conditions in the solution including ionic strength and/or the temperature.

One example of controlling the position of the break in the linkage between the bead and the complex is provided where the polymerase enzyme is bound to the surface via a biotin-streptavidin linkage, the polymerase enzyme is bound to the nucleic acid by an enzyme-substrate interaction at the active site, the nucleic acid is bound to a hook oligonucleotide by hybridization with a capture sequence on the hook oligonucleotide to a sequence on a hairpin adaptor portion of the nucleotide of about 10 to about 15 base pairs, and the hook oligonucleotide is attached by hybridization from a retrieval region on the hook oligonucleotide of about 18 to about 30 nucleotides to an oligonucleotide attached to a magnetic bead, e.g. with a poly(dA) region on the hook oligonucleotide and a poly(dT) region on the magnetic bead. For this type of construct, we have determined that the hybridization linkage between the capture region of the hook and the nucleic acid is the weakest link that is most susceptible to breaking during the magnetic bead loading. Having breakage at this locus is advantageous, as it leaves the polymerase-nucleic acid complex on the surface without the hook or any portion of the bead attached to it. It is interesting to note that the binding between the polymerase and the nucleic acid is stronger than the oligonucleotide hybridization linkage under the appropriate conditions. We have found by labeling experiments that both the polymerase and the enzyme remain on the substrate, showing that this bond remains as the hook-oligonucleotide bond is broken.

The bead loading described herein can be used for loading of single copies of desired molecules into zero mode waveguides. In some cases, obtaining a substrate with a relatively high level of single molecules for observations can be accomplished using an appropriate level of dilution, and relying on a statistical distribution. For example, a sample can be diluted and loaded such that on average, some regions have no polymerase, some have a single polymerase, and some have multiple polymerases. This type of process results in loading levels that can be modeled as a Poisson distribution. This type of statistical loading can also be accomplished with the bead loading of the invention. The relative amount of active polymerase-nucleic acid complex bound to the beads can be varied by varying the concentration at which the beads are loaded. We have found that by loading beads at various concentrations, we can obtain a bead loading that provides numbers of single molecules on the substrate that are consistent with a Poisson distribution. We have found that the amount of material required to load polymerase-nucleic acid complexes onto a zero mode waveguide substrate for bead loading can be more than an order of magnitude less than required for solution loading.

Methods for Isolating Active Polymerase-Nucleic Acid Complexes

In some aspects the invention provides for methods and compositions for isolating active polymerase-nucleic acid complexes. Hook molecules such as hook oligonucleotides are used to capture and retrieve active polymerase-nucleic acid complexes by capturing one or more sequences that are exposed only after the action of the polymerase in the complex of opening up a double-stranded region to make the sequence available to the hook molecule. Isolating active complex from other components in the mixture can be useful for nucleic acid sequencing and particularly for single molecule sequencing. The complexes can be loaded onto a substrate such as a zero mode waveguide array for single molecule sequencing, and the methods of the invention allow for obtaining higher quality sequencing data by ensuring that a purer sample with a higher level of active complex is loaded onto the surface. In addition to isolating the active complexes, the methods can also be used to selectively isolate specific nucleic acids of interest.

The methods of the invention include a process comprising: first forming a polymerase-nucleic acid complex by mixing: (a) a polymerase enzyme comprising strand displacement activity, and (b) a nucleic acid comprising a double stranded portion comprising a first strand and a complementary second strand. The complex will generally have a priming site, to which the polymerase will tend to migrate. One or more primers can be added to form the priming site. Once the complex is formed, nucleic acid synthesis by the polymerase enzyme in the complex is initiated to produce a nascent strand complementary to the first strand. The synthesis of the nascent strand complementary to the first strand by the strand displacing enzyme results in the displacement a portion of the second strand. The amount of synthesis that occurs, that is, the number of bases that are added by the polymerase, is controlled by halting the nucleic acid synthesis in a controlled manner. This can be done, for example, by carrying out the nucleic acid synthesis under relatively slow, controlled conditions and stopping the synthesis at a specific time, by limiting the reagents such as the nucleotides, or by engineering stopping points into the nucleic acid. The conditions are selected such that the polymerase-nucleic acid complex is stable. A hook molecule such as a hook oligonucleotide is then added. The hook molecule has a capture region that is designed to specifically bind to a displaced portion of the second strand. In preferred embodiments the capture region comprises an oligonucleotide having a sequence that is complementary to a sequence in the displaced portion of the second strand. This hook molecule can be used to isolate the complex to which it is bound. The hook molecule can be either attached to a solid substrate or the hook molecule can have a retrieval portion that can be bound to a solid substrate in a subsequent step. The solid substrate can comprise, for example, beads, fibers, a planar substrate such as an oligonucleotide array, or column packing.

Methods for Isolating Nucleic Acid Complexes

In some aspects, the invention includes isolating polymerase enzyme-nucleic acid complexes from other components in the reaction mixture without using walk-in to expose the capture sequence. The same hook molecules or hook oligonucleotides can be used for methods that use walk-in and those that do not use walk-in. In some embodiments the invention comprises a method for isolating a polymerase-nucleic acid complex comprising first forming a polymerase-nucleic acid complex by mixing a polymerase enzyme with a nucleic acid having a single stranded portion and a double stranded portion. A hook molecule such as an oligonucleotide is then specifically attached to the complex, e.g. by hybridization through a capture region on the hook oligonucleotide that is targeted to the single stranded portion of the nucleic acid. Once the hook molecule is attached to the nucleic acid, the complex can be isolated using the hook oligonucleotide. For example, in some cases the hook molecule is a hook oligonucleotide that is attached to a bead. The bead can be isolated from solution to isolate the polymerase-nucleic acid complex from the reaction mixture. The bead can be, for example, a magnetic bead.

The hook oligonucleotide used can be attached to a bead, allowing for direct removal or isolation of the complex. In other cases, the hook oligonucleotide can have a retrieval region that is complementary to an oligonucleotide sequence attached to the bead, allowing for indirect removal or isolation. The design of the primers is carried out to control the binding strength of the various regions. For example, in some cases a bead having a poly nucleotide, such as a poly-A tail, is used, and the hook oligonucleotide has a poly(T) region and a capture region complementary to the single stranded portion of the nucleic acid. The poly(T) region is typically designed to be stable enough for removal or isolation, but generally less stable than the binding of the capture region to the oligonucleotide. For example, in some cases, the poly(T) region ranges from about 12 to about 30 nucleotides, or from about 15 to about 25 nucleotides or from about 16 to about 21 nucleotides in length. The strength of the capture region is generally designed to be stronger than the binding of the retrieval region. In some cases groups that can enhance hybridization stability such as LNAs, PNAs or methoxy groups are used. In some cases, a "splint" oligonucleotide is used which has two binding segments, one that binds to a retrieval sequence on the hook oligonucleotide, and the other that binds to the retrieval sequence on the bead.

The invention can be used for producing and purifying complexes from a mixture of DNA fragments, for example as used in sequencing. The method can entail first fragmenting a double stranded DNA sample into double stranded fragments, then ligating to each end of the double stranded fragments a hairpin to produce a population of circular DNA templates having a central double stranded region and hairpin regions on each end. The hairpin regions on each end are single stranded regions that can be used for both priming and capture. The population of circular DNA templates are exposed to a primer complementary to the single-stranded portion of a hairpin region of the template and to a DNA polymerase enzyme having strand displacement activity. One can then add to the population of complexes a hook oligonucleotide comprising a capture region complementary to a portion of the hairpin region, and use the hook oligonucleotide to isolate the complexes to which it hybridized. This allows for isolating complexes from the mixture.

Polymerase-Nucleic Acid Complex

While many enzyme-substrate interactions are transient, some polymerase enzymes can form relatively stable complexes with nucleic acids that can be manipulated, purified, and then subsequently used to carry out nucleic acid synthesis. For example, DNA polymerases having relatively high processivity can have strong associations with template nucleic acid molecules. An exemplary DNA Polymerase is phi-29 DNA polymerase. Methods for forming and manipulating polymerase-nucleic acid complexes are described, for example in copending U.S. patent application entitled Purified Extended Polymerase/Template Complex for Sequencing" 61/385,376, filed Sep. 22, 2010 which is incorporated by reference herein in its entirety for all purposes. The current invention describes ways in which these complexes can be treated in order to isolate a portion of the complexes that have desired properties.

The polymerase-nucleic acid complex will have a polymerase and a nucleic acid having a double stranded region. The polymerase-nucleic acid complex will generally also have a primer from which a nascent nucleic acid strand will be produced complementary to a template strand of the nucleic acid. The primer is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC-rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. In some cases, the primer is added as a separate component to form the complex; in other cases, the primer can be part of the nucleic acid that used. For example, in some cases priming can begin at a nick or a gap in one strand of a double-stranded nucleic acid.

The polymerase-nucleic acid complex has a nucleic acid that acts as the template for nucleic acid synthesis. The nucleic acids that comprise the complex have at least a portion that is double stranded. One of the two strands will act as the template strand for which the polymerase will produce a complementary nascent nucleic acid strand. The other strand in the double stranded region will be displaced by the strand displacement activity of the polymerase enzyme. In some cases, the template strand of the nucleic acid will have a single stranded portion that is upstream of the double stranded region. Where this is the case a primer can be added to hybridize to the single stranded portion, and nucleic acid synthesis can proceed from the primer into the downstream double stranded region.

The template nucleic acid can be derived from any suitable natural or synthetic source. In preferred embodiments, the template comprises double stranded DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can comprise a library of double stranded segments of DNA. The template nucleic acid can be linear or circular. For example, the nucleic acid can be topologically circular and have a linear double stranded region. A circular nucleic acid can be, for example, a gapped plasmid. In some embodiments the nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end—ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

The terms "nucleic acid" or "oligonucleotide" or grammatical equivalents herein mean at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008. Alternate functional circular constructs are also described in U.S. patent application Ser. No. 12/383,855, filed Mar. 27, 2009, and U.S. patent application Ser. No. 12/413,258 filed Mar. 27, 2009, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions that are common to all of the nucleic acids in the population and also have specific regions that are different in the different members of the population. The current invention allows for capturing and isolating polymerase-nucleic acid complexes using either the universal or the specific regions.

While in many cases nucleic acid synthesis is describe herein as extending from a primer, it is to be understood that some polymerases do not require an added external primer, and can be initiated using terminal protein. Polymerases that can be initiated using terminal protein include phi-29 polymerase.

Use of Active Polymerase to Release the Hook Molecule

An alternative implementation of the invention allows for using the hook oligonucleotide to select for inactive rather than active complexes. For example, the hairpin region of a circular template molecule having hairpin regions on each end can have two different sites on it; one that is complementary to a primer, and downstream of that site, a site that will be captured by a hook oligonucleotide. The template DNA, which can be a library of fragments is treated with both the prime and the hook oligonucleotide. The hook oligonucleotide is complementary at its 5' end, and has a retrieval segment that is not complementary at its 3' end. Polymerase is then added, and the polymerization is carried out such that the DNA synthesis continues for some number of bases. The complexes that are active will displace the hook oligonucleotide, but the complexes that are not active will still have the hook oligonucleotide hybridized to them. The hook oligonucleotides can then be isolated or removed from solution using their retrieval region, for example, with beads such as magnetic beads. Alternatively, the retrieval region of the hook oligonucleotides can comprise a bead.

Polymerase Enzymes

Polymerase enzymes useful in the invention include polymerases mutated to have desirable properties for sequencing. For example, suitable enzymes include those taught in, e.g., WO 2007/076057 POLYMERASES FOR NUCLEOTIDE ANALOGUE INCORPORATION by Hanzel et al., WO 2008/051530 POLYMERASE ENZYMES AND REAGENTS FOR ENHANCED NUCLEIC ACID SEQUENCING by Rank et al., and U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES." The modified polymerases may have modified properties such as e.g., decreased branch fraction formation, improved specificity, improved processivity, altered rates, improved retention time, improved stability of the closed complex, etc.

In addition, the polymerases can be further modified for application-specific reasons, such as to increase photostability, e.g., as taught in U.S. patent application Ser. No. 12/384, 110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

The polymerase enzymes used in the invention will generally have strand-displacement activity. Many polymerases have this capability, and it is useful in the context of the current invention for opening up and exposing the regions of a nucleic acid sample for capture by a hook molecule. In some cases, strand displacement is part of the polymerase enzyme itself. In other cases, other cofactors or co-enzymes can be added to provide the strand displacement capability.

DNA Polymerases

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/ xeroderma pigmentosum variant (class Y). For a review of recent nomenclature, see, e.g., Burgers et al. (2001) "Eukaryotic DNA polymerases: proposal for a revised nomenclature" J Biol. Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. Nos. 12/924,701, filed Sep. 30, 2010; and 12/384,112, filed Mar. 30, 2009.

RNA Polymerases

In some embodiments, the polymerase enzyme that is used for sequencing is an RNA polymerase. Any suitable RNA polymerase (RNAP) can be used including RNA polymerases from bacteria, eukaryotes, viruses, or archea. Suitable RNA polymerases include RNA PoI I, RNA PoI II, RNA PoI III, RNA PoI IV, RNA PoI V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e., they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Initiation of Synthesis/Halting Synthesis

In order to obtain the polymerase-nucleic acid complex comprising the exposed portion for capture, it is generally required that the initiation and the halting of the polymerase reaction be controlled. For example, the formation of the nucleic acid-polymerase-nucleic acid complex can be carried out in a medium having ionic metals that prevent or inhibit synthesis. For example, Sr and or Ca can be present in concentrations in which the polymerase is either inactive or only barely active. The level of catalytic metals such as Mg and Mn can also be kept relatively low to minimize the amount of nucleic acid synthesis. While initiation can also be controlled by manipulating the amount and type of nucleotide or nucleotide analog, we have found that the complex is generally more stable in the presence of nucleotides or nucleotide analogs. Other conditions such as the temperature and the pH can be used to minimize polymerization during complex formation.

Once the complex is formed, polymerization can be initiated. Initiation can be done by any suitable method. In some cases, the polymerase reaction can be initiated simply by adding the appropriate reagents for nucleic acid synthesis at the appropriate temperature and pH. Other suitable methods, such as raising the temperature, for example, to initiate synthesis by a hot-start enzyme can be used.

In order to provide an exposed region in an intact complex, it is generally required that the polymerase reaction be halted in a controlled fashion. It is generally desired that the polymerase only proceed to past the point where the sequence to be captured is exposed, and then stop. It is also desired that the method of halting the polymerase keep the polymerase-nucleic acid complex intact so that it can be used for the subsequent steps of the method.

One method of stopping the enzyme in a controllable fashion is to carry out polymerization for a specific period of time under controlled conditions, at which point the enzyme synthesis activity is halted. The controlled conditions will usually involve controlling reaction conditions such that the polymerase performs synthesis more slowly than it is capable of. Slowing and controlling the enzyme can be done, for example, by adding a non-catalytic metal such as Ca. In some cases, only Ca is added as a divalent metal. We have found that nucleic acid synthesis can occur slowly without the explicit addition of catalytic metals. In some cases, an appropriate ratio of catalytic to non-catalytic divalent cation will be provided to obtain the desired rate. The ratio of Ca to Mg or Mn can be from about 10 to about 200, from about 3 to about 1000, or from about 1 to about 10000.

One method of halting the reaction is to add a reagent that causes the enzyme to stop polymerizing, but keeps the enzyme intact for further polymerization. A preferred reagent for halting the polymerase is Sr. We have found that by adding Sr at the appropriate concentration, the polymerase reaction can be reversibly halted. The concentration of Sr to halt the polymerase can be, for example, from about 0.2 mM to about 20 mM, from about 0.01 mM to about 100 mM, or from about 1 nM to about 0.5 M.

The time between initiation and halting can be from on the order of seconds to on the order of days. Where the reaction time is fast, on the order of seconds, it can be more difficult to control the initiation and termination throughout the volume of the reaction. Where the reaction time is multiple hours, there is the disadvantage of having to wait a long time. Therefore, reaction times from about 10 seconds to about 4 hours, about 30 seconds to about 2 hours, or about 1 minute to about 30 minutes are desirable.

A method of halting the polymerase reaction is to add reagents which bind the catalytic metal. It is known, for example, that a chelating agent such as EDTA can complex with the catalytic divalent cations to halt the reaction. Chelating agents must be used with care, as if the divalent cations are complexed too effectively, it can result in a destabilization of the polymerase-nucleic acid complex. The reaction can also be halted by changing the conditions, such as the temperature and the pH in a manner that halts enzyme polymerization. As with chelating agents these halting methods must be carried out with care so as not to damage the polymerase-nucleic acid complex, e.g. by denaturing the enzyme. For example, lowering of the temperature can be used to halt the reaction reversibly either alone or in combination with other methods.

In some cases, halting can be accomplished by providing only a limiting amount of reagents for the synthesis reaction. For example, the nucleotide or nucleotide analog can be provided at an amount such that the reaction runs out or slows down significantly as the desired amount of walk-in is reached.

The halting of the nucleic acid reaction can also be accomplished by providing blocking groups on the nucleic acid that is being copied by the polymerase. The blocking groups can be used to stop the polymerase at a specific point, providing for control of exactly how much of the nucleic acid is exposed. Generally, the blocking groups create a reversible stopping or pausing point, allowing the complex to be re-initiated for nucleic acid synthesis after the purification by the hook molecule. The stopping points may comprise elements such as large photolabile groups, strand-binding moieties, non-native bases, and others.

One may optionally employ various means for controlling initiation and/or progression of a sequencing reaction, and such means may include the addition of specific sequences or other moieties into the template nucleic acid, such as binding sites, e.g., for primers or proteins. Various methods of incorporating control elements into an analytical reaction, e.g. by integrating stop or pause points into a template, are discussed elsewhere herein and are further described in related applications, U.S. application Ser. No. 12/413,258, filed Mar. 27, 2009, and U.S. application Ser. No. 12/982,029, filed Dec. 30, 2010 which are incorporated herein by reference in their entirety for all purposes.

Figure 7:
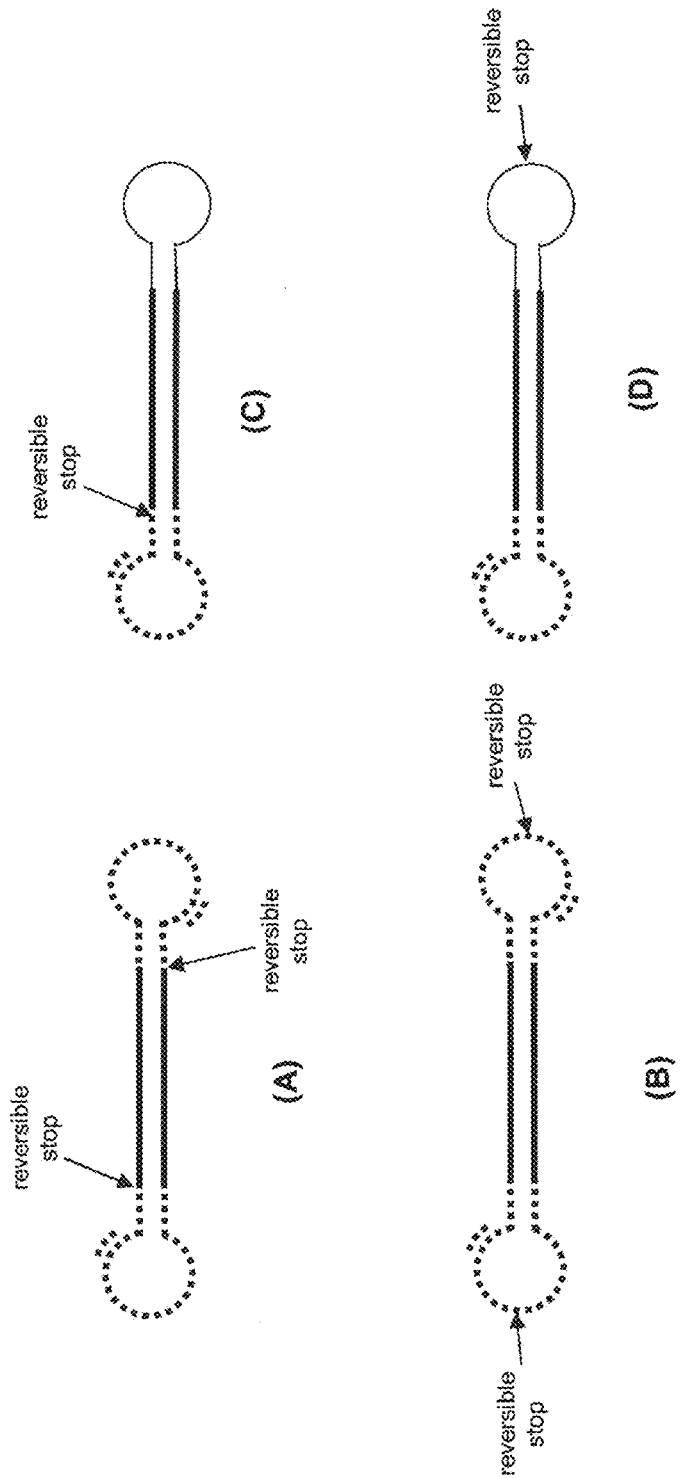

In certain embodiments, a reaction stop or pause point may be included within the template sequence, such as a reversibly bound blocking group at one location on the template, e.g., on the linking portion that was not used in priming. The stop or pause point can be incorporated into either a single stranded or double stranded portion of the nucleic acid template. Where SMRTBell™ type template nucleic acids are used, the pause point can be either in a hairpin linker region or in the double-stranded central portion. In some embodiments it is useful to have the stop or pause point within the hairpin region. FIG. 7 illustrates several approaches for the inclusion of stop or pause points. In FIG. 7(A), a library of templates is produced by fractionating a double stranded DNA sample into a population of double stranded segments, and hairpin loops are hybridized onto each end. In this embodiment, a single hairpin loop having a universal priming site is used, such that each end of the template nucleic acid has an identical hairpin loop. A reversible stop is included in the construction of the hairpin loop part way into the double stranded region, allowing a polymerase, that initiates at the primer to proceed into the template nucleic acid, creating a nascent strand which displaces the complementary strand, exposing a sequence that can bee used for capture by the hook. Here, the stop or pause point is placed downstream of the priming site such that the polymerase will pause while it is copying the hairpin adaptor, and before it reaches the portion of the nucleic acid that is derived from the sample nucleic acid which was fragmented. Once capture and isolation are performed, the reversible stop or pause can be removed to allow the enzyme to continue synthesizing the nucleic acid template. This embodiment can be useful where a universal capture region on the hook is used to capture all active complexes regardless of the sequence in the central region.

FIG. 7(B) shows an alternative embodiment in which the reversible stop is positioned up-stream from the priming site, such that the polymerase will pass through the central section and proceed into the hairpin loop on the other side before being halted. This approach can be employed when a specific sequence within the fragmented double stranded portion is targeted for capture.

FIG. 7(C) shows a construction similar to that in FIG. 7(A), but in which the SMRTBell™ templates have a different hairpin adaptor on each end. The hairpin adaptor region comprising the reversible stop also has a priming region. The hairpin adaptor at the other end of the construct has no priming site. This type of construction can be used where it is desired that only one enzyme bind per template nucleic acid.

FIG. 7(D) is a construct that is similar to that of FIG. 7(B) except that each end of the SMRTBell™ template has a different hairpin adaptor. Here, one of the hairpin adaptors has a priming region, and the other hairpin adaptor has a reversible stop. This type of construction can be used where it is desired that only one enzyme bind per template nucleic acid. Techniques for producing SMRTBell™ type templates having different adaptors at each end are described, for example, in U.S. patent application Ser. No. 12/413,258, filed Mar. 27, 2009, the disclosure of which is incorporated by reference herein for all purposes.

A variety of synthesis controlling groups may be employed as stop or pause points, including, e.g., large photolabile groups coupled to the nucleobase portion of one or more bases in the single-stranded portion that inhibit polymerase-mediated replication; strand-binding moieties that prevent processive synthesis; non-native nucleotides included within the primer and/or template; and the like. The use of strand-binding moieties includes, but is not limited to, reversible, specific binding of particular proteins to recognition sequences incorporated into the template (or primer bound thereto) for this purpose. In certain embodiments, such control sequences may include binding sites for transcription factors, e.g., repressor binding regions provided within the linking portion(s). For example, the lac repressor recognition sequence is bound by the lac repressor protein, and this binding has been shown to block replication in a manner reversible by addition of appropriate initiators, such as isophenylthiogalactoside (IPTG) or allolactose.

In some embodiments, primer recognition sequences and/or additional control sequences may also be provided for control of initiation and/or progression of polymerization, e.g., through a hybridized probe or reversibly modified nucleotide, or the like. (See, e.g., U.S. Patent Application No. 2008-0009007, the full disclosure of which is incorporated herein by reference in its entirety for all purposes.) Such probes include but are not limited to probes at which a polymerase initiates polymerization, probes containing various types of detectable labels, molecular beacons, TaqMan® probes, Invader® probes (Third Wave Technologies, Inc.), or the like, that can be used for various purposes, e.g., to provide indications of the commencement and/or progress of synthesis.

An engineered pause point (reversible or irreversible) can include one or more non-native (non-natural) or fifth bases that do not pair with any of the four native nucleoside polyphosphates in the synthesis reaction, e.g., in the template and/or oligonucleotide probe(s), and/or that exhibit a distinct kinetic signature during template-dependent synthesis at such a base. Upon encountering such a base, the polymerase pauses until the complement to the non-natural base is added to the reaction mixture. Likewise, an engineered pause point could include a "damaged" base that causes a stop in replication until repair enzymes are added to the mixture. For example, a template having a pyrimidine dimer would cause the replication complex to pause, and addition of the photolyase DNA repair enzyme would repair the problem location and allow replication, and sequencing to continue. In yet further embodiments, a combination of modification enzymes could be used to engineer a set of modified bases on a template, e.g., a combination of glycosylases, methylases, nucleases, and the like. (Further information on sequencing template nucleic acids comprising modifications, including detecting kinetic signatures of such modifications during single-molecule sequencing reactions, are provided in U.S. Patent Application Nos. 61/201,551, filed Dec. 11, 2008; 61/180,350, filed May 21, 2009; and 12/945,767, filed Nov. 12, 2010; and U.S. Patent Publication No. 2010/0221716, the disclosures of which are incorporated herein by reference in their entireties for all purposes.)

As noted elsewhere herein, stop or pause points can be engineered into various portions of the template, e.g., portions for which the nucleotide sequence is unknown (e.g., a genomic fragment) or known (e.g., an adaptor or linker ligated to the genomic fragment.) For example, SMRTbell™ templates are topologically closed, single-stranded molecules having regions of internal complementarity separated by hairpin or stem-loop linkers, such that hybridization of the regions of internal complementarity produces a double-stranded portion within the template. One or both of the linkers can comprise a stop or pause point to modulate polymerase activity. In some embodiments, these regulatory sequences or sites cause a permanent cessation of nascent strand synthesis, and in other embodiments the reaction can be reinitiated, e.g., by removing a blocking moiety or adding a missing reaction component. Various types of pause and stop points are described below and elsewhere herein, and it will be understood that these can be used independently or in combination, e.g., in the same template molecule.

In other embodiments, an abasic site is used as a synthesis blocking moiety or pause point until addition of a non-natural "base," such as a pyrene, which has been shown to "base-pair" with an abasic site during DNA synthesis. (See, e.g., Matray, et al. (1999) Nature 399(6737):704-8, which is incorporated herein by reference in its entirety for all purposes.) Where a permanent termination of sequencing is desired, no non-natural analog is added and the polymerase is permanently blocked at the abasic site. DNA (or RNA) glycosylases create abasic sites that are quite different from the normal coding bases, A, T, G, and C (and U in RNA). A wide variety of monofunctional and bifunctional DNA glycosylases that have specificity for most common DNA or RNA adducts, including 5-methylcytosine, are known in the art, with different glycosylases capable of recognizing different types of modified DNA and/or RNA bases. The molecular structures of many glycosylases have been solved, and based on structural similarity they are grouped into four superfamilies. The UDG and AAG families contain small, compact glycosylases, whereas the MutM/Fpg and HhH-GPD families comprise larger enzymes with multiple domains. As an example, four enzymes have been identified in *Arabidopsis thaliana* in the plant pathway for cytosine demethylation. Additionally, other enzymes are also known to recognize 5-methyl cytosine and remove the methylated base to create an abasic site. Further, various enzymes are known to methylate cytosine in a sequence-specific manner. As such, a combination of a cytosine-methylase and an enzyme that creates an abasic site from a methylated cytosine nucleotide can be used to create one or more abasic sites in a template nucleic acid. The size of the recognition site of the methylase and the base composition of the template determine how frequently methylation occurs, and therefore the number of abasic sites created in a given template nucleic acid, allowing the ordinary practitioner to choose a methylase with a recognition site that produces a desired spacing between modified nucleotides. For example, if the recognition site is three bases long, then on average an abasic site is expected every 64 bases; if the recognition site is four bases long, then on average an abasic site is expected every 256 bases; if the recognition site is six bases long, then on average an abasic site is expected every 4096 bases; and so forth. Of course, templates with a higher GC content would be expected to have more frequent abasic site formation, and templates with lower GC content would be expected to have less frequent abasic site formation.

Uracil-DNA glycosylases can also be used to introduce abasic sites into a template nucleic acid comprising deoxyuridine nucleotides. This strategy has the advantage of allowing the practitioner to choose the locations of the abasic sites within a DNA template since deoxyuridine nucleotides are not generally found in DNA. Various methods of inserting deoxyuridine nucleotides into a DNA template may be used, and different methods will be preferred for different applications. In certain embodiments, one or more site-specific deoxyuracils are incorporated during standard phosphoramidite oligonucleotide synthesis. To place uracils at indeterminate positions in a DNA, replacing a portion of the deoxythymidine triphosphate with deoxyuridine triphosphate will result in an amplimer with random U sites in place of T sites after polymerase chain reaction. In other embodiments, deoxyuridine nucleotides are engineered into the template, e.g., by ligation of a synthetic linker or adaptor comprising one or more deoxyuridine nucleotides to a nucleic acid sequence to be sequenced. In certain preferred embodiments, deoxyuridine nucleotides are incorporated into the linker portions of a SMRTbell™ template.

To subsequently introduce abasic sites prior to sequencing, the deoxyuridine nucleotide-containing template is subjected to treatment with uracil-DNA glycosylase, which removes the one or more uracil bases from the deoxyuridine nucleotides, thereby generating one or more abasic sites in the template. Alternatively, since the deoxyuridine nucleotide can be recognized as a template base and paired with deoxyadenosine during template-dependent nascent strand synthesis, the synthesis-blocking abasic site can instead be introduced after initiation of the sequencing reaction, e.g., at a time chosen by the practitioner. For example, the reaction can be initiated with a deoxyuridine-containing template, and uracil-DNA glycosylase can subsequently be added to block the polymerase and halt the reaction after the reaction has proceeded for a given time. As such, termination of the reaction is optional rather than required.

While uracil-DNA glycosylase activity is useful for introducing abasic sites into a template as described above, this activity can be problematic during the preparation of such templates. As such, strategies are typically implemented during preparation and manipulation of uracil-containing DNA, e.g., using molecular biology enzymes, to avoid uracil-DNA glycosylase activity, in particular, due to the *E. coli* UDG enzyme. Since a majority of standard molecular biology enzymes are overexpressed and subsequently purified from an *E. coli* host, UDG activity can be a contaminating activity that is often not monitored by the enzyme manufacturer's quality control procedures. To mitigate contaminating UDG activity, a commercially available UDG inhibitor, also known as uracil glycosylase inhibitor or UGI (e.g., from New England Biolabs, Ipswich, Mass.) can be included in molecular biology reactions. This is a small protein inhibitor from the *B. subtilis* bacteriophage PBS 1 that binds reversibly to *E. coli* UDG to inhibit its catalytic activity. UGI is also capable of dissociating UDG from a DNA molecule. Alternatively, UDG activity can be inhibited without exogenous protein using a chemical inhibitor of the enzyme, such as an oligonucleotide containing a 1-aza-deoxyribose base, a transition state analog for the UDG enzyme. This and other cationic nitrogenous sugars have been used for mechanistic studies of UDG activity and show potent inhibition activity. (See, e.g., Jiang et al. Biochemistry, 2002, 41 (22), pp 7116-7124.)

In certain applications, UDG activity needs to be inhibited temporarily, and subsequently enabled to remove create an abasic site as described above. In some embodiments, a DNA purification that removes proteins is employed, e.g., including a phenol-chloroform extraction with subsequent ethanol precipitation, a silica-based column approach (e.g., QiaQuick columns from Qiagen and similar products), and/or a PEG/ sodium chloride precipitation (e.g., AMPure beads from Beckman Coulter). Alternatively or additionally, a commercially-available UDG enzyme that is not inhibited by UGI is added when abasic site formation is desired. For example, the *A. fulgidus* UDG is from a thermophilic organism and cannot be inhibited by the same bacteriophage protein as is the *E. coli* UDG enzyme. In certain preferred embodiments, UDG inhibition is employed during template preparation, and inhibition-resistant UDG activity is added at a subsequent time to trigger the creation of abasic sites at deoxyuridine nucleotides, e.g., immediately prior to or during an ongoing reaction.

In some embodiments, one or more abasic sites are engineered into a linker or adapter sequence within a sequencing template molecule. Abasic sugar residues serve as efficient terminators of polymerization for many polymerases, e.g., Φ29. 1',2'-dideoxyribose is the most common synthetic "abasic site". In other embodiments, a synthetic linker is incorporated into a linker or adaptor. For example, an internal spacer (e.g., Spacer 3 from Biosearch Technologies, Inc.) or other carbon-based linker can be used in lieu of a sugar-base nucleotide. Similar to an abasic nucleotide, the polymerase will be blocked upon encountering these moieties in the template nucleic acid.

In certain embodiments, synthesis blocking moieties used for stop or pause points are nicks in the template nucleic acid. Nicking enzymes (e.g., nicking endonucleases) are known in the art and can be used to specifically nick the template prior to or during a template-directed sequencing reaction. The use of site-specific nicking endonucleases allows the practitioner to incorporate a recognition sequence at a particular location within the template nucleic acid, and such nicking endonucleases are commercially available, e.g., from New England Biolabs, Inc. For example, a linker or adapter can be synthesized with a nicking endonuclease recognition sequence, ligated to a nucleic acid molecule to be sequenced, and can be specifically nicked either before or during a subsequent sequencing reaction. Nicks can also be introduced by ligating duplex segments that lack either a terminal 3'-hydroxy (e.g., have a dideoxynucleotide at the 3'-terminus) and/or 5'-phosphate group on one strand. The ligation results in covalent linkage of the phosphodiester backbone on one strand, but not on the other, which is therefore effectively "nicked." In certain embodiments, a SMRTbell™ template is constructed using a duplex (or "insert") nucleic acid molecule lacking a 5'-phosphate group at one or both termini. Upon ligation of the hairpin or stem-loop adaptors at each end, nicks are created at one or both ligation site(s), depending on whether the duplex lacked a 5'-phosphate at one or both ends, respectively. In other embodiments, a SMRTbell™ template is constructed using one or two stem-loop adaptors lacking a 3'-hydroxy group at the terminus (e.g., comprising a 2',3'-dideoxynucleotide rather than a 2'-deoxynucleotide). Upon ligation of one or two stem-loop adaptors lacking a 3'-hydroxy group, one or two nicks are created at the ligation site(s), depending on whether one or two adaptors lacked the 3'-hydroxy group, respectively. In both cases, a nick is created in the template nucleic acid, and a primer bound to one of the adaptors provides an initiation site for the polymerase, which will process the template until encountering a nick, at which point the polymerase will terminate the reaction by dissociation from the template. Regardless of how a nick is created, the position of a nick relative to the initiation site for the polymerase determines how much of the template will be sequenced.

In certain embodiments using ligation-based technologies (e.g., the SOLiD™ System developed by Life Technologies), a pause site can be engineered by using an oligonucleotide that cannot participate in the ligation reaction and that is complementary to a desired location on the set of identical template nucleic acids, e.g., on a bead. When the serial ligation reaction hits the position recognized by this polynucleotide, the reaction cannot proceed and any reactions that have become asynchronous will "catch up." The user can then unblock the oligo (e.g., using chemical treatment or photocleavage) and reinitiate the sequencing reaction.

In some cases, it may be desirable to provide endonuclease recognition sites within the template nucleic acid. For example, inclusion of such sites within a circular template can allow for a mechanism to release the template from a synthesis reaction, i.e., by linearizing it, and allowing the polymerase to run off the linear template, and/or to expose the template to exonuclease activity, and thus terminate synthesis through removal or isolation of the template. Such sites could additionally be exploited as control sequences by providing specific binding locations for endonucleases engineered to lack cleavage activity, but retain sequence specific binding, and could therefore be used to block progression of the polymerase enzyme on a template nucleic acid.

In some cases, nicking sites, e.g., sites recognized by nicking endonucleases, may be included within a portion of the template molecule, and particularly within a double-stranded portion of the template, e.g., in a double-stranded segment of a SMRT bell™ or in the stem portion of an exogenous hairpin structure. Such nicking sites provide one or more breaks in one strand of a double-stranded sequence and can thereby provide one or more priming locations for, e.g., a strand-displacing polymerase enzyme. A variety of nicking enzymes and their recognition sequences are known in the art, with such enzymes being generally commercially available, e.g., from New England Biolabs.

Another approach for controlling the amount of walk-in is to provide a walk-in sequence in the template nucleotide made up of fewer than the four types of nucleotides, and adding only the nucleotides required for filling out that sequence. When the polymerase reaction encounters the base for which no corresponding nucleotide has been added, the polymerase reaction will stop. After isolation of the active complex, the polymerase reaction can be resumed using a reaction medium having the required nucleotides for extension. For example, a region of the template strand portion of the template nucleic acid can be made using A, T, and G bases, then following this portion, a region will have one or more C's. The primer extension reaction is carried out using nucleotides T, A, and C, but without a G nucleotide. The extension reaction proceeds until the polymerase reaches the position having the C bases. Since no G nucleotide is present, the polymerase stops at that position. This strategy can be carried out using a sequence of three bases as described above, or may be carried out with two bases or even with a sequence of one base.

The number of nucleotides in the double stranded region used for walk in can vary from several nucleotides to thousands of nucleotides. In the case of performing universal capture, and capturing a sequence within the double stranded portion of a hairpin adaptor, walk-in can be on average from about 5 nucleotides to about 1,000 nucleotides or from about 10 nucleotides to about 200 nucleotides, or in some cases between 10 nucleotides and 100 nucleotides. In the case of performing specific capture, the walk-in can be on average from about 20 to about 100,000 nucleotides, from about 50 to about 10,000 nucleotides, or from about 100 to about 1000 nucleotides.

The Hook Molecule

Once the polymerase has walked-in the desired distance into the double-stranded region and the polymerase reaction is halted, a hook molecule is added in order to capture the desired active complexes in the reaction mixture. The hook molecule has at least two portions or regions, a capture region and a retrieve (or retrieval) region. The capture region is designed to capture a specific sequence in the template nucleic acid which is exposed by the action of a polymerase enzyme. The retrieve region allows the hook molecule to be removed from other components of the mixture along with the complex it has captured. The capture region can be directly connected to the retrieval region, or the hook molecule can have an intermediate region connecting the capture and retrieval portions.

In preferred embodiments, the capture region comprises an oligonucleotide with a region complementary to the sequence on the template nucleic acid that is exposed by the action of the polymerase. Where a capture oligonucleotide is used, the length of the capture region can vary depending on the application. It is well known that the strength and selectivity of binding of complementary or partly complementary oligonucleotides can be controlled by controlling the stringency of the medium, including the ionic strength of the solution and the temperature. The capture region will generally be designed both to have efficient and specific binding, and also such that the binding is reversible, allowing for separation of the hook from the nucleotide after isolation. In some cases the length of the capture oligonucleotide on the hook is from about 4 to about 100 nucleotides, from about 6 to about 50 nucleotides, or from about 8 to about 25 nucleotides in length. A capture oligonucleotide can comprise non-natural nucleotide units, e.g. PNA.

The capture region can also comprise other suitable molecules that specifically bind to an exposed sequence on the nucleic acid. For example, the capture region can comprise transcription factors, histones, antibodies, nucleic acid binding proteins, and nucleic acid binding agents, etc., that will bind to a specific sequence. See, e.g. Blackwell et al. Science 23 Nov. 1990:Vol. 250, 1149-1151 and Kadonaga et al. PNAS, 83, 5889-5893, 1986, and Ren et at. Science, 290, 2306-2309, 2000. The capture region can comprise an antibody that is designed to attach to a specific sequence. For antibodies that recognize specific nucleic acid sequences, see, for example LeBlanc et al., Biochemistry, 1998, 37 (17), pp 6015-6022. In some cases, the capture region can comprise agents that will specifically bind regions of the template nucleic acid template that have modified or unnatural nucleotide. For example, a antibodies against 5-MeC are used to enrich for methylated DNA sequences (See, e.g. M. Weber, et al., Nat. Genet. 2005, 37, 853, incorporated herein by reference in its entirety for all purposes). In certain embodiments, the modification is an 8-oxoG lesion and/or the agent is a protein is selected from the group consisting of hOGG1, FPG, yOGG1, AlkA, Nth, Nei, MutY, UDG, SMUG, TDG, or NEIL. In other embodiments, the modification is a methylated base and/or the agent is a protein selected from the group consisting of MECP2, MBD1, MBD2, MBD4, and UHRF1. Specific binding is described also in U.S. patent application Ser. No. 12/945,767, filed Nov. 12, 2010.

In some cases, a single type of hook molecule comprising a single type of capture region is added to a mixture of polymerase complexes. This is done, for example, where a universal capture region, e.g. on a hairpin adaptor, used for isolating active polymerase-nucleic acid complexes from inactive complexes regardless of sequence. In some cases, a mixture of types of hook molecules is used in which each type of hook molecule has a capture region directed at a different sequence. The mixtures of hook molecules are generally used for isolating nucleic acids having specific sequences from a population of nucleic acids that do not contain such sequences. This method could be directed to pulling down all conserved sequences of genes from a genetic pathway, derived from one organism, but targeted at a second distinct organism. Alternatively, a family of genetic homologs, orthologs and/or paralogs could be targeted for conservation testing. Alternatively, forensic DNA sequencing (e.g., for crime scene investigation) may target a handful of unique identifying sequences in specific loci including, e.g., unique short tandem repeats, which can enable the confident identification of individuals. The number of different hook molecules, each with a different capture sequence, can be from about 2 to about 100,000 or more. In some cases mixtures have from about 5 to about 10,000 or from about 10 to about 1000 different capture regions. The isolation of specific nucleic acid sequences of interest is valuable when greater efficiency of characterization is desired. For example, even with current sequencing technologies, sequencing of whole genomes for many individuals can be impractical. However, by focusing on specific regions of interest, characterization of many genomes can be made more practical. See e.g. Teer J K, Mullikin J C. "Exome sequencing: the sweet spot before whole genomes", Human Molecular Genetics. 2010 Oct. 15; 19(R2):R145-51 and Mamanova L, Coffey A J, Scott C E, Kozarewa I, Turner E H, Kumar A, Howard E, Shendure J, Turner D J. "Target-enrichment strategies for next-generation sequencing" Nature Methods. 2010 February; 7(2):111-8.

In some cases, two or more hook molecules are employed where the capture region or regions are on one strand of the double-stranded portion. In some cases, two or more hook molecules are employed where the capture region or regions of one or more of the hook molecules is on one strand, and another capture region or region is on the complementary strand. This second approach can be used, for example, for capture of species such as 350 shown in FIG. 3 in which a SMRTBell™ type template nucleic acid is used and in which two active enzymes are bound.

In some cases in order to capture larger nucleic acid sequences, tiling strategies can be used, whereby sets of shorter oligonucleotides are used with each member of the set targeted to a different portion of the larger nucleic acid sequence. For example, in some cases it could be desired to specifically target a 2 kb sequence of DNA within a library generated by fragmenting genomic DNA. Any given fragment may only have a portion of the 2 kb sequence of interest, so in order to capture such portions, hook oligos designed to bind to various different portions of the 2 kb sequence can be provided. For example, a tiling strategy could be employed in which a set of capture oligonucleotides was provided for targeting on average, each 50 base region along the 2 kb sequence. This would result in a set of about 40 hook oligonucleotides. The nucleic acid portion which is tiled for capture could be from about 100 to greater than 1000 kb long. In some cases it could be between about 1 kb and about 100 kb. The average sequence for each tile can be varied as needed for the application, and could range, for example, from about 20 bases to about 500 bases. The number of capture sequences directed at a nucleotide sequence can be, for example, from about 10 to about 1000, or from about 20 to about 200. The tiled capture sequences can be used to selectively capture and isolate desired sets of sequences. For example, in some cases, a specific exon, or a specific family of exons could be targeted for isolation. The exons of a specific organism such as human or mouse could be targeted. In some cases, the nucleic acids characteristic of a specific virus, bacterium, or pathogen or a specific strain can be targeted. In other cases nucleic acids representing various functional classes, e.g. those coding for kinases can be targeted for isolation. In some cases, nucleic acids of interest in a particular biological process, such as those implicated in cancer progression or response to drug therapies, can be targeted.

In some cases an iterative capture and retrieval process is employed where a first hook oligonucleotide targeting a first sequence is used to isolate active complex having the that sequence, then in a subsequent step, a second hook oligonucleotide is used to capture a second sequence. This results in the isolation of only molecules having both the first and the second capture sequences. In some cases the first and second sequences can be on the same strand of the double stranded portion of the nucleic acid, and in some cases one sequence is on one strand and the other sequence is on the other strand. In some cases, rather than a single first hook oligonucleotide, a set of first hook oligonucleotides to capture a set of first sequences is employed. Analogously, in some cases rather than a second oligonucleotide, a second set of oligonucleotides is used to capture a set of second oligonucleotides. These iterative isolation and purification methods allow for selecting and isolating only complexes having a desired set of sequences.

In some embodiments, the hook comprises beads that have two types of capture regions attached to them, a first capture region directed to a first sequence, and a second capture region directed to a second sequence. These beads are added to a solution with a mixture of template nucleic acids, some having only the first or the second capture sequence, and some having both the first and the second capture sequence. The stringency of the solution is adjusted such that complex only bound through a single interaction will be washed off, but complex bound through both the first region and the second region will remain bound to the beads. This provides a one-step method for isolating nucleotides from the mixture that have two sequences of interest. In some cases, the two sequences are on the same strand; in some cases, the two sequences are on opposite strands. While this approach is generally used with two types of capture regions on a bead, the same approach can be used employing beads having 3, 4, or more types of capture regions attached to them, but the difficulty of controlling the hybridization to differentiate the multiply bound species goes up with the number of capture regions.

The retrieve region of the hook molecule is provided for removal and isolation of the hook molecule and the polymerase-nucleic acid complex that is associated with it. In some cases, the retrieve region comprises a bead or other solid surface. In some cases, the retrieve region comprises a member of a binding pair which allows for removal of the hook by a bead or surface comprising the other member of the binding pair. The binding pair for retrieval of the hook can bind by hybridization, ionic, H-bonding, VanderWaals or any combination of these forces. In some cases, the retrieval can be done using hybridization, e.g. using specific sequences or by using polynucleotide sequences. For example, one member of the biding pair can comprise either poly(A), poly(dA), poly(C) or poly(dC), and the other binding member can comprise poly (T), poly(dT), poly(G) or poly(dG). The length of the polynucleotide sequence can be chosen to provide the best binding and release properties. The binding and release can be controlled, for example, by controlling the stringency of the solution. Non-natural and modified bases can also be used in order to control the binding and release properties.

Binding members can comprise, e.g., biotin, digoxigenin, inosine, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

The use of beads for isolation is well known in the life sciences, and any suitable bead isolation method can be used with the present invention. As described above, the beads can be part of the book molecule, or can be added in a subsequent step to bind to and retrieve the hook molecule. Beads can be useful for isolation in that molecules-of-interest can be attached to the beads, and the beads can be washed to remove solution components not attached to the beads, allowing for purification and isolation. The beads can be separated from other components in the solution based on properties such as size, density, or dielectric, ionic, and magnetic properties. In preferred embodiments, the beads are magnetic. Magnetic beads can be introduced, mixed, removed, and released into solution using magnetic fields. Processes utilizing magnetic beads can also be automated. Magnetic beads are supplied by a number of vendors including NEB, Dynal, Micromod, Turbobeads, and Spherotech. The beads can be functionalized using well known chemistry to provide a surface having the binding groups required for binding to the hook molecule.

Solid surfaces other than beads can also be used to retrieve the hook molecules having active polymerase-nucleic acid complexes attached. The solid surfaces can be planar surfaces, such as those used for hybridization microarrays, or the solid surfaces can be the packing of a separation column.

Isolation/Purification

The polymerase-nucleic acid complex that is bound to the hook molecule and retrieved can then be isolated and purified. Where the hook molecule is bound to a solid surface such as a bead, planar surface, or column, fluid can be washed over the solid surface, removing components of the original mixture that are not bound to the solid surface, leaving behind on the surface the attached complex. This washing can remove, for example, inactive polymerase-nucleic acid complex, excess enzyme, unbound nucleic acids and other components. The wash fluid will generally contain components that assist in maintaining the stability of the polymerase-nucleic acid complex, e.g. by maintaining levels of specific ions, the required level of ionic strength, and the appropriate pH. The stringency of the medium is also controlled during the wash to ensure that the polymerase-nucleic acid complex remains bound during the wash.

In forming the polymerase-nucleic acid complex, it is often desirable to use an excess of polymerase enzyme to ensure a high level of formation and to improve the rate of complex formation. This results in there being free polymerase enzyme in the solution of complex after formation. Thus, the removal of excess enzyme from active polymerase-nucleic acid complex is one of the aims of the method. One of the benefits of the present method over the use of polymerase-nucleic acid complex without isolation is that it frees the user to use a higher amount of polymerase at the stage of forming the complex, resulting in higher yields of polymerase-nucleic acid complex. For example, prior to the use of the present method, enzyme to template ratios on the order of 3 to 1 were generally employed. With the use of this method we are able to use much higher levels of enzyme without the deleterious effects of having the excess enzyme contaminating the complex. For example, we have found that enzyme to template levels of 10:1 to 50:1 provide improved performance.

In addition, we have found that the quality of the isolated polymerase-nucleic acid complex can be improved by adding a polymerase trap to the mixture after binding the polymerase-nucleic acid complex to the solid surface. The polymerase trap is believed to bind with the excess polymerase, allowing it to be removed from the complex by washing. In preferred embodiments, the polymerase trap is heparin. Heparin is commercially available through a number of suppliers. Heparin isolated from porcine intestine can be used. Lower molecular weight versions of heparin can also be employed. Other polymerase traps include oligo-DNA such as M13 DNA, M18 DNA, or single-stranded circular DNA. Heparin is generally added to the solution for a concentration of from about 0.05 mM to about 0.5 mM, or from about 0.001 mM to about 4.0 mM.

Once the active complexes are isolated and the unwanted components of the mixture separated, it is generally desirable to remove the hook molecule from the active complex. As described above, where the hook molecule has captured the complex by nucleic acid hybridization, the complex can be separated from the hook molecule by adjusting the stringency of the solution. For example, the complex can be released by raising the stringency of the solution, for example by lowering the ionic strength or raising the temperature.

We have found that in some cases, it is desirable to use a hook molecule having both a capture region and a retrieval region, each of which bind by nucleic acid hybridization. By using this approach, one can control which linkage, e.g. the capture linkage or the retrieval linkage is maintained. It is well known that the melting temperature (Tm) of a hybridized portion of oligonucleotides can be adjusted, for example by increasing the number of matched bases, by including unmatched bases, or by including non-natural bases (See, e.g. Sambrook and Russell, Molecular Cloning, a Laboratory Manual, 2001, Cold Spring Harbor Press). Thus the relative strength of linkages can be controlled by controlling the relative Tm. The melting temperature (Tm) is not an absolute value but is dependent on various factors, for example on the ionic strength of the solution. This allows for two linkages to be formed, one having a higher Tm than another, then by controlling the stringency of the solution, one can control whether both of the links, one of the links, or neither of the links are broken.

In a preferred embodiment, the linkage between the capture region of the hook oligonucleotide and the complex is designed to have a lower Tm than the linkage between the retrieval region of the hook oligonucleotide and the solid substrate. This allows for the stringency of the solution to be lowered in order to release the polymerase-nucleic acid complex from the hook molecule while the linkage between the hook molecule and the solid substrate (e.g. bead) remains intact. The polymerase complex can thereby be cleaved from the solid substrate into solution, leaving the hook molecule behind. In some cases, the Tm of the hook-to-complex linkage is between about 2 degrees and about 10 degrees below the Tm of the hook-to-solid substrate (e.g. bead) linkage, in some cases, the Tm of the hook to complex linkage is between about 5 degrees and about 50 degrees below the Tm of the hook to solid substrate (e.g. bead) linkage.

As described in more detail below, we have found that one method for removing the polymerase-nucleic acid complex from the hook oligonucleotide is to bring the complex into physical contact with a substrate that binds to the polymerase-nucleic acid complex. For this type of physical removal of the complex, we have found that engineering the same types of hybridization interactions as described above for removal of complex by adjusting solution stringency can be used. For example, using the methods described above, a construct comprising a polymerase-nucleic acid complex captured by a hook oligonucleotide retrieved by a bead can be formed. The polymerase in the complex has attached to it a binding moiety such as a biotin or streptavidin. The beads are then brought into proximity or into physical contact with a substrate comprising binding groups that bind to the polymerase enzyme. The binding of the polymerase to the surface is engineered such that it is stronger than the linkage between the hook oligonucleotide and the complex or the hook oligonucleotide and the solid surface, resulting in the complex remaining on the surface when the bead is moved relative to the surface. For example, a biotin-streptavidin type linkage is generally stronger than a linkage formed through hybridization of oligonucleotides on the order of 5 to 40 nucleotides, thus a biotin-streptavidin type linkage is used at the surface, and a hybridization linkage, e.g. of between about 5 and 40 matched nucleotides, is used for the other linkages. For the physical release methods as for the solution methods, the linkage between the complex and the hook oligonucleotide can be produced to have a lower Tm than the linkage between the hook oligonucleotide and the bead, resulting in a higher likelihood of breaking the bond between the hook oligonucleotide and the complex, resulting in delivery of the complex to the surface. In some cases, the Tm of the hook-to-complex linkage is between about 2 degrees and about 10 degrees below the Tm of the hook-to-solid substrate (e.g. bead) linkage, in some cases, the Tm of the hook-to-complex linkage is between about 5 degrees and about 50 degrees below the Tm of the hook-to-solid substrate (e.g. bead) linkage.

While in many cases it is desirable to selectively break the linkage between the hook molecule and the complex. There may also be cases where it is preferred to selectively break the linkage between the solid substrate and the hook molecule. Such approaches can also be implemented as part of the invention.

In some cases, the hook oligonucleotide comprises a primer. For example, the capture portion of the hook molecule can act as a primer for polymerase mediated nucleic acid synthesis, for example, to carry out single molecule sequencing. For example, where a template molecule comprising a double stranded region and a single stranded region (e.g. a hairpin region) is used as the template, a hook molecule having a capture region and a retrieval region can be hybridized through the capture region to the single stranded portion of the template. The capture region can act as a primer for the complexation of a polymerase to form a polymerase-nucleic acid complex. This complex can then be isolated or removed from using the retrieval region of the hook molecule. The retrieval region can either comprise a bead or can comprise a coupling portion that can couple to the bead. For example, the retrieval region can comprise a poly(A) or poly(dA) region that can hybridize with a bead having poly(T) or poly(dT) moities attached.

Conditions for Nucleic Acid Synthesis

The conditions required for nucleic acid synthesis are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors.

Enzymatic reactions are often run in the presence of a buffer, which is used, in part, to control the pH of the reaction mixture. Buffers suitable for the invention include, for example, TAPS (3-{([tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

As used in the art, the term nucleotide refers both to the nucleoside triphosphates that are added to a growing nucleic acid chain in the polymerase reaction, and also to refer to the individual units of a nucleic acid molecule, for example the units of DNA and RNA. Herein, the term nucleotide is used consistently with its use in the art. Whether the term nucleotide refers to the substrate molecule to be added to the growing nucleic acid or to the units in the nucleic acid chain can be derived from the context in which the term is used.

The nucleotides or set of nucleotides used during nucleic acid synthesis are generally naturally occurring nucleotides but can also include modified nucleotides (nucleotide analogs). The nucleotides used in the invention, whether natural, unnatural, modified or analog, are suitable for participation in the polymerase reaction. The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812. Labels such as fluorescent dye groups may be located in various positions on the nucleotide. In some cases, a fluorescent dye is located on the terminal phosphate of the nucleotide.

The nucleotide compositions may include nucleoside triphosphates, or analogs of such compounds. For example, in some cases, the reaction mixtures will include nucleotide analogs having longer phosphate chains, such as nucleoside tetra, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In particularly preferred aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of one or more phosphate groups, typically two or more or three or more phosphate groups, or otherwise modified, are generally referred to herein as nucleotides.

Physical Transfer of Isolated Polymerase-Nucleic Acid Complexes to Substrates

We have found that the constructs of the present invention allow for deposition of isolated polymerase-nucleic acid complexes directly onto substrates. We have found that this can be accomplished without the step of removing the polymerase-nucleic acid complex from the solid surface (e.g. bead). In general, the method comprises obtaining solution of beads that have polymerase-nucleic acid complexes attached to them. The solution of beads is brought into contact with a substrate onto which it is desired to deposit the complexes. The substrate that is used is prepared to have groups that bind to the polymerase-nucleic acid complexes. After the solution of beads is brought into contact with the surface, the beads are removed, leaving polymerase-nucleic acid complexes bound to the substrate. We have found that prior to removal of the beads from the substrate, it is also generally desirable to induce movement between the beads and the substrate, e.g. moving the beads across the surface of the substrate in order to increase the number of complexes that are deposited. We have found that the physical deposition methods allow for depositing polymerase-nucleic acid complexes using relatively low amounts of material as compared to depositing from solution of polymerase-nucleic acid complexes. One way to interpret this result is that by attaching the polymerase-nucleic acid complexes to the surfaces of the beads and bringing the beads into proximity or into contact with the substrate, the effective concentration of the complexes at the surface is increased over what it would be if the same number of molecules had to reach the substrate by diffusion.

The beads coated with polymerase-nucleic acid complex can be produced as described herein or in any other suitable manner. While the invention is described in terms of beads, it is to be understood that other solid surfaces having polymerase-nucleic acid complexes attached can be used, as long as the solid surface can be brought into proximity or into contact with the substrate to deposit polymerase-nucleic acid complexes. The beads are generally spherical, but can have any other suitable shape, for example fibers, rods, disks, cubes, or other shaped materials can be used. Beads are useful as they can be readily manipulated within a solution. Beads for use in the invention can be functionalized on their outer surfaces for the attachment of polymerase-nucleic acid complexes. Suitable beads include polymeric beads having functional organic molecules on their surfaces allowing for such attachment. A variety of types of types of beads are known and used and many are commercially available. The beads can be produced in various size ranges from the nanometer to the millimeter size range. In some cases, the beads can be produced to be relatively monodisperse, which can be helpful in obtaining consistent results.

The beads can be brought into proximity or contact with the substrate in a variety of ways. Forces such as gravitational force, centrifugal force, magnetic, electrical, or dielectric forces or a combination thereof can be used to bring the beads contact the beads with the surface and to move the beads with respect to the surface. In preferred approaches, magnetic beads are used, and magnetic fields are applied both to bring the beads down into proximity or into contact with the substrate and to move the beads across the substrate.

Magnetic beads have been used for purification and separation in chemical and biochemical processes, and functionalized magnetic beads are commercially available. For example, NEB offers a variety of magnetic beads including Amylose Magnetic Beads, Anti-MBP Magnetic Beads, Chitin Magnetic Beads, Goat Anti-Mouse IgG Magnetic Beads, Goat Anti-Rabbit IgG Magnetic Beads, Goat Anti-Rat IgG Magnetic Beads, Hydrophilic Streptavidin Magnetic Beads, Protein A Magnetic Beads, Protein G Magnetic Beads, Streptavidin Magnetic Beads, SNAP-Capture Magnetic Beads, Oligo(dT) Magnetic Beads; Dynal (Life Technologies) offers a variety of functionalized magnetic beads including streptavidin coated beads, beads for binding with His tags, anion exchange, cation exchange, hydrophobic capture, and antibody beads. Micromod offers magnetic beads functionalized with surface functionalities NH2, PEG-NH2 and PEG-COOH for the covalent binding of proteins, antibodies or other molecules. Tubobeads LLC offers beads having streptavidin, sulfonate, carboxylate, or ammonium functionality. Spherotech Inc. offers magnetic beads having a variety of functionalities including carboxyl, amino, antibodies, and proteins. Using functionalized beads and known methods of surface polymer synthesis, beads with a variety of properties can be made, including those having oligonucleotides or peptides having specified sequences.

The beads can comprise polymers including polystyrene/polymethacrylate, dextran, crosslinked dextran, silica-fortified dextran, starch (BNF-starch particles), poly(lactic acid), poly(ethylene imine), or chitosan. The beads can also be made from inorganic material such as carbon, iron oxide, silica, or silicon. The magnetic beads can be useful as long as they are effectively moved by an applied magnetic field. For example, the beads can be ferromagnetic or paramagnetic, or superparamagnetic.

The methods of the invention can also be used to deposit molecules other than polymerase-nucleic acid complexes. The invention allows for loading enzymes, proteins, nucleic acids, sugars, or other molecules onto a surface. In some embodiments the invention comprises providing a solution of beads, the beads having attached to them a molecule-of-interest through a bead to molecule-of-interest linkage; exposing the solution of beads to a substrate having a plurality of binding molecules for binding the molecule-of-interest to the substrate; bringing the beads into physical contact with the substrate using a force; optionally providing a force to move the beads across the substrate surface; then removing the beads from the substrate leaving molecules-of-interest attached to the substrate surface through the binding groups. The bead to molecule-of-interest linkage is preferably formed by oligonucleotide hybridization. As described herein, the relative strength of such a linkage can be engineered such that this linkage will break more easily than the bond between the molecule-of-interest and the substrate, allowing for removal of the beads while leaving the molecule-of-interest on the substrate. In some cases, the substrate comprises an array of nanoscale wells such as ZMWs where binding molecules are present on the bases of the nanoscale wells such that molecules-of-interest are deposited into the nanoscale wells.

The molecule-of-interest that can be deposited onto a substrate can be any suitable molecule including for example, proteins, nucleic acids, sugars, or combinations thereof. The molecules-of-interest can include biomolecules and catalysts, and enzymes.

In some embodiments the method comprises: providing a solution of beads wherein each bead comprises a single molecule-of-interest or a plurality of molecules-of-interest linked thereto by a bead to molecule-of-interest linkage; exposing the solution of beads to a substrate, the surface of the substrate comprising binding molecules for binding the molecules-of-interest; using a contacting force to bring the beads into proximity or into physical contact with the substrate and optionally using a distributing force to move the beads across the surface of the substrate; and removing the beads from the substrate, thereby producing a substrate having molecules-of-interest bound to its surface through the binding molecules.

The methods, compositions, and devices of the invention are particularly useful for performing single-molecule analysis. A reason for this is that the methods are useful for providing molecules-of-interest such as polymerase-nucleic acid complexes at relatively sparse levels on a substrate. Thus the method can be used to deposit molecules-of-interest on a substrate such that the molecules-of-interest are provided at a surface density such that the molecules-of-interest are independently optically observable. In some cases, the substrate comprises an array of nanoscale wells such as arrays of zero mode waveguides (ZMWs). For example, the substrate can have a transparent lower layer comprised, for example, of fused silica, upon which is deposited a cladding layer with a thickness of between about 10 nm and about 500 nm. The cladding layer is generally an opaque layer and can be a metal layer. Through the cladding layer is an array of holes extending to the transparent substrate, and in some cases extending into the transparent substrate. The holes can have any suitable cross-sectional profile including a circular profile. Where the holes have a circular profile, the diameter of the holes is generally from about 20 nm to about 500 nm. The holes extending to the transparent substrate will generally have a portion of the transparent substrate as their base, thus forming nanoscale wells. For use in the present invention, the arrays of nanoscale wells are functionalized such that binding molecules are attached at the bases of the wells for binding the molecule or molecules-of-interest, such as a polymerase-nucleic acid complex, within the well. In some cases, the arrays are selectively functionalized such that a higher density of binding molecules is present within the wells than outside of the wells. Approaches to functionalizing zero mode waveguide substrates are provided in U.S. Pat. Nos. 7,833,398, 7,292,742 and in U.S. patent application Ser. Nos. 11/731,748, filed Mar. 29, 2007, 12/079,922, filed Mar. 27, 2008, and 12/074,716, filed Mar. 5, 2008, the full disclosures of which are incorporated by reference herein for all purposes. As described elsewhere herein, these nanoscale wells provide for carrying out analyses on very small numbers of molecules down to single molecules. In some cases the methods, devices, and compositions of the invention allow for the deposition of single molecules-of-interest within nanoscale wells.

When depositing molecules-of-interest, e.g. polymerase-nucleic acid complexes into ZMWs, in some cases, we have found that it is desirable for the diameter of the beads to be larger than the smallest cross-sectional dimension for the ZMW; where the ZMW has a circular profile, larger than the diameter of the ZMW. In some cases the diameter of the bead is 20% greater or more than the smallest cross-sectional dimension of the ZMW. In some cases the diameter of the bead is 2 times greater or more than the smallest cross-sectional dimension of the ZMW. In some cases the diameter of the bead is 2 times greater to 10,000 times greater than the smallest cross-sectional dimension of the ZMW. In other cases, it can be useful to have the size of the bead be smaller than the size of the ZMW. The size of the beads can be, for example, from about 40 nm to about 10 microns in diameter.

As would be understood in the art, the beads generally do not have a perfectly spherical shape, and are generally not perfectly monodisperse, but will have a distribution of sizes and shapes. In addition, where the outsides surfaces of the particles are composed of polymers that are soluble or partly soluble in the solution, the surfaces are not smooth flat surfaces, but the groups attached to the surface can extend from the bead on polymer chains into the solution. Though not bound by theory, it is believed that in some cases these polymer chains extending into solution can provide polymer-nucleic acid complex into nanoscale wells from beads that would be too large to fit into the wells. This property can be used to advantage in the loading of ZMWs. In some cases, spacer or linker molecules are provided on the bead surface between a functional group on the bead and the group that is used to link to the hook molecule or to link directly to the molecule-of-interest such as the polymerase-nucleic acid complex. By varying the length of the spacer or linker, one can provide for more or less reach between the surface of the bead and the molecule-of-interest. The spacer or linker can be any suitable molecular structure. It can be made, for example from a polymer such as polypeptide, poly(vinyl alcohol), poly ethylene glycol, or polysaccharide. The linker will generally be made using a polymer that is soluble in the solution that the bead deposition takes place in. Where the molecule-of-interest is an enzyme, this is generally a polar solution, such as an aqueous environment, for which a polar or hydrophilic linker or spacer is used.

In some aspects, the invention provides a method for loading active polymerase-nucleic acid complexes onto a substrate comprising: providing a solution of magnetic beads having polymerase-nucleic acid complexes bound thereto, each polymerase-nucleic acid complex comprising a polymerase enzyme and a template nucleotide; contacting the solution of magnetic beads with the top of a substrate comprising an array of nanoscale wells having bases, wherein the bases of the wells have coupling agent bound thereto; applying a dynamic magnetic field from below the substrate to move the magnetic beads in solution down to the top of the substrate, whereby the dynamic magnetic field causes the particles to be moved across the top surface of the substrate, whereby some polymerase-nucleic acid complexes become bound to the coupling groups on the bases of the nanoscale wells. In some cases, the magnetic field is applied from above or adjacent to the substrate. For example, field focusing can be used which allows for applying magnetic fields from above, yet obtaining a field in which the field gradient is highest below the substrate, tending to pull the magnetic beads down.

The coupling groups or binding molecules on the substrate for coupling to the molecule-of-interest, e.g. polymerase-nucleic acid complex, can be any suitable coupling group or binding molecules. The coupling can be accomplished by forming a covalent bond or through a non-covalent interaction. It is generally desired that the coupling to the substrate result in a strong bond relative to the other linkages, e.g. between the polymerase-nucleic acid complex and the hook molecule and between the hook molecule and the bead. Many types of binding pairs are known in the art. In some cases, an interaction between biotin and a biotin binding protein such as avidin or streptavidin is used. In some cases, an antibody-antigen interaction, for example between digoxigenin and anti-digoxigenin is used. Reactions that form covalent linkages, for example SNAP or Click chemistry can be used to bind the polymerase-nucleic acid complex to the substrate.

Oligonucleotide hybridization can also be used for the attachment. Where such hybridization is used, the linkages are designed such that the oligonucleotide binding to the surface is stronger, e.g. has a higher Tm, than the other linkages between the surface and the bead.

Binding of the polymerase-nucleic acid complex to the substrate is generally carried out by forming a bond to the polymerase. One member of the binding pair is generally used to attach the complex to the substrate is connected directly or indirectly to the polymerase. In some cases, a biotinylation sequence is included when producing the polymerase, the protein is biotinylated and attached to streptavidin prior to formation of the complex. The polymerase-streptavidin is then ready for binding to a substrate that is prepared by having biotin groups on its surface.

Where the molecule-of-interest comprises a polymerase-nucleic acid complex, the solution that is used for deposition with beads is generally an aqueous solution. The components of the solution and the conditions are controlled as described above in order that the polymerase-nucleic acid complex remains intact. For example, the appropriate level of monovalent and divalent ions, the concentration of nucleotide, the pH and the temperature are controlled. It is also generally desired that the polymerase not continue to perform nucleic acid synthesis during deposition, and Sr and Ca can be added in order to inhibit or reduce polymerization.

There is generally a plurality of molecules-of-interest attached to a bead. For example, there can be from tens to millions or more of molecules attached to a bead. In some cases, the beads, or a subset of the beads will each only have one molecule-of-interest attached.

Where beads are used to selectively deliver molecules-of-interest to the substrate, the beads can be brought into contact with the substrate by applying a force to the beads which can involve placing the beads in a field which applies such a force. We have found that an effective process for binding the molecules-of-interest generally involves applying both a field that forces the beads down to the surface of the substrate and a field that moves the beads across the surface of the substrate. These two fields can be different fields, or can be two components of the same field. The fields can be, for example, gravitational, centrifugal, magnetic, electric, or dielectric.

Preferred embodiments of the invention utilize a magnetic field both to bring down the particles and to move the particles across the surface of the substrate, either in contact with or in proximity to the substrate. The magnetic field can be applied using one or more permanent magnets, or using one or more electromagnets. Each of these approaches has its benefits and drawbacks, and each can be employed to carry out the invention. In some cases, one, two, three, four or more permanent magnets are held below the substrate, and are continuously moved with respect to the substrate. In this manner, the beads are both pulled down to the substrate and are moved across the substrate surface. The movement of the magnet or magnets can be in any pattern that provides suitable movement of the beads. The beads can be moved around in the plane of the substrate, or can be moved such that they move away from and back toward the substrate as well. A circular movement of one or more magnets underneath the substrate has been found to be straightforward to implement and to provide the requisite movement. In some cases, the magnets can remain fixed and the substrate moved with respect to the magnets. In some cases, both the substrate and the magnet are moved.

The choice of the mode of magnetic movement will also depend on the size and shape of the substrate to which the beads are to be contacted or moved into proximity of. For example, the magnets can be made to trace wider circles to ensure that the beads come into contact with the outer regions of a larger surface. In some embodiments, two magnets held next to one another under the substrate are used, one having its north pole facing upward, and the other having its north pole facing downward. This pair of magnets is attached to a mechanism that rotates the pair underneath the substrate. The pair of magnets is rotated in the plane of the substrate below the substrate at about 10 to about 120 rpm. In some cases, rotation rates of 1 rpm to 600 rpm, 3 rpm to 120 rpm, or 6 rpm to 20 rpm are used. The beads are moved across the substrate typically for about 5 to about 20 minutes, but in some cases for about 1 minute to about 2 hours. A variety of permanent magnets are readily available commercially. For example, Dura Magnetics Inc. has available on their website (http://www.duramag.com/magnet-materials.html) various magnets including magnets having various magnetic strengths. The type and shape of the permanent magnet can be chosen for ease of implementation and to optimize loading. For example, button magnets, bar magnets, or sheet magnets can be employed.

One or more electromagnets can also be utilized to move the particles for deposition. For example one or more electromagnets can be mounted below the substrate, and the current to the electromagnet(s) can be varied in order to vary the strength of the magnetic field. By placing multiple electromagnets in a pattern, and controlling the current to each of the electromagnets, a moving magnetic field can be produced above the substrate which can both bring clown the magnetic particles and move the particles across the substrate surface. The use of electromagnets has the advantage that a system for moving the beads can be constructed with no moving parts. The current flowing through the electromagnets will produce heat at the electromagnet. When using this approach, this heat generation should be taken into account. In some cases, when using electromagnets, heat-sinking, insulation, and/or active cooling is provided to control the temperature.

The magnetic strength, number of magnets, speed of movement, distance from substrate, and time of deposition can be varied to obtain the desired results. We have found that even for very small magnetic beads, microscopy can be used to observe the behavior of the cloud of beads being moved by the magnetic field in real time. These observations can also be used to set the appropriate parameters for deposition.

Gravitational fields can be used for relatively large beads. As the beads get smaller, the ability of a gravitational force to move the beads down from solution becomes limited. We have found that beads having a mean diameter of about 3 microns can be deposited onto a zero mode waveguide chip to load polymerase-nucleic acid complexes using gravity alone. Loading was seen with exposures less than 1 hour. We found that gravitational loading will result in higher levels of loading for larger templates just as was seen with magnetic loading. In some cases, the chip can be slowly rotated while the beads move across the top of the surface. The rotation allows for the beads to move relative to the chip surface. In some cases, the chip is tilted while it is rotated to facilitate the movement of the beads across the surface. Centrifugal fields can also be applied to bring down the beads and also to move the beads across the surface of the substrate. For example, the substrates can be mounted within a centrifuge such that the substrate is at an angle with the centrifugal force vector, and the substrate can be rotated such that the beads move around across its surface.

Electric fields can be used to move the particles where the particles have the characteristics that they will move in an electric field. For example, particles having a net charge, or particles made of a polymer having a net charge surrounded by counterions of the opposite charge, will move in an electric field. As with the description above for the magnetic field, a dynamic electric field can be used to both move the particles to the substrate and to move the particles across the surface of the substrate. Typically electrodes will be placed in contact with the solution. The appropriate voltages are then applied to the electrodes as a function of time to produce the electric field. Particles can also be made to move according to the invention using dielectric field gradients and alternating currents. Acoustic fields (sonication) can be used to move the beads relative to the surface. Hydrodynamic forces, e.g. through creation of a vortex, can also be utilized.

Combinations of fields can also be used. For example a magnet can be used to pull down the beads and another force, such as ultrasonication, can be used to move them, or centrifugation can be used to pull down the beads and a separate force used to move them.

One object of the invention is providing molecules-of-interest such as polymerase-nucleic acid complexes to a substrate for single molecule analysis. For single molecule analysis it is generally desired that single molecules-of-interest are bound to a substrate at a density and pattern such that the optical signal from one molecule can be detected distinctly from signals from other molecules and from solution. That is, the molecules are deposited so as to be individually optically resolvable. One method that has been used for this purpose is to deposit molecules-of-interest from a solution that is diluted such that on average, an acceptable number of single molecules will be individually optically resolvable. If the concentration is too high, the density on the surface will be such that few, if any, single molecules will be resolvable. If the concentration is too low, this may also result in very few single molecules. The methods, devices and compositions of the present invention provide an alternative approach for obtaining high levels of optically resolvable single molecules on a substrate.

As described above, a preferred substrate for single-molecule analysis is a zero mode waveguide (ZMW) array. Here, the optical analysis is carried out only within the ZMWs on the surface. We have found that the invention provides useful methods for loading single molecules into a ZMW array. As with other substrates for single molecule analysis, loading molecules-of-interest onto ZMWs to obtain acceptable numbers of single molecules has often been carried out with a dilution method where solutions at various dilution levels are applied to the surface to obtain the optimal loading. The methods of the invention provide tools for controlling the way in which molecules-of-interest are loaded into ZMWs.

When depositing a library of polymerase-nucleic acid complexes onto a substrate, for example a ZMW substrate, by diffusion from solution, we have found that there can be a relatively large number of smaller fragments deposited than of larger fragments. We have found that by depositing with beads, there can be a much more even distribution of deposited polymerase-nucleic acid complexes by size, allowing for a better representation of the larger size fragments in the data in single molecule analysis. In some cases, bead loading also allows for preferential loading of larger size fragments over smaller size fragments.

Since ZMWs are wells with defined dimensions, the sizes, shapes, and extension (reach) of the beads can be used to control the manner in which molecules-of-interest are deposited. For example in some cases, beads are used that have a size that is smaller than a characteristic dimension of the ZMW, such that a bead fits into a ZMW, and has a reach such that only molecules-of-interest from a bead fitting into the ZMW will be deposited. In some cases, beads will be used that are smaller than the diameter of a ZMW, but larger than half of the diameter of the ZMW. In this way, only one bead will deposit into the ZMW, preventing the deposition of a second bead, ensuring that each ZMW will only receive molecules-of-interest from one bead. For example, for a ZMW array having ZMWs with diameters of 200 nm, beads having diameters from about 100 nm to about 190 nm are used. Another way of controlling the level of loading is by controlling the density of molecules-of-interest on the surfaces of the beads. For example, by using sparsely functionalized beads, only small numbers of molecules-of-interest will be deposited.

When loading a surface for single molecule analysis, generally a small amount of material is deposited as compared to the total amount on the bead. This allows for re-using the beads by removing them from the substrate, optionally storing them, and then applying them to another substrate. The beads can be re-used in some case to load substrates 1, 2, 3, 4, 5, 10, 20 or more times while still obtaining acceptable loading. We have found that after each loading, the amount loaded onto the next substrate may be slightly less, but that the levels on the later substrates are still acceptable. Comparable levels can also be obtained on later substrates by changing deposition conditions, for example by lengthening the time of deposition. The ability to re-use the beads can be important for getting the most out of small samples. The ability to store the beads for future loading and testing can be important for the integrity of the data from a study. We have also found that the beads with bound polymerase-nucleic acid complex can be stored for days, weeks, and for over a month without any measurable deterioration in properties.

Physical Transfer of Biological Molecules to Substrates

The devices, systems, and methods described herein for transferring template-polymerase complexes onto substrates can also be used to transfer other biomolecules onto substrates and into zero mode waveguides. The methods comprise, for example, attaching a biomolecule or a population of biomolecules to beads, and drawing the beads down to a surface to transfer the biomolecules to the surface. The biomolecules are preferably attached to the beads by association or hybridization such that the attachment can be broken to leave the biomolecule attached to the surface even if the bead is removed from the area. The beads can be magnetic beads that are drawn to the surface and optionally translated with respect to the surface during the loading process as described herein. The surface will generally have reactive components that will react with the biomolecule or with a molecule associated with the biomolecule to attach it to the surface. in some cases, the substrate comprises an array of zero mode waveguides functionalized on the bases of the zero mode waveguides to provide attachment of the biological molecules within the observation region of the zero mode waveguide.

The biological molecules can be any suitable biomolecule including a protein, a nucleic acid, a lipid, a polysaccharide, or a combination of these types of molecules. In some embodiments enzymes are loaded onto the substrate. Many types of enzymes are known in the art that can be used herein. The biological molecules can be comprise constructs made of associated subunits that are bound onto the surface together. For example, the biological molecules can comprise a ribosome. The biological molecules can comprise antibodies or binding proteins.

Sequencing by Incorporation

The methods, devices, and compositions of the invention are particularly useful for single molecule sequencing, and specifically single molecule sequencing by incorporation in real time. For sequencing processes that rely upon monitoring of the incorporation of nucleotides into growing nascent strands being synthesized by the complex, the progress of the reaction through these steps is of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

Figure 8:
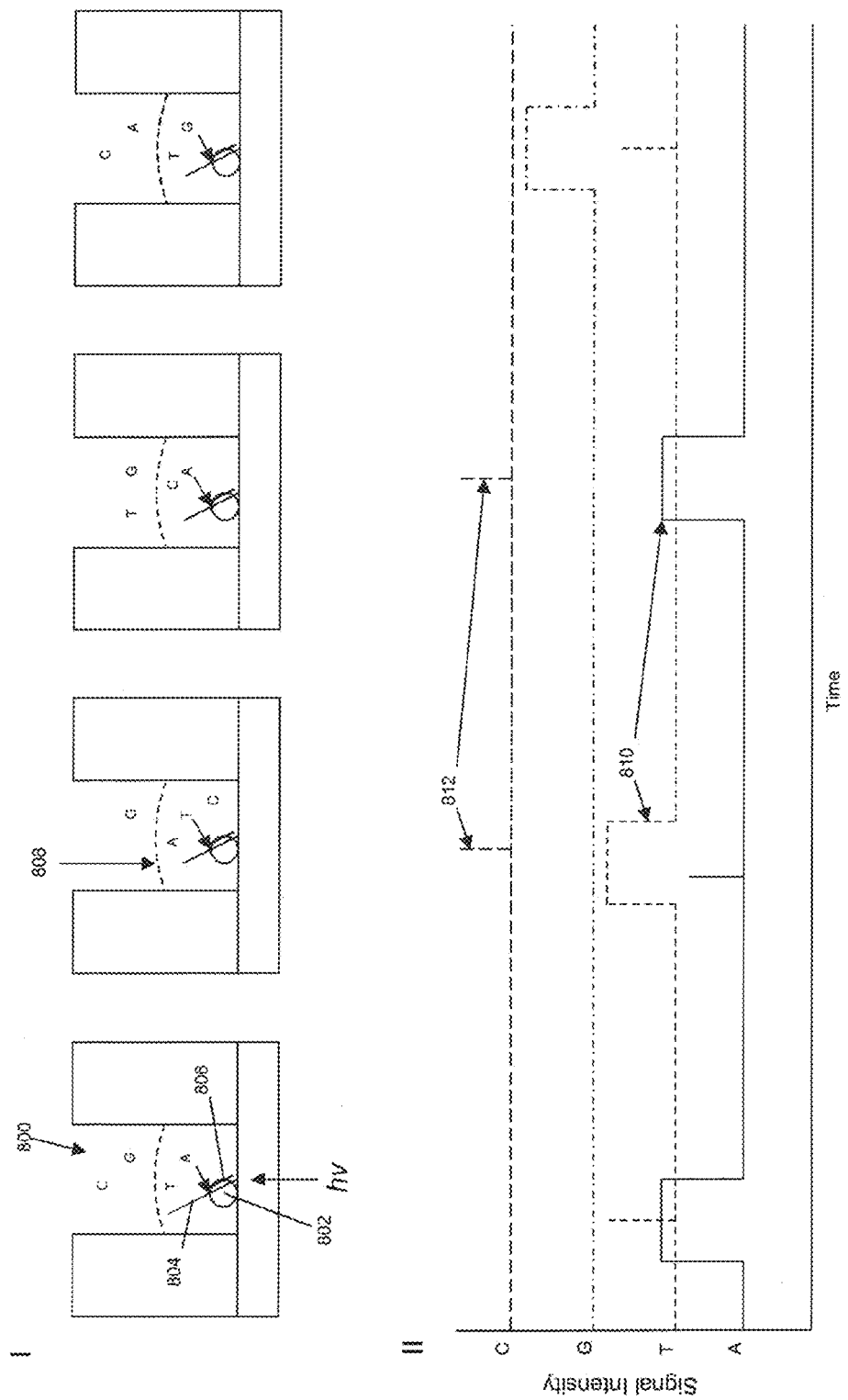
FIG. 8 illustrates a method for single molecule sequencing.

In the first exemplary technique, as schematically illustrated in FIG. 8, a nucleic acid synthesis complex, including a polymerase enzyme 802, a template sequence 804 and a complementary primer sequence 806, is provided immobilized within an observation region 800, that permits illumination (as shown by hv) and observation of a small volume that includes the complex without excessive illumination of the surrounding volume (as illustrated by dashed line 808). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particular, as shown in panel II of FIG. 8, when a nucleotide, e.g., A, is incorporated into by the polymerase, it is retained within the observation volume for a prolonged period of time, and upon continued illumination yields a prolonged fluorescent signal (shown by peak 810). By comparison, randomly diffusing and not incorporated nucleotides remain within the observation volume for much shorter periods of time, and thus produce only transient signals (such as peak 812), many of which go undetected, due to their extremely short duration.

In particularly preferred exemplary systems, the confined illumination volume is provided through the use of arrays of optically confined apertures termed zero-mode waveguides, e.g., as shown by confined reaction region 100 (ZMWs) (See, e.g., U.S. Pat. No. 6,917,726, which is incorporated herein by reference in its entirety for all purposes). For sequencing applications, the DNA polymerase is provided immobilized upon the bottom of the ZMW (See, e.g., Korlach et al., PNAS U.S.A. 105(4): 1176-1181. (2008), which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al., Nucleosides, Nucleotides and Nucleic Acids, 27:1072:1083, 2008.

In the second exemplary technique, the nucleotides to be incorporated are each provided with interactive labeling components that are interactive with other labeling components provided coupled to, or sufficiently near the polymerase (which labels are interchangeably referred to herein as "complex borne"). Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair or FRET pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal, e.g., quenched or otherwise indicative of energy transfer. Upon incorporation and cleavage of the terminal phosphate groups, e.g., bearing a donor fluorophore, the quenching or other energy transfer is removed and the resulting characteristic fluorescent signal of the donor is observable.

Single-Molecule Sequencing Processes and Systems

In preferred aspects, the synthesis complexes in such reaction mixtures are arrayed so as to permit observation of the individual complexes that are being so modulated. In arraying individual complexes to be individually optically resolvable, the systems of the invention will position the complexes on solid supports such that there is sufficient distance between adjacent individual complexes as to allow optical signals from such adjacent complexes to be optically distinguishable from each other.

Typically, such complexes will be provided with at least 50 nm and more preferably at least 100 nm of distance between adjacent complexes, in order to permit optical signals, and particularly fluorescent signals, to be individually resolvable. Examples of arrays of individually resolvable molecules are described in, e.g., U.S. Pat. No. 6,787,308.

In some cases, individual complexes may be provided within separate discrete regions of a support. For example, in some cases, individual complexes may be provided within individual optical confinement structures, such as zero-mode waveguide cores. Examples of such waveguides and processes for immobilizing individual complexes therein are described in, e.g., Published International Patent Application No. WO 2007/123763, the full disclosure of which is incorporated herein by reference in its entirety for all purposes.

As noted previously, in preferred aspects, the synthesis complexes are provided immobilized upon solid supports, and preferably, upon supporting substrates. The complexes may be coupled to the solid supports through one or more of the different groups that make up the complex. For example, in the case of nucleic acid polymerization complexes, attachment to the solid support may be through an attachment with one or more of the polymerase enzyme, the primer sequence and/or the template sequence in the complex. Further, the attachment may comprise a covalent attachment to the solid support or it may comprise a non-covalent association. For example, in particularly preferred aspects, affinity based associations between the support and the complex are envisioned. Such affinity associations include, for example, avidin/streptavidin/neutravidin associations with biotin or biotinylated groups, antibody/antigen associations, GST/glutathione interactions, nucleic acid hybridization interactions, and the like. In particularly preferred aspects, the complex is attached to the solid support through the provision of an avidin group, e.g., streptavidin, on the support, which specifically interacts with a biotin group that is coupled to the polymerase enzyme.

The sequencing processes, e.g., using the substrates described above and the synthesis compositions of the invention, are generally exploited in the context of a fluorescence microscope system that is capable of illuminating the various complexes on the substrate, and obtaining, detecting, and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, and focusing and direction of the excitation and/or emission light to and from the substrate.

Figure 9:
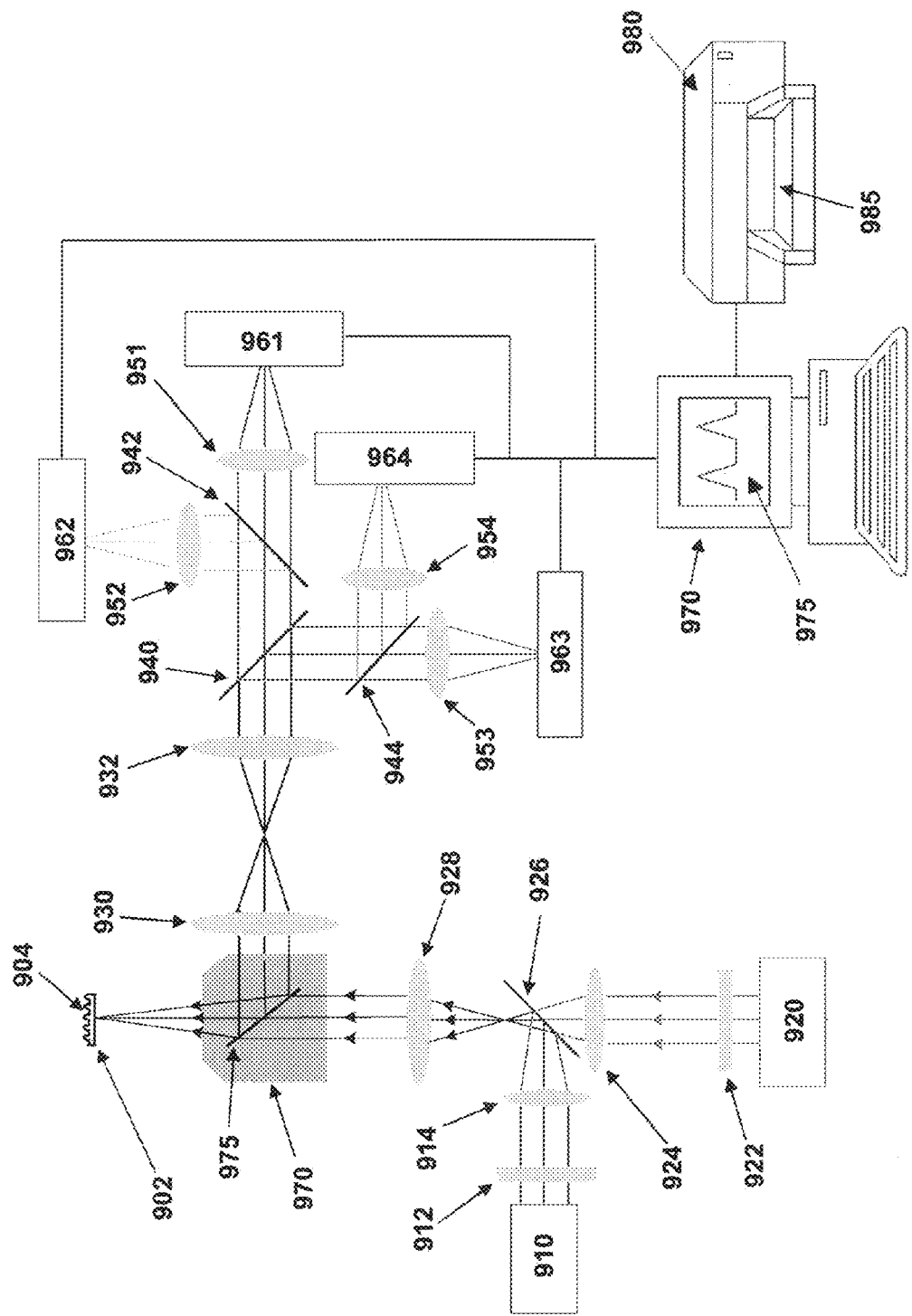
FIG. 9 illustrates an apparatus that can be used for single molecule sequencing

One such exemplary system is shown in FIG. 9. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention, For a discussion on the advantages of such systems, see, e.g., U.S. patent application Ser. Nos. 11/704,689, filed Feb. 9, 2007, 11/483,413, filed Jul. 7, 2006, and 11/704,733, filed Feb. 9, 2007, the full disclosures of which are incorporated herein by reference in their entirety for all purposes.

For purposes of the present invention, the processes and systems will be described with reference to detection of incorporation events in a real time, sequencing by incorporation process, e.g., as described in U.S. Pat. Nos. 7,056,661, 7,052,847, 7,033,764 and 7,056,676 (the full disclosures of which are incorporated herein by reference in their entirety for all purposes), when carried out in arrays of discrete reaction regions or locations. An exemplary sequencing system for use in conjunction with the invention is shown in FIG. 9. As shown, the system includes a substrate 902 that includes a plurality of discrete sources of optical signals, e.g., reaction wells, apertures, or optical confinements or reaction locations 904. In typical systems, reaction locations 904 are regularly spaced and thus substrate 902 can also be understood as an array 902 of reaction locations 904. The array 902 can comprise a transparent substrate having a cladding layer on its top surface with an array of nanoscale apertures extending through the cladding to the transparent substrate. This configuration allows for one or more samples to be added to the top surface of the array, and for the array to be observed through the transparent substrate from below, such that only the light from the apertures is observed. The array can be illuminated from below as shown in FIG. 9, and in some embodiments, the array can also be illuminated from above or from the side (not shown in FIG. 9).

For illumination from below, one or more excitation light sources, e.g., lasers 910 and 920, are provided in the system and positioned to direct excitation radiation at the various signal sources. Here, two lasers are used in order to provide different excitation wavelengths, for example with one laser 910 providing illumination in the red, and another laser 920 providing illumination in the green. The use of multiple laser excitation sources allows for the optimal excitation of multiple labels in a sample in contact with the array. The excitation illumination can be flood illumination, or can be directed to discrete regions on the array, for example, by breaking the excitation beam into an array of beamlets, each beamlet directed to a feature on the array. In order to break the excitation beams into an array of beamlets, a diffractive optical element (DOE) is used. In the system of FIG. 9, the light from excitation sources 910 and 920 is sent through DOE components 912 and 922 respectively. The use of a DOE for providing an array of beamlets is provided, e.g. in U.S. Pat. No. 7,714,303, which is incorporated by reference herein in its entirety. Excitation light is then passed through illumination relay lenses 914 and 924 to interact with dichroic 926. In the system of FIG. 9, the red light from laser 910 is reflected off of dichroic 926, and the green light from laser 920 is directed through the dichroic 926. The excitation light is then passed through illumination tube lens 928 into objective lens 970 and onto the array 902.

Emitted signals from sources 904 are then collected by the optical components, e.g., objective 970, comprising dichroic element 975 which allows the illumination light to pass through and reflects the excitation light. The emitted light passes through collection tube lens 930 and collection relay lens 932. The emitted light is then separated into 4 different spectral channels, and each spectral channel is directed to a different detector. In the system of FIG. 9, the light is separated into four different channels, each channel corresponding predominantly to one of four labels to be detected in the sample. Thus, the system allows the user to obtain four two-dimensional images, each image corresponding to one of the four labels. In order to separate the light into the four spectral channels, dichroics 940, 942, and 944 are used. Dichroic 940 allows the light for channels 1 and 2 to pass while reflecting the light for channels 3 and 4. Dichroic 942 allows the light for channel 1 to pass, through collection imaging lens 951 to detector 961, and reflects the light for channel 2 through collection imaging lens 952 to detector 962. Dichroic 944 allows the light for channel 3 to pass, through collection imaging lens 953 onto detector 963, and reflects the light for channel 4 through collection illumination lens 954 onto detector 964. Each of the detectors 961-964 comprise arrays of pixels. The detectors can be, for example, CMOS, EMCCD, or CCD arrays. Each of the detectors obtains 2-dimensional images of the channel that is directed to that detector. The data from those signals is transmitted to an appropriate data processing unit, e.g., computer 970, where the data is subjected to processing, interpretation, and analysis. The data processing unit is configured to process the data both pixel by pixel and pixel region by pixel region, where each pixel region corresponds to a feature on the substrate. The data processing unit can receive data from calibration runs in order to define software mask pixel weighting, spectral weighting, and noise parameters. These parameters and weightings can be applied to signals that are measured on the detectors during an analytical reaction such as during sequencing. In some embodiments, the data processing unit is configured to define and apply software mask pixel weighting, spectral weighting, and noise parameters that are determined and then applied during an analytical reaction such as during sequencing.

Analyzed and processed data obtained from the analytical reactions can ultimately be presented in a user ready format, e.g., on display 975, printout 985 from printer 980, or the like, or may be stored in an appropriate database, transmitted to another computer system, or recorded onto tangible media for further analysis and/or later review. Connection of the detector to the computer may take on a variety of different forms. For example, in preferred aspects, the detector is coupled to appropriate Analog to Digital (A/D) converter that is then coupled to an appropriate connector in the computer. Such connections may be standard USB connections, Firewire® connections, Ethernet connections or other high speed data connections. In other cases, the detector or camera may be formatted to provide output in a digital format and be readily connected to the computer without any intermediate components.

This system, and other hardware descriptions herein, are provided solely as a specific example of sample handling and image capture hardware to provide a better understanding of the invention. It should be understood, however, that the present invention is directed to data analysis and interpretation of a wide variety of real-time fluorescent detecting systems, including systems that use substantially different illumination optics, systems that include different detector elements (e.g., EB-CMOS detectors, CCD's, etc.), and/or systems that localize a template sequence other than using the zero mode waveguides described herein.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

The present invention can include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium processors, to workstations, laboratory equipment, or high speed servers, running UNIX, LINUX, Windows®, or other systems. Logic processing of the invention may be performed entirely by general purpose logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, Visual Basic, Python, JAVA, CGI, and the like.

While described in terms of a particular sequencing by incorporation process or system, it will be appreciated that certain aspects of the processes of the invention may be applied to a broader range of analytical reactions or other operations and varying system configurations than those described for exemplary purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors employed in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

Loading One Polymerase-Nucleic Acid Complex Per Zero Mode Waveguide

In some applications including in single-molecule sequencing, it is desirable to deposit only a single polymerase-nucleic acid complex in a zero mode waveguide. Conventionally, obtaining a single complex within a zero mode waveguide in an array of zero mode waveguides is carried out statistically by contacting the array of zero mode waveguides with a dilute solution of polymerase-nucleic acid complexes at a concentration such that a fraction of the zero mode waveguides are singly occupied, a fraction are multiply occupied, and a fraction are unoccupied. Using this method there is a limit to the fraction of zero mode waveguides that will be singly occupied. The loading statistics can be modeled as a Poisson distribution, which predicts that a maximum of about 37% of the zero mode waveguides will be singly occupied.

The present invention provides for obtaining loading levels greater than that predicted by a Poisson distribution by producing a population of polymerase-nucleic acid complexes that are of a size such that once one complex becomes bound within a zero mode waveguide, the bound complex blocks the entry and binding of subsequent polymerase-nucleic acid complexes. This can be accomplished by first producing a population of polymerase-nucleic acid complexes and performing a controlled nucleic acid synthesis reaction which grows the nascent strand to a given length or range of lengths. The control of the length can be accomplished, for example, but controlling the concentration of the reaction components and the time of the polymerase reaction. The control of the length of the nascent strand can also be accomplished by having a specific stop point in the template such that the nucleic acid synthesis is halted when it reaches a given size.

Once the population of complexes with the desired size is produced, the complexes are attached to the zero mode waveguides. The attachment of the complexes can be accomplished as described herein. The polymerase within the complex can have a member of a binding pair attached to it (e.g. biotin or streptavidin), such that when exposed to the surface having the other member of the binding pair, an attachment to the surface is made. The attachment can be done either by exposing the substrate to a solution of the polymerase-nucleic acid complex and allowing the complexes to diffuse to the surface, or with a more active loading process such as the bead loading described herein.

The use of circular templates and a strand displacing polymerase allows for the formation of a nascent strand that is longer than that of the template. This can be useful for producing extended complexes that are large enough to block the entry of another complex into the zero mode waveguide. The zero mode waveguides can be, for example, cylinders with diameters from about 50 nm to about 200 nm. The complex need not completely fill the zero mode waveguide to block the entry of another complex. The blocking will be affected by the secondary and tertiary structure of the extended complex. The tertiary structure can be affected, for example, by the ionic composition and by the solvent characteristics such as polarity and hydrogen bonding. These properties can be used to control how well a complex of a given length will block the zero mode waveguide from entry and binding of a second complex.

Exemplary Process for Attaching Complexes to Magnetic Beads and Loading onto a ZMW Chip A library is produced having a plurality of double stranded fragments, the various fragments having sequences from portions of an original DNA sample. The plurality of double stranded fragments can be produced, for example, by shearing or using restriction enzymes. The size distribution can be controlled, for example, to give relatively long fragments—e.g. 10 Kb or greater, or relatively small fragments—e.g. 200-300 bases. Hairpin adaptors are ligated onto the ends of the double stranded fragments to produce circular template molecules having a central double-stranded portion and single-stranded hairpin loops at the ends (see SMRTbell™ from Pacific Biosciences®). The hairpin adaptors are primed with primers having a 3'-poly(A) region. The primers hybridize with the hairpin adaptor portion such that the complementary region of the primer hybridizes to the hairpin adaptor while the poly(A) portion remains unhybridized and single stranded. The solution of primed SMRTbell™ templates is exposed to phi-29 polymerase under conditions in which the polymerase-nucleic acid complex forms. This step is generally carried out with an excess of polymerase e.g. 10:1 ratio of polymerase to template at 1 nM, or a 3:1 ratio of polymerase to template at 10 nM.

A solution of magnetic beads having attached poly(T) DNA (e.g. Dynal beads) is added to a tube. The beads are brought to the side of the tube with a magnet and rinsed with buffer, e.g. once with high salt, and once with a buffer similar to that used for sequencing. The polymerase-nucleic acid complex is then added to the beads at the appropriate level of dilution (e.g. 20 pM), and the beads are re-suspended into this solution. The beads are in contact with the solution to allow the poly(A) tails of the primers to hybridize to the poly(T) groups on the beads. The level of attachment of the complexes to the beads can be determined by fluorimetric methods.

The magnetic beads with polymerase-nucleic acid complex attached are then washed one to three times with buffer or salt solution. The wash steps remove unattached complex, unwanted components, and uncomplexed enzyme. In the last step, the magnetic beads with complex are dispersed into a sequencing reaction mixture. This solution can be stored for use, for example at 4° C., or can be dispensed directly onto a substrate. The solution can be dispensed onto a zmw chip having one or more permanent magnets below the chip, and the magnets moved with respect to the chip to move the beads across the surface. In some cases, no magnet is required and gravity is used to load the complexes onto the chip. The exposure to the chip can be, for example from 15 minutes to about 6 hours. The shorter times can provide higher throughput, while the longer times allow for the loading of lower concentrations of template, which can be useful where a minimal amount of sample is available.

Targeted Sequencing and Short Tandem Repeats

Although approximately 99.9% of human DNA sequences are the same in every person, enough of the DNA is different to distinguish one individual from another, unless they are monozygotic twins. DNA profiling can be done using repetitive ("repeat") sequences that are highly variable} referred to as variable number tandem repeats (VNTR). VNTRs loci are very similar between closely related humans, but so variable that unrelated individuals are extremely unlikely to have the same VNTRs.

A common method of DNA profiling with short tandem repeats (STR). uses PCR. The method uses highly polymorphic regions that have short repeated sequences of DNA (the most common is 4 bases repeated, but there are other lengths in use, including 3 and 5 bases). Because unrelated people almost certainly have different numbers of repeat units, STRs can be used to discriminate between unrelated individuals. These STR loci (locations on a chromosome) are targeted with sequence-specific primers and amplified using PCR. The DNA fragments that result are then separated and detected using electrophoresis. Each STR is polymorphic, however, the number of alleles is very small. Typically each STR allele will be shared by around 5-20% of individuals. The power of STR analysis comes from looking at multiple STR loci simultaneously. The pattern of alleles can identify an individual quite accurately. Thus STR analysis provides an excellent identification tool. The more STR regions that are tested in an individual the more discriminating the test becomes.

Figure 22:
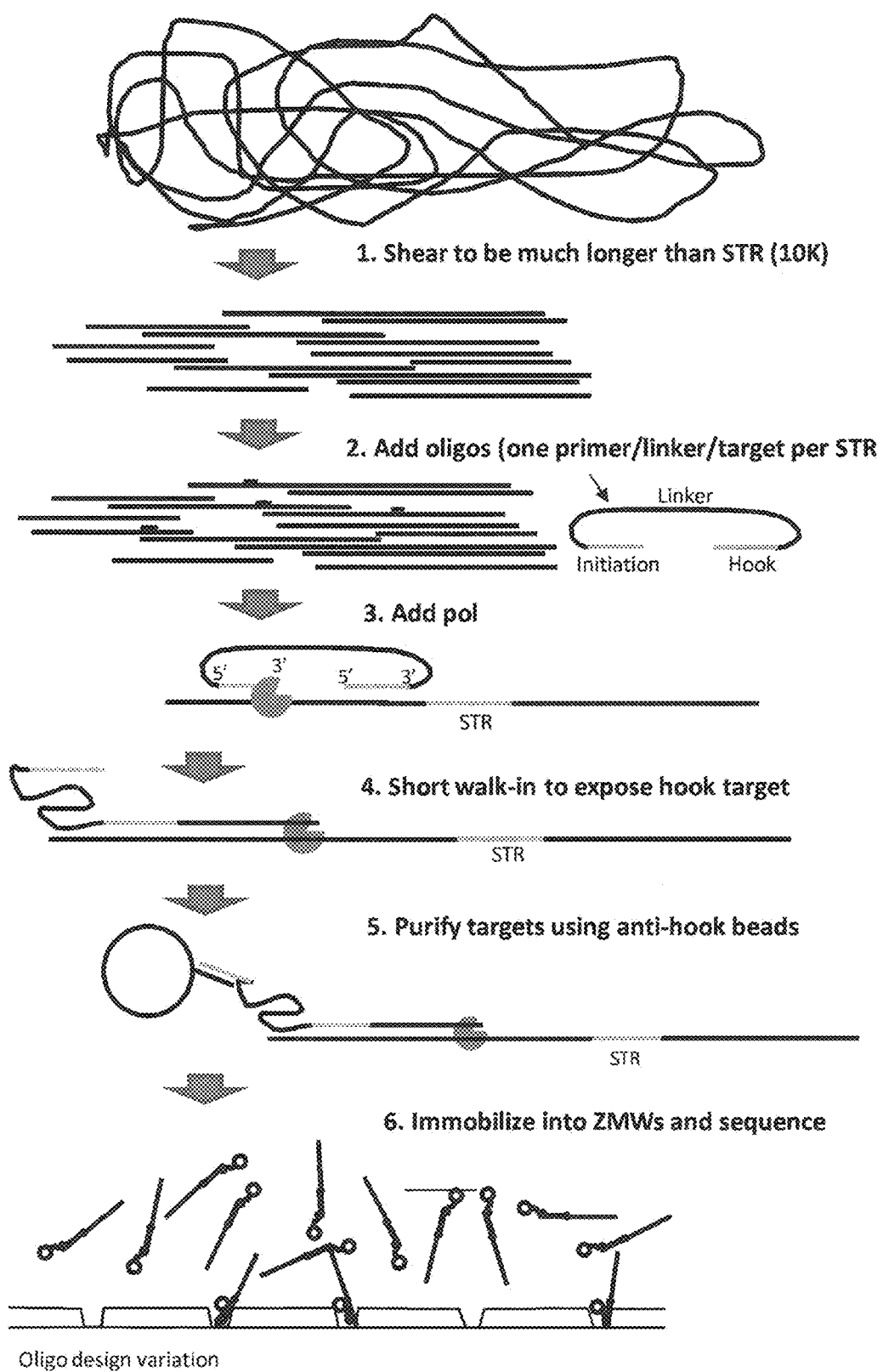
FIG. 22 is an outline of a method of using hook oligonucleotides and single molecule sequencing in order to measure short tandem repeats.

One aspect of the invention is a method of DNA profiling using hook oligonucleotides and the isolation of active enzyme complexes having specific portions of DNA. This is a resequencing application, so one knows a priori the relevant sequences for designing oligos to target the sequences. The regions of interest are well defined and relatively small in number. These method described below takes advantage of the versatility and granularity of single molecule real time sequencing. The methods described herein also can have a short time to result, which can be critical for this DNA profiling applications. Further, our lack of GC bias in SMRT real time sequencing facilitates reading through GC-rich regions including STRs. Since DNA fragments are measured at the single molecule level, other data including relative copy number between STRs and variation within a single STR, or heterogonous mutations are also available. An exemplary method is shown in FIG. 22. For sample prep, 1. Double stranded genomic DNA is sheared to a size amenable to ZMW loading by beads such as magnetic beads. The size can be, for example, on the order of 10 Kb. 2. Capture oligos, comprising initiation, linker and hook domains (of total length 20-100 bases), covering all desired STR regions, are added, the sample is heated and then slow cooled to facilitate binding. The oligos are designed such that the only 3' end available is at initiation site. 3. Polymerase is added and the "binding tube" is formed. 4. A short walk-in sufficient to knock off the hook region is completed. The short walk in can be accomplished by controlling the kinetics and time of polymerase activity (Sr, Ca, or short duration of Mg or Mn), or by using stop sites or regions. 5. Beads with the complementary sequence are added and used to pull-down properly formed and active complex 6. Sample is loaded into ZMWs and sequenced as described herein.

In some cases for improved coverage and accuracy, pairs of oligos per STR can be added, one for each strand, going in opposite directions. This would provide redundant information improving data quality.

Single-Strand SMRTbell Capture Using Modified Bases

One method of enriching a DNA sample for a specific DNA modification of interest (5-mC. 5-hmC, 8-oxoG, etc) is to use antibodies or specific binding proteins that are attached to beads to pull down regions of DNA containing the modification. Following capture, the region surrounding the DNA modification can be sequenced to identify the genomic region. SMRT DNA sequencing, in comparison to second generation sequencing methods, allows for direct detection of DNA modifications at single nucleotide resolution (Flusberg et al. Nature Methods 2010). Direct detection requires sequencing of the native DNA (non-amplified). Standard SMRTbell library preparation however, relies on double-stranded DNA. Furthermore, SMRTbells are less amenable to standard denaturing methods because they have a high propensity to re-anneal. However, it may be possible to make one strand of a SMRTbell stably single stranded using a DNA polymerase.

One aspect of the invention is a method of obtaining a single stranded template for capture by the following method. This single stranded region is then isolated using a pull-down method targeted to the modified bases. First, a DNA sample of interest that contains a specific modification (5-methyl C, for example) is obtained. The DNA is fragmented and converted into a SMRTbell library (circular DNA having central double stranded regions and single stranded hairpins on each end. Some portion of the SMRTbell molecules will contain the modification of interest. Capture methods using antibodies against 5-methyl C (for example) require that the DNA is single stranded.

To make a SMRTbell into a stably single stranded form, first a DNA polymerase (e.g. phi29) is bound to a SMRTbell that has been primer annealed onto its single stranded region using standard methods. The polymerase is given appropriate conditions to allow slow walking (e.g. calcium buffer) as described herein. The amount of time can be controlled and will depend on the size of the fragments in the SMRTbell library. Once the polymerase has made it about one half lap around the SMRTbell template (gone from one hairpin to the other hairpin), the polymerase is stopped using appropriate buffer conditions (i.e. strontium buffer) or an appropriate modification to the template that causes the polymerase to stop at the opposite hairpin. FIG. 23 shows how this process results in one strand of the SMRTbell being single stranded. This strand is now available for binding and pull-down. After pull down, the captured population of SMRTbells can be sequenced using standard SMRT™ sequencing methods. This type of sequencing can detect the sites of DNA modification using polymerase kinetics.

The walk-in can be controlled as described herein either by controlling the rate and time of the polymerase reaction, or by including sequence regions or modified bases in the hairpin region in order to cause the polymerase to stop. It will be understood that the modified bases that are exposed and pulled down in this method are generally different than the modified bases that are used to halt the polymerase within the hairpin region.

In some cases, the pull-down of the template with the modified base is carried out such that the polymerase remains active. When done in this manner, the isolated complex can be loaded into zero mode waveguides for sequencing. In some cases, the isolated templates comprising modified bases are separated from the polymerase enzyme used for walk-in. In addition the isolated template can be treated to remove the extended primer and re-generate the SMRTbell™. This can be done by annealing the sample to dissociate the extended primer. The removal of the extended primer can also be accomplished by treatment with exonuclease which will selectively degrade the single stranded portion, leaving the circular SMRTbell™ intact.

The modified bases can be any suitable modified nucleobase. The modified bases can be naturally occurring modified bases, which are present in many if not all organisms and are used, for example to regulate gene expression. The modified bases can also be non-natural modified bases such as those that occur due to synthetic chemical reactions or due to exposure to environmental factors such as ultraviolet light or oxygen. The modified bases include, for example, 5-methylcytosine, $N^6$-methyladenosine, etc.), pseudouridine bases, 7,8-dihydro-8-oxoguanine bases, 2'-O-methyl derivative bases, base J, base P, base Z, s4U, s6G, nicks, apurinic sites, apyrimidic sites, non-canonical bases or base pairs, pyrimidine dimers, a cis-platen crosslinking products, oxidation damage, hydrolysis damage, bulky base adducts, thymine dimers, photochemistry reaction products, interstrand crosslinking products, mismatched bases, secondary structures, and bound agents. Suitable modified bases are described, for example, in U.S. patent application Ser. No. 12/945,767, filed Nov. 10, 2010, the contents of which are incorporated by reference herein in its entirety for all purposes. Any binding protein or antibody that is specific for one or more of these modified bases can be used to isolate the template molecule containing these bases. Proteins that can be used to bind selectively to methylated sites include RNA and DNA polymerases, reverse transcriptases, histones, nucleases, restriction enzymes, replication protein A (RPA), single-stranded binding protein (SSB), RNA-binding proteins, microRNA-containing ribonucleoprotein complexes, anti-DNA antibodies, DNA damage-binding agents, modifying agents, agents that bind altered nucleotides (e.g., methylated), small RNAs, microRNAs, drug targets, etc.

There are a number of proteins that can bind stably and specifically to methylated DNA including members of the MBD family of human proteins, all of which contain a methyl-CpG binding domain (MBD). For example, MECP2, MBD1, MBD2, and MBD4 all bind specifically to methylated DNA, and are involved in repressing transcription from methylated gene promoters. Binding of these proteins to a template nucleic acid is expected to cause a translocating polymerase to pause proximal to the bound protein. As such, an increased pause duration during single-molecule sequencing reactions is indicative of a methylated base in the template nucleic acid. It is therefore important that the protein bind tightly to its target nucleic acid sequence. Natural MBD proteins only have micromolar Kd affinities for methyl-CpG sequences, so engineered MBD proteins that bind more tightly to the methylated template sequence can enhance detectability of methylated bases. For example, a multimerized MBD1 protein is provided in Jorgensen, et al., *Nucleic Acids Research* 2006, 34(13), e96. Such engineered proteins can have a single methyl binding domain with a lower Kd (sub-micromolar) or multiple methyl-binding domains that increase the effective concentration of the methyl-binding domain in the vicinity of the methylated DNA template. More information on the MBD family of proteins is provided, e.g., in B. Hendrich, et al., *Mol Cell Biol* 1998, 18(11), 6538; and I. Ohki, et al., *EMBO J* 2000, 18(23), 6653.

In addition, the mammalian UHRF1 (ubiquitin-like, containing PHD and RING finger domains 1) protein binds tightly to methylated DNA and is required for its maintenance. Crystal structures of the SRA domain of this protein bound to DNA show that the 5-MeC is flipped out of the DNA duplex and stabilized by hydrophobic stacking and hydrogen bonding to SRA protein residues. (See, e.g., G. V. Avvakumov, et al. and H. Hashimoto, et al., both supra.) Further, McrBC is an endonuclease that cleaves DNA containing 5-methylcytosine or 5-hydroxymethylcytosine or N4-methylcytosine on one or both strands, but does not act upon unmethylated DNA. McrBC requires GTP for cleavage, but in the presence of a non-hydrolyzable analog of GTP, the enzyme will bind to methylated DNA specifically, without cleavage. (See, e.g., Irizarry, R. A. et al. (2008) *Genome Res.*, 18, 780-790; and Hublarova, P. et al. (2009) *Int J Gynecol Cancer*, 19, 321-325, the disclosures of which are incorporated herein by reference in their entireties for all purposes.) Finally, the monoclonal antibody to 5-MeC, used for methylated DNA immunoprecipitation, also binds specifically to methylated cytosine. (See, e.g., N. Rougier, et al., *Genes Dev* 1998, 12, 2108; and M. Weber, et al., supra, which are incorporated herein by reference in their entireties for all purposes.)

In yet further embodiments antibodies can be used to target the specific modified bases. For example, an antibody against 5-MeC could be used to bind 5-MeC in a template nucleic acid, similar to the process used in methylated DNA immunoprecipitation assays (M. Weber, et al., *Nat Genet.* 2005, 37, 853).

Thus, in some aspects, the invention provides methods for isolating DNA having a modified or unnatural base comprising: obtaining a library of circular DNA fragments each comprising a double stranded DNA central region and single stranded regions on the ends of the double stranded regions wherein at least some of the fragments comprise a modified or unnatural base; treating the DNA fragments with a primer and a polymerase under conditions where the polymerase extends the primer to copy at least one of the strand of the double stranded region so as to render the other strand of the double-stranded portion single stranded; using a binding protein or antibody that is specific to the modified or unnatural base to isolate strands containing the modified or unnatural bases from those that do not contain the unnatural or modified bases. In some embodiments, the modified or unnatural base is methyl-C, hydroxy-methyl C, or oxo-G.

EXAMPLES

Example 1

Hook Capture Using a Common Hook

Polymerase—SB Template Complex Formation:

Several types of SMRTBell™ (SB) templates having the common (VD) Adaptor 5% TCTCTCTCTTTTCCTCCTCCTCCGTTGTTGTTGTTGAGAGAGAT-3' (SEQ ID NO: 1) (FIG. 10(A)), 2k (Phix3-12), 1k (PhiX9-16), 0.6 k (Bsub1), and 2k λ-library, were individually mixed with SA-Pol (3029P) for the Pol-template binding tubes. The condition for the binding was: 3 nM SB template, 15 nM SA-Pol, 50 mM Tris acetate, pH 8.0, 0.05% (v/v) Tween-20, 20 mM potassium acetate, 0.2 mM calcium acetate, 1 µM each dNTP, and 100 mM DTT. Volume in each tube was either 0.2 mL or 1 mL. These tubes were incubated at 22° C. for approximately 16 hours. To each tube, 0.05 volume of 20 mM Strontium acetate (10 µL Sr for 200 µL tube) was added.

Samples for Enrichment:

Sample 1: A mixture of 143 pM Pal-2k SB (PhiX3-12) and 2857 pM Pol-0.6 k SB (Bsub1).

Sample 2: A mixture of 136 pM Pol-2k SB (PhiX3-12), 136 pM Pol-1k SB (PhiX9-16) and 2723 pM Pol-0.6k SB (Bsub1).

Sample 3: A mixture of 150 pM Pol-2k SB (PhiX3-12) and 3000 pM Pol-2k λ-library.

Sample 4: A mixture of 110 pM Pol-2k SB (PhiX3-12), 2800 pM Pol-0.6 k SB (Bsub1) and 2300 pM Pol-2k λ-library.

Figure 10:
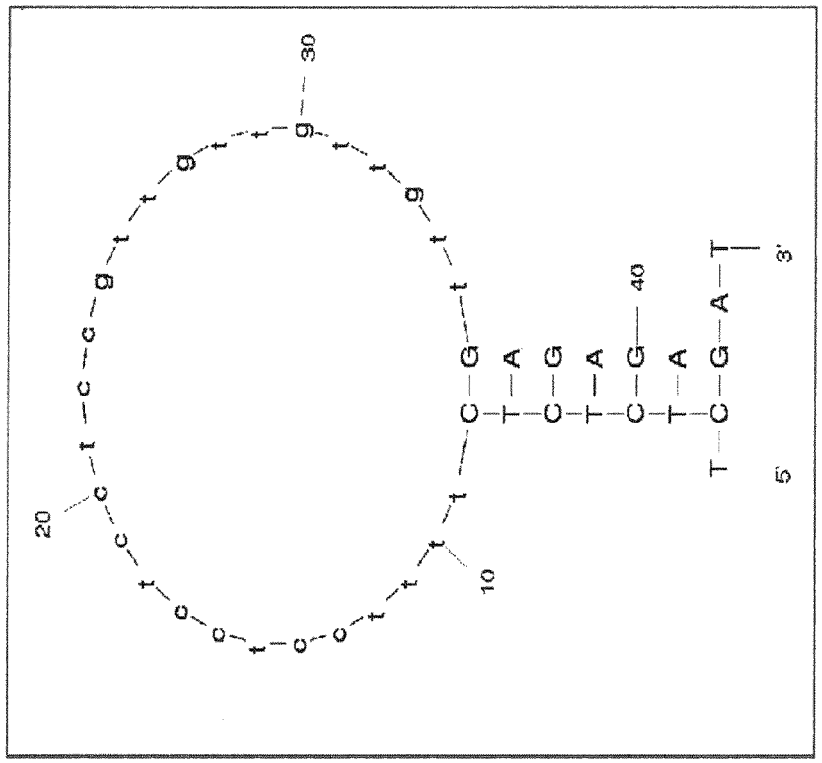
FIG. 10(A) shows the structure of a representative hairpin adaptor for producing SMRTBell™ templates, the structure of a hook oligonucleotide targeting a portion of the hairpin adaptor.
FIG. 10(B) provides a table showing some calculated melting temperatures for oligonucleotide hybridization.

Bead-Based Purification of Active Complexes:

Samples 1 and 2 were diluted in an equal volume of BBB (50 mM Tris acetate, pH 8.0, 0.05% (v/v) Tween-20, 100 mM potassium acetate, 1 mM strontium acetate, 0.5 µM each dNTP, and 10 mM DTT). Heparin (Sigma, cat #114784) was added to final concentration of 1 mg/mL. The tubes were incubated for 10 min at 22 C and 30 min on ice. Potassium acetate was added to the final concentration of 0.1 M. The "VD-hook" oligo was added at 20-fold higher of hook concentration than the SB template concentration. (VD-hook: 5'-TCTCTCTCAACAA(A)23-3' (SEQ ID NO: 2). The tubes were incubated at 4° C. for 2 to 16 hr. FIG. 10 (B) shows a table with calculated melting temperatures for hybridized oligonucleotides at various salt concentrations. It can be seen, for example, that the melting temperature of the specific 13-mer portion of the VD-hook can be varied over a wide range of melting temperatures by changing the salt concentration. The table also shows some calculated melting temperatures for 20mer and 15mer poly A oligonucleotides. By changing the length of the poly(A) on the retrieval part of the oligonucleotide, the relative strength of these links can be controlled. Generally, the smaller difference between the melting temperature and the sample temperature, the weaker the bond. As described above, the hook oligo can be designed such that the bond between the capture portion of the hook oligonucleotide and the template nucleic acid is stronger than the bond between the retrieval portion of the hook oligonucleotide and the bead.

Oligo (dT)25 magnetic beads from New England Biolabs (cat #S1419S) was washed and equilibrated in BBB. For each volume (µL) of sample containing 200 fmoles of hook oligo, 1 µL of beads was used. The samples with beads were mixed well and kept on ice for 1 hour. The beads were pulled to the side of tube using a magnetic stand (Invitrogen), the liquid was discarded. Then 0.2 mL of cold BBB was added to each tube, and the beads were mixed well. Again, the beads were pulled to the side of tube using a magnetic stand, and the liquid was discarded. The beads were washed with BWB2 (50 mM Tris acetate, pH 8.0, 0.05% (v/v) Tween-20, 400 mM potassium acetate, 1 mM strontium acetate, 0.5 µM each dNTP, and 10 mM DTT), and then with BBB. The purified active Pol-template complexes were eluted in BEB (50 mM Tris acetate, pH 8.0, 0.05% (v/v) Tween-20, 10 mM potassium acetate, 1 mM strontium acetate, 0.5 µM each analog (dye-dN6P), and 10 mM DTT). The tubes were incubated at 30° C. for 10 min; they were immediately placed on a magnetic stand and the liquid fractions containing the purified active Pol-template complexes were transferred to new tubes.

The DNA concentrations of the purified complexes were determined by a fluorescent assay using a kit (Quant-iT™ DNA Assay Kit, High Sensitivity from Invitrogen).

4-Color Single Molecule Sequencing:

The purified complexes were used for single molecule sequencing according to the method described in Eid et al., Science Vol. 323 no. 5910 pp. 133-138 (January 2009).

Example 2

Hook Capture for Enrichment of Specific Sequences

Polymerase—SB Template Complex Formation:

Several types of SB templates, 2k (Phix3-12), 1k (PhiX9-16), 0.6 k (Bsub1), and 2k λ-library, were individually mixed with SA-Pol (3029P) for the Pol-template binding tubes. The condition for the binding was: 3 nM SB template, 15 nM SA-Pol, 50 mM Tris acetate, pH 8.0, 0.05% (v/v) Tween-20, 20 mM potassium acetate, 0.2 mM calcium acetate, 1 µM each dNTP, and 100 mM DTT. Volume in each tube was either 0.2 mL or 1 mL. These tubes were incubated at 22° C. for approximately 16 hours. To each tube, 0.05 by volume of 20 mM Strontium acetate (10 µL Sr for 200 µL tube) was added.
Samples for Enrichment:

Sample 1: A mixture of 143 pM Pol-2k SB (PhiX3-12) and 2857 pM Pol-0.6 k SB (Bsub1).

Sample 2: A mixture of 136 pM Pol-2k SB (PhiX3-12), 136 pM Pol-1k SB (PhiX9-16) and 2723 pM Pol-0.6 k SB (Bsub1).

Sample 3: A mixture of 150 pM Pol-2k SB (PhiX3-12) and 3000 pM Pol-2k λ-library.

Sample 4: A mixture of 110 pM Pol-2k SB (PhiX3-12), 2800 pM Pol-0.6 k SB (Bsub1) and 2300 pM Pol-2k λ-library.
Bead-Based Purification of Active Complexes:

Samples 1 and 2 were diluted an equal volume of BBB (50 mM Tris acetate, pH 8.0, 0.05% (v/v) Tween-20, 100 mM potassium acetate, 1 mM strontium acetate, 0.5 µM each dNTP, and 10 mM DTT). Heparin (Sigma, cat #H4784) was added to final concentration of 1 mg/mL. The tubes were incubated for 10 min at 22 C and 30 min on ice. Potassium acetate was added to the final concentration of 0.1 M. The specific "hook" oligo was added at 20-fold higher of hook concentration than the SB template concentration. (2k-L-hook: 5'-AATGCTTACTCAAG(A)23-3'(SEQ ID NO: 3; 2k-R-hook: 5'-ATGAAGTAATCACG(A)23-3'(SEQ ID NO: 4)). The tubes were incubated at 4° C. for 2 to 16 hr.

Oligo (dT)25 magnetic beads from New England Biolabs (cat #S1419S) were washed and equilibrated in BBB. For each volume (µl) of sample containing 200 fmoles of hook oligo, 1 µL of beads was used. The samples with beads were mixed well and kept on ice for 1 hour. The beads were pulled to the side of tube using a magnetic stand (Invitrogen), and the liquid was discarded. Then 0.2 mL of cold BBB was added to each tube, the beads were mixed well. Again, the beads were pulled to the side of tube using a magnetic stand, liquid was discarded. The beads were washed with BWB2 (50 mM Tris acetate, pH 8.0, 0.05% (v/v) Tween-20, 400 mM potassium acetate, 1 mM strontium acetate, 0.5 µM each dNTP, and 10 mM DTT), and then with BBB. The purified active Pol-template complexes were eluted in BEB (50 mM Tris acetate, pH 8.0, 0.05% (v/v) Tween-20, 10 mM potassium acetate, 1 mM strontium acetate, 0.5 µM each analog (dye-dN6P), and 10 mM DTT). The tubes were incubated at 30° C. for 10 mM; then they were immediately placed on a magnetic stand and the liquid fractions containing the purified active Pol-template complexes were transferred to new tubes.

The DNA concentrations of the purified complexes were determined by a fluorescent assay using a kit (Quant-iT™ DNA Assay Kit, High Sensitivity from Invitrogen).

Figure 11:
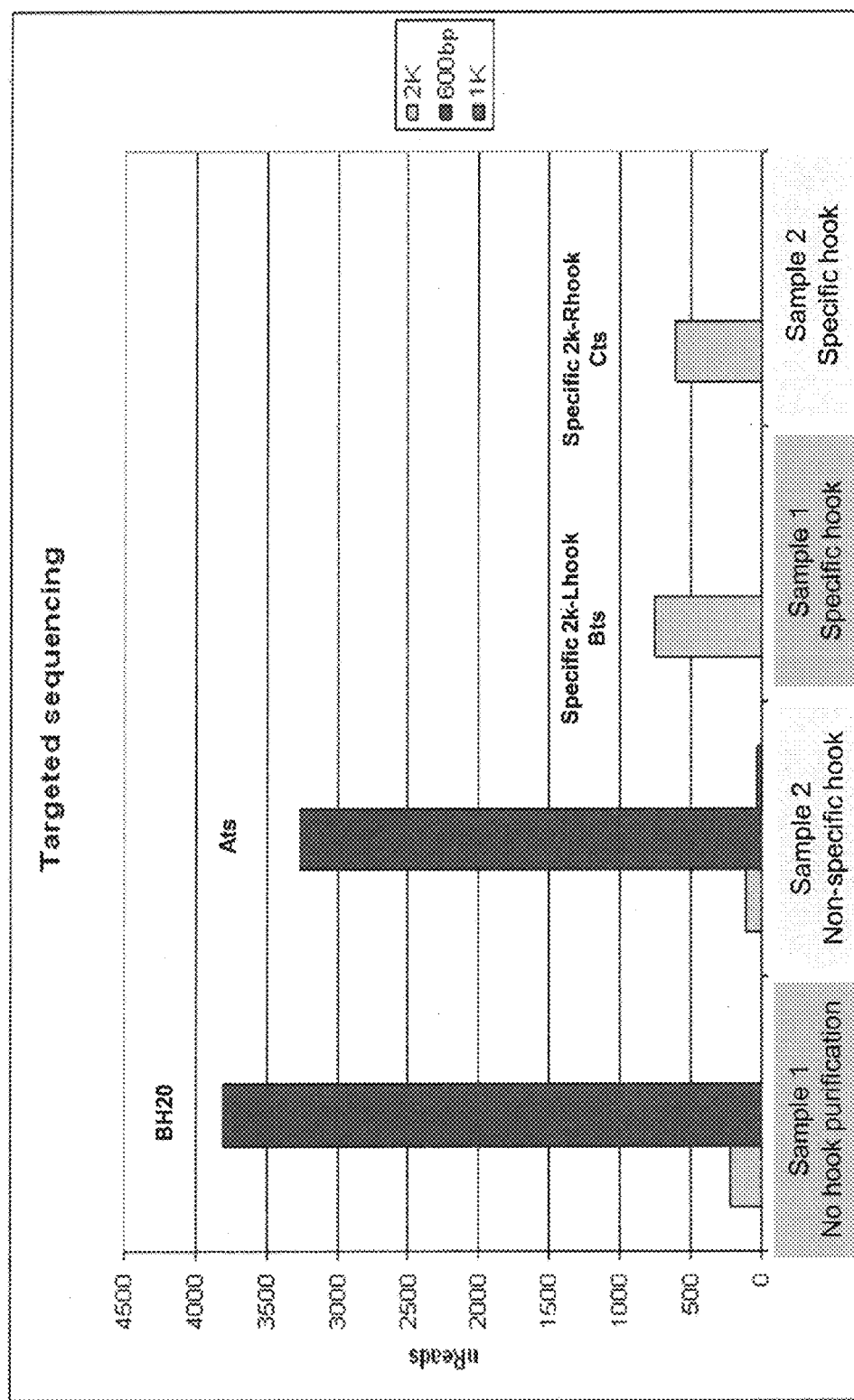
FIG. 11 shows a plot of the number of sequencing reads for samples having a mixture of templates illustrating the ability of a specific hook oligonucleotide to capture and enrich a sequence in the presence of other nucleotides which do not have the sequence.

4-Color Single Molecule Sequencing:

The purified complexes were used for single molecule sequencing according to the method described in Eid et al., Science Vol. 323 no. 5910 pp. 133-138 (January 2009).
Results:

The yields of specifically sequenced templates from Sample 1 (2 templates) and Sample 2 (3 templates) were compared. FIG. 11 graphically displays some of the results, showing the sequencing yield (number of reads or nReads) for Sample 1 with no hook purification, Sample 2 with a common hook purification, Sample 1 purified using a hook molecule targeted to one region of 2k SB (PhiX3-12) (2k-L-hook), and Sample 2 purified using a hook molecule targeted to another region of 2k SB (PhiX3-12) (2k-R-hook). The enrichment of the 2k SB (PhiX3-12) using specific hooks targeting this template is compared to using a common hook molecule targeting all 3 templates (the VD-hook). Sample 1 has 20-fold excess of 0.6 k SB (Bsub1); the purified sample 1 using specific hook for 2k SB (PhiX3-12) showed 300-fold more reads of 2k SB than the number of reads for 0.6 k SB. Therefore, the enrichment of 2k SB for sample 1 is about 6000-fold.

Figure 12:
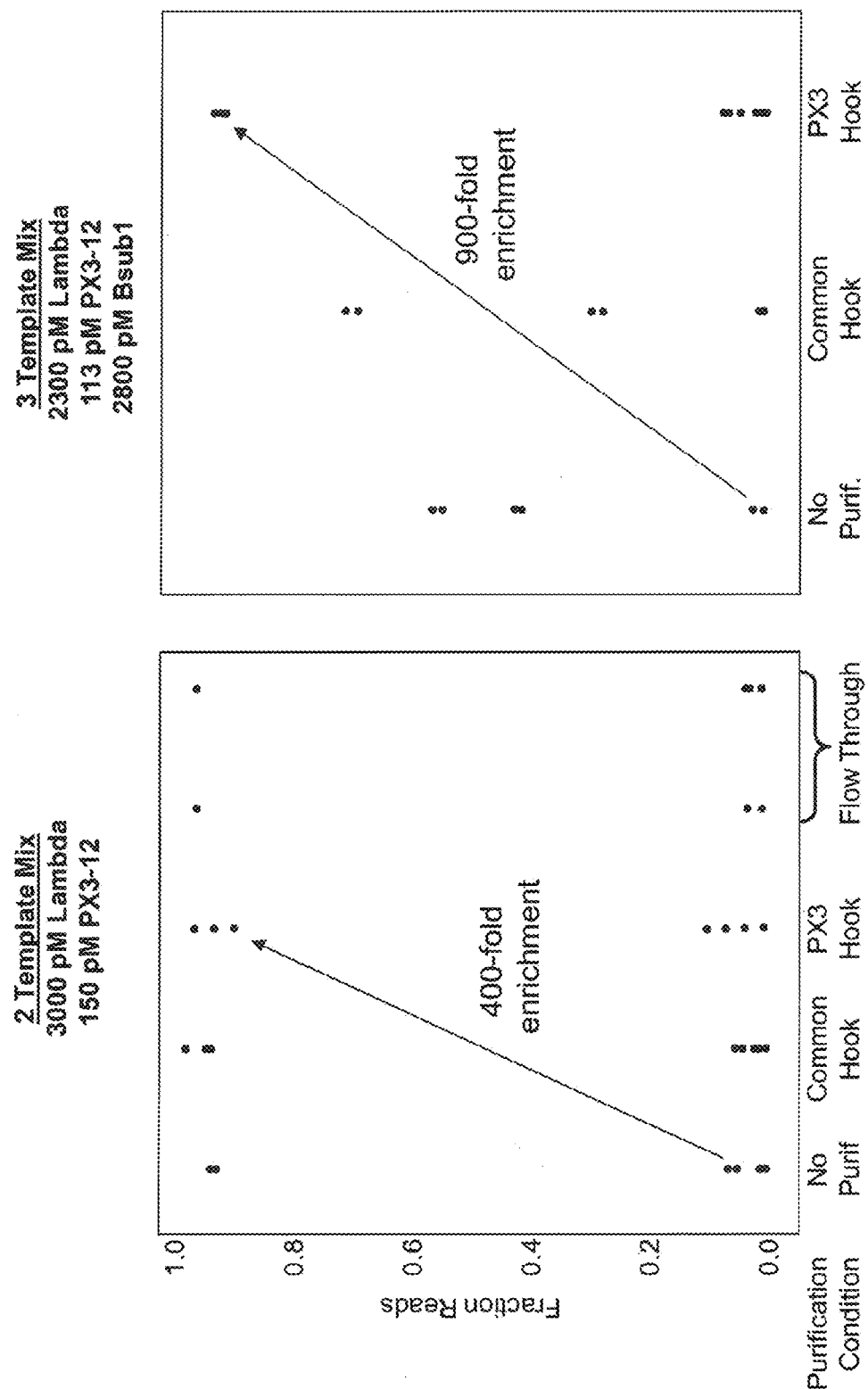
FIG. 12 is a plot showing how a specific hook molecule can be used to enrich the representation of the template nucleic acid to which it is targeted.

FIG. 12 compares the relative yield (fraction Reads) of specifically sequenced templates from Sample 3 (2 template types) and Sample 4 (3 template types). The enrichment of the 2k SB (PhiX3-12) using a specific hook targeting this template is compared to using the common VD-hook targeting all 3 templates. Sample 3 has 20-fold excess of 2k λ-library of SB; the purified sample 3 using specific hook for 2k SB (PhiX3-12) showed 20-fold more reads of 2k SB (phiX3-12) than the number of reads for 2k λ-library SB. Therefore, the enrichment of 2k SB for sample 3 is about 400-fold. Sample 4 has ~49-fold less of 2k SB (PhiX3-12) than the numbers of 2k λ-library plus 0.6 k SB (Bsub1); the bead-purified sample 4 using specific hook for 2k SB (PhiX3-12) showed ~19-fold more reads of 2k SB (phiX3-12) than the number of reads for 2k λ-library and Bsub1 SB. Therefore, the enrichment of 2k SB for sample 4 is about 900-fold.

Example 3

Deposition of Polymerase-Nucleic Acid Complexes with Magnetic Beads

A SMRTBell™ (SB) template, 2k (Phix3-12), was mixed with SA-Pol (3029P) for the Pol-template binding tubes. The condition for complex binding was: 3 nM SB template, 9 nM SA-Pol, 50 mM Tris acetate, pH 8.0, 0.05% (v/v) Tween-20, 20 mM potassium acetate, 0.2 mM calcium acetate, 1 µM each dNTP, and 100 mM DTT. The volume of the tube was 0.2 mL. The tube was incubated at 30° C. for 4 hours and subsequently kept at 4° C. until ready for testing (typically within 12 hours). The contents of the tube were then split into two separate tubes of equal volume, 0.1 mL each. One tube (Sample 1) served as the control and no further modifications were made. The other tube (Sample 2) was hooked to magnetic beads in the following manner.
Sample Hook:

Heparin (Sigma, cat #H4784) was added to Sample 2 to a final concentration of 1 mg/mL and Sr was added to a final concentration of 1 mM. The tube was incubated for 30 min on ice. Heparin was employed to trap free polymerase and Sr served to stop the "walk-in" of the polymerase on the DNA template. Potassium acetate was then added to a final concentration of 0.1 M and the "hook" oligo was added at a concentration of 60 nM. The sample tube was incubated at 4° C. for 16 hrs. This sample (Hooked Sample 2) was now ready for bead attachment.

Bead Preparation and Attachment:

In a separate tube, 80 uL of oligo (dT)25 magnetic beads from New England Biolabs (eat #S1419S) were washed and equilibrated in BBB. The beads were pulled to the side of tube using a magnetic stand (Invitrogen) and the liquid was discarded. Then, 0.1 mL of Hooked Sample 2 was added to the bead tube and mixed well. The Hooked Sample 2 and beads were stored @ 4 C for 1 hr to allow for attachment. Then newly complexed beads were purified in three subsequent steps. Purification step 1: The beads were pulled to the side of tube using a magnetic stand, and the liquid was discarded. Purification step 2: The beads were washed with BWB2 (50 mM Tris acetate, pH 8.0, 0.05% (v/v) Tween-20, 400 mM potassium acetate, 1 mM strontium acetate, 0.5 µM each dNTP, and 10 mM DTT). Purification step 3: Repeat of step 1. After purification, the beads were pulled to the side of tube using a magnetic stand, the liquid was discarded, and the complexed beads were resuspended in BBB at 0.07 mL final volume, after which and this sample (Complexed Bead Sample) was ready for testing.

Prior to loading onto the surface of a ZMW array chip, both the Sample 1 Control (S1C) and the Complexed Bead Sample (CBS) were diluted to desired concentrations in BBB. ZMW array chips were prepared for sample loading by priming 2× with 25 uL of 50 mM MOPS pH7.5. For each sample, a 25 uL aliquot of diluted sample was pipetted onto the primed chip surfaces and the aliquot was incident for a total loading time of 5 minutes. The S1C sample loaded by diffusion and no further modifications were necessary. For the CBS, magnetic loading was employed, where a permanent magnet was passed under the sample at an approximate rate of 1 pass/10 s. In this manner, the beads can be seen traversing the array surface with each pass. After 5 minutes, the aliquots were removed and the chip was washed 5× in a wash buffer (50 mM Tris acetate, pH 8.0, 100 mM KOAc, 40 mM DTT). Following washing, reagents for DNA sequencing were placed on the chip and a sequencing run was performed to assess the loading of the ZMW arrays. Loading activity was quantified using the percentage of ZMWs that showed statistically significant sequencing activity (Z>3) via alignments to the reference DNA template when sequenced by the method described by Eid, J. et al., Science, 323(5910), 133-138 (2009).

Figure 13:
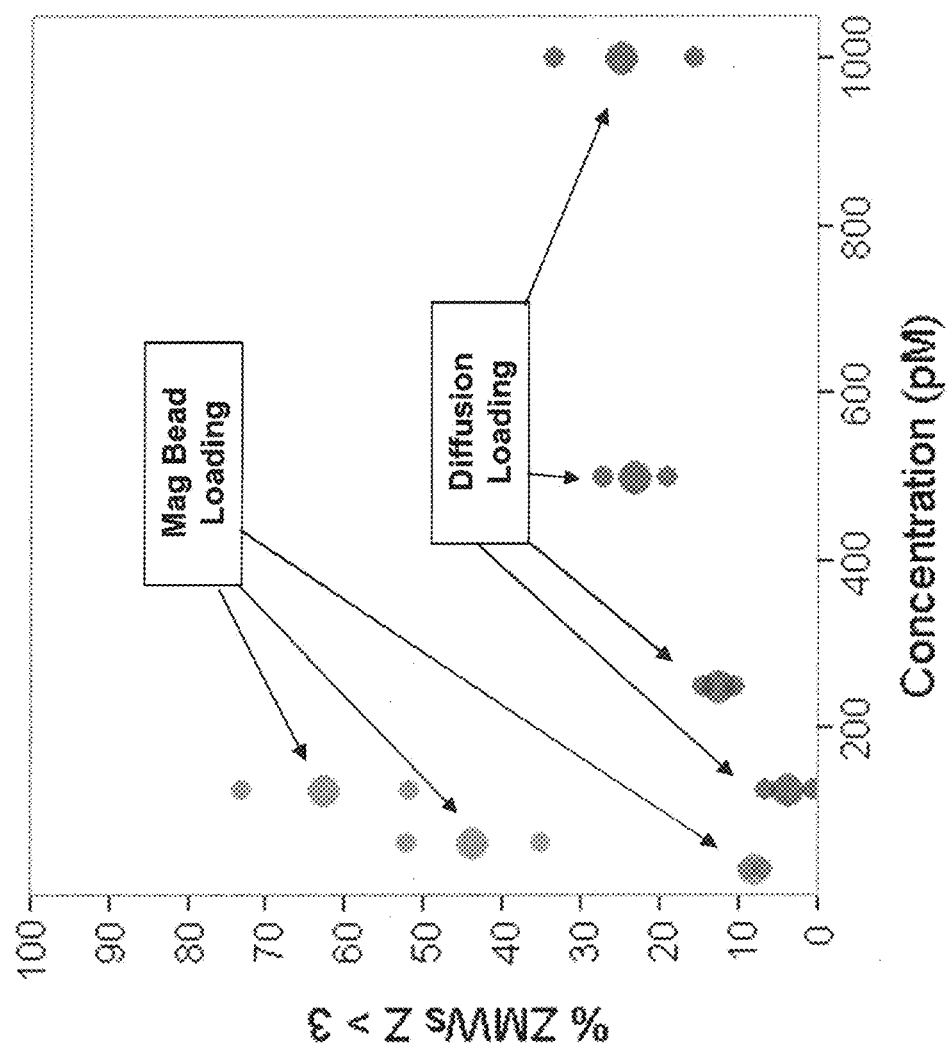
FIG. 13 provides sequencing data showing how magnetic loading of polymerase-nucleic acid templates can be more effective than for diffusion loading.

FIG. 13 shows a comparison of loading between the magnetic bead and diffusion loading. Magnetic bead loading results in higher loading for a given amount of input DNA. At an identical DNA concentration (150 pM), the bead loading is 20× more efficient than diffusion.

Example 4

Higher Representation of Large Templates when Loading of Polymerase-Nucleic Acid Complexes with Magnetic Beads Experimental Procedure:

A synthetic library was made from pCYPAC2 (18.7 kbp), where the organism DNA was cut into strands of varying length and subsequently made into SMRTbells as described above. The SB ranged in size from 160 bp to 4251 bp. The synthetic library was mixed with SA-Pol (3029P) for the Pol-template binding tubes. The condition for complex binding was: 3 nM SB template, 9 nM SA-Pal, 50 mM Tris acetate, pH 8.0, 0.05% (v/v) Tween-20, 20 mM potassium acetate, 0.2 mM calcium acetate, 1 µM each dNTP, and 100 mM DTT. The volume of the tube was 0.2 mL. The tube was incubated at 30° C. for 4 hours and subsequently kept at 4° C. until ready for testing (typically within 12 hours). The contents of the tube were then split into two separate tubes of equal volume, 0.1 mL each. One tube (Sample 1) served as the control and no further modifications were made. The other tube (Sample 2) was hooked to magnetic beads in the following manner.

Sample Hook:

Heparin (Sigma, cat #H4784) was added to Sample 2 to a final concentration of 1 mg/mL and Sr was added to a final concentration of 1 mM. The tube was incubated for 30 mM on ice. Heparin was employed to trap free polymerase and Sr served to stop the "walk-in" of the polymerase on the DNA template. Potassium acetate was then added to the final concentration of 0.1 M and the "hook" oligo was added at a concentration of 60 nM. The sample tube was incubated at 4° C. for 16 hrs. This sample (Hooked Sample 2) was now ready for bead attachment.

Prior to loading onto the surface of a ZMW array chip, both the Sample 1 Control (SIC) and the Complexed Bead Sample (CBS) were diluted to desired concentrations in BBB. ZMW array chips were prepared for sample loading by priming 2× with 25 uL of 50 mM MOPS pH7.5. For each sample, a 25 uL aliquot of diluted sample was pipetted onto the primed chip surfaces and the aliquot was incident for a total loading time of 5 minutes. The S1C sample loaded by diffusion and no further modifications were necessary. For the CBS, magnetic loading was employed, where a permanent magnet was passed under the sample at an approximate rate of 1 pass/10 s. In this manner, the beads can be seen traversing the array surface with each pass. After 5 minutes, the aliquots were removed and the chip was washed 5× in a wash buffer (50 mM Tris acetate, pH 8.0, 100 mM KoAc, 40 mM DTT). Following washing, reagents for DNA sequencing were placed on the chip and a sequencing run was performed to assess the loading of the ZMW arrays. Loading activity was quantified using the percentage of ZMWs that showed statistically significant sequencing activity (Z>3) via alignments to the reference DNA template.

Figure 14:
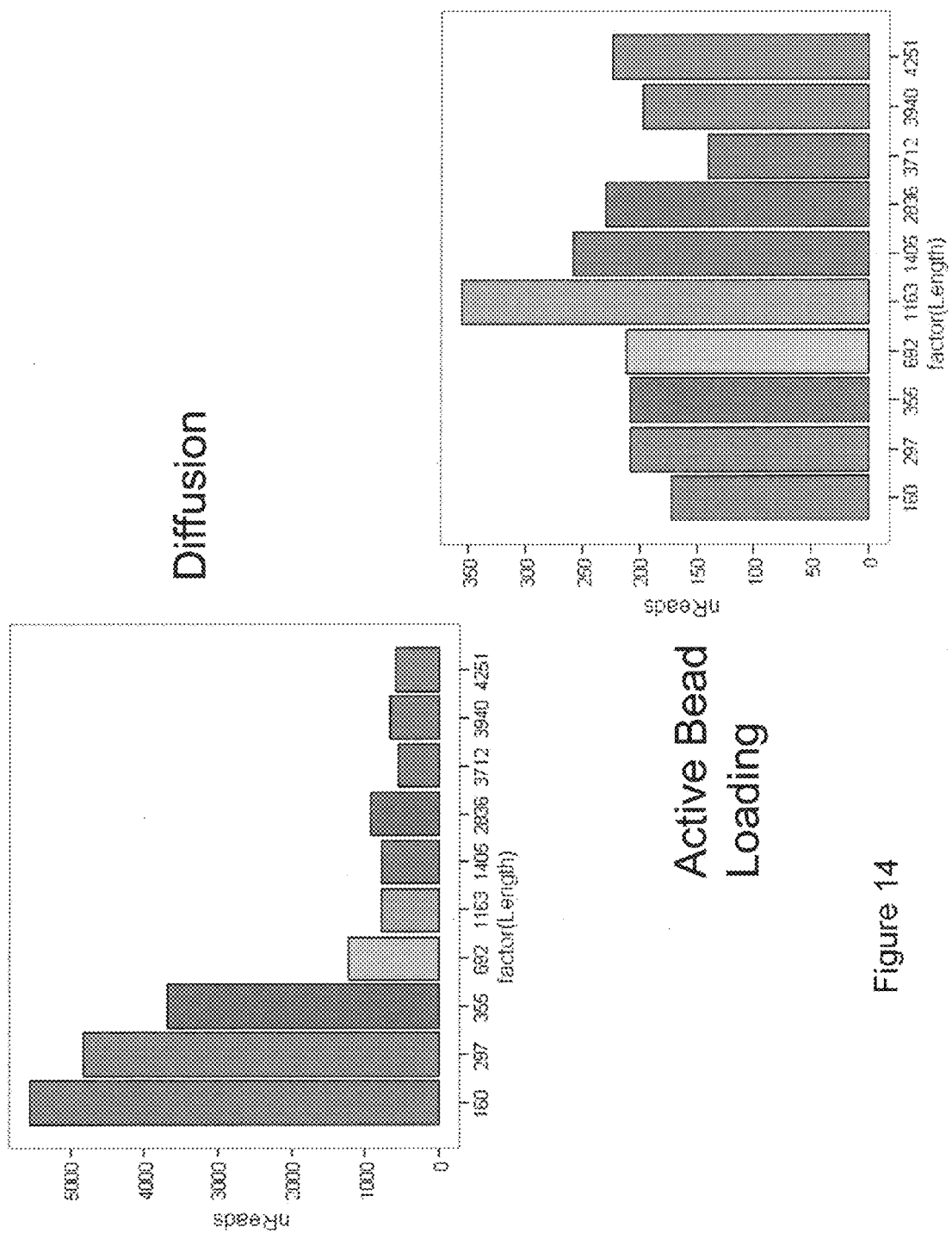
FIG. 14 shows that bead loading can provide a more even representation of sequence versus the size of the template, where for diffusion, smaller templates tend to be more highly represented.

FIG. 14 shows a comparison of loading between the magnetic bead and diffusion loading. Diffusion loading has a distinct bias towards loading smaller templates. In contrast, magnetic bead loading shows relatively even loading for all tested template sizes.

Example 5

Re-Use of Polymerase-Nucleic Acid Complexes on Magnetic Beads

Complexed Bead Samples were prepared in the manner as described above. Magnetic loading was employed, where a permanent magnet was passed under the sample at an approximate rate of 1 pass/10 s. In this manner, the beads can be seen traversing the array surface with each pass. After 5 minutes, the beads were removed and transferred onto a new freshly primed chip. The loaded chip was washed 5× in a wash buffer (50 mM Tris acetate, pH 8.0, 100 mM KoAc, 40 mM DTT). Following washing, reagents for DNA sequencing were placed on the chip and a sequencing run was performed to assess the loading of the ZMW arrays. This process was repeated 5× to assess the re-useability of the complexed bead samples. Loading activity was quantified using the percentage of ZMWs that showed statistically significant sequencing activity (Z>3) via alignments to the reference DNA template.

Figure 15:
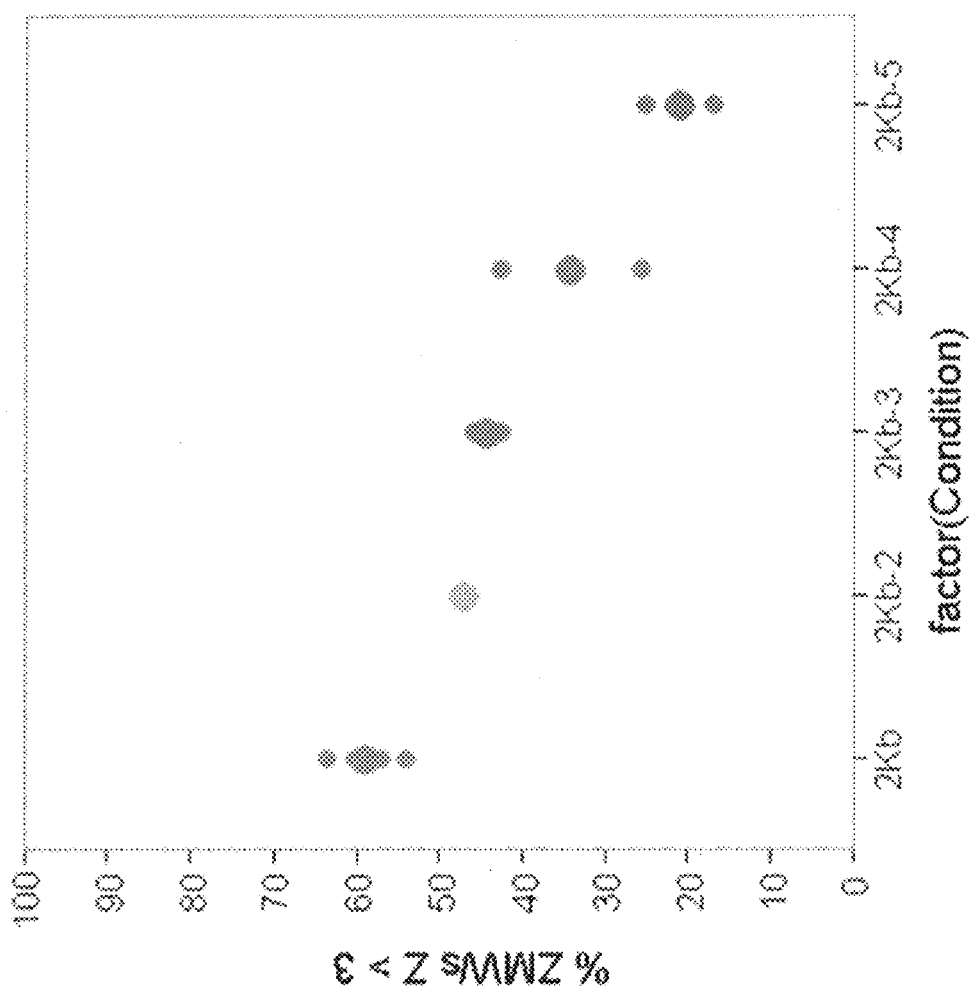
FIG. 15 shows data indicating that magnetic beads having polymerase-nucleic acid complexes attached can be re-used multiple times to deposit the complexes on substrates.

FIG. 15 shows that complexed bead samples can be re-used several times with a small loss in loading efficiency. Each re-use of complexed bead samples shows a loading efficiency loss of approximately 10%.

Example 6

Producing and Retrieving a Linear Double Stranded Template Having a Gap in One Strand A population of DNA fragments having blunt ends is produced by shearing a DNA sample and polishing the fragments to form blunt ends. The blunt ended fragments are then ligated to the linear adaptor below:

```
5'- CAACGGAGGAGGAGG-3'

5'-GGACCACCTCCTGAGAGAGAGA-3'

3'- NGTTGCCTCCTCCTCCNNNNNNNNNNNTGGTGGAGGACTCTCTCTC
T-5'

Made up of oligos:
                                        (SEQ ID NO: 5)
5'- CAACGGAGGAGGAGG-3'

(SEQ ID NO: 6)
5'-GGACCACCTCCTGAGAGAGAGA-3'

(SEQ ID NO: 7)
5'-TCTCTCTCTCAGGAGGTGGTNNNNNNNNNNNCCTCCTCCTCCGTTGN-
3'
```

For this sequence, "N" can be either A, C, G or T as this sequence is not important for hybridization of the oligos involved. Generally, the poly N region is designed such that it will not hybridize to the capture sequence of a hook oligonucleotide. It is also designed such that it will not be complementary to any of the three oligonucleotides that make up the linear adaptor.

To the resulting library of fragments is added a phi-29 DNA polymerase enzyme in excess under conditions whereby binding of the polymerase enzyme to the fragments occurs. Nucleic acid synthesis is initiated such that the polymerase enzyme produces a growing strand from the 3' position within the gap, displacing the strand ahead of it. Nucleic acid synthesis is halted by the addition of a solution of Sr ions. A hook oligonucleotide having the structure below:

```
    5'-AGGAGGTGGTCC(A)23 -3'    (SEQ ID NO: 8)
``` having a 5' end that is complementary to a portion of the displaced strand in the active complexes is added under conditions providing for selective hybridization. Magnetic beads having bound poly(T) oligonucleotides are added to bind to the poly(A) region of the hook oligonucleotide. Permanent magnets are used to hold the magnetic beads in place while wash solutions are used to remove components of the mixture not bound to the beads. The isolated polymerase-nucleic acid complexes can then be deposited onto substrates for single molecule analysis, either by eluting the complexes from the beads using the appropriate levels of salt and temperature and exposing the eluted complexes to the substrates; or by contacting the magnetic beads having polymerase-nucleic acid complex bound thereto with the substrates using magnetic fields.

Example 7

Purifying Polymerase-Nucleic Acid Complex Using a Single Stranded Region

Annealing of a Poly-A Tailed Primer to SMRTbell™ Template

An oligonucleotide primer is annealed to both hairpins of a SMRTbell template. The primer consists of a 5' polyA-tract and 3' region complementary to the SMRTbell hairpin. The annealing reaction is assembled in a buffer solution consisting of 50 mM Tris-Acetate ("TOAc"), 20 mM Potassium Acetate ("KOAc"), and 0.05% Tween-20. The primer is provided at approximately twice the molar concentration of the template.

Binding Polymerase to SMRTbell Template

Primed SMRTbell templates are combined with nucleotides, an inhibitory metal cation (Calcium or Strontium), DTT, and the DNA polymerase to be used for single-molecule sequencing. The polymerase is typically provided at several fold higher concentration than the template, to ensure binding of active polymerase molecules at all priming sites. The binding reaction is incubated at 30° C. for 30-240 minutes.

Complex Purification Via Primer Capture

Polymerase-bound SMRTbell molecules (ternary "complexes") are prepared for bead purification by the addition of heparin (to bind free polymerase) and adjustment of salt concentration to 100 mM KOAc (for optimal nucleic acid hybridization while maintaining polymerase-SMRTbell binding), and incubated for 15-30 minutes on ice. Commercially available magnetic beads (conjugated with a poly-T oligonucleotide), are introduced to the complexes, and allowed to bind for 15-30 minutes on ice. The magnetic beads (now bound to the primer via polyA::polyT hybridization) are washed with several wash buffers, prior to a final wash in 100 mM KOAc binding buffer. At this point, the beads may be stored in the 100 mM KOAc binding buffer for later magnetic loading of ZMWs, or active sequencing complexes may be eluted from the beads. Elution is performed by introducing a low salt elution buffer (~5 mM KOAc) and a short incubation at 30° C. The beads are discarded, and the supernatant fraction contains active sequencing complexes. The concentration of DNA can be measured in this eluate via a fluorimetric method such as PicoGreen dye binding.

Example 8

Stability of Isolated Polymerase-Nucleic Acid Complexes

Figure 16:
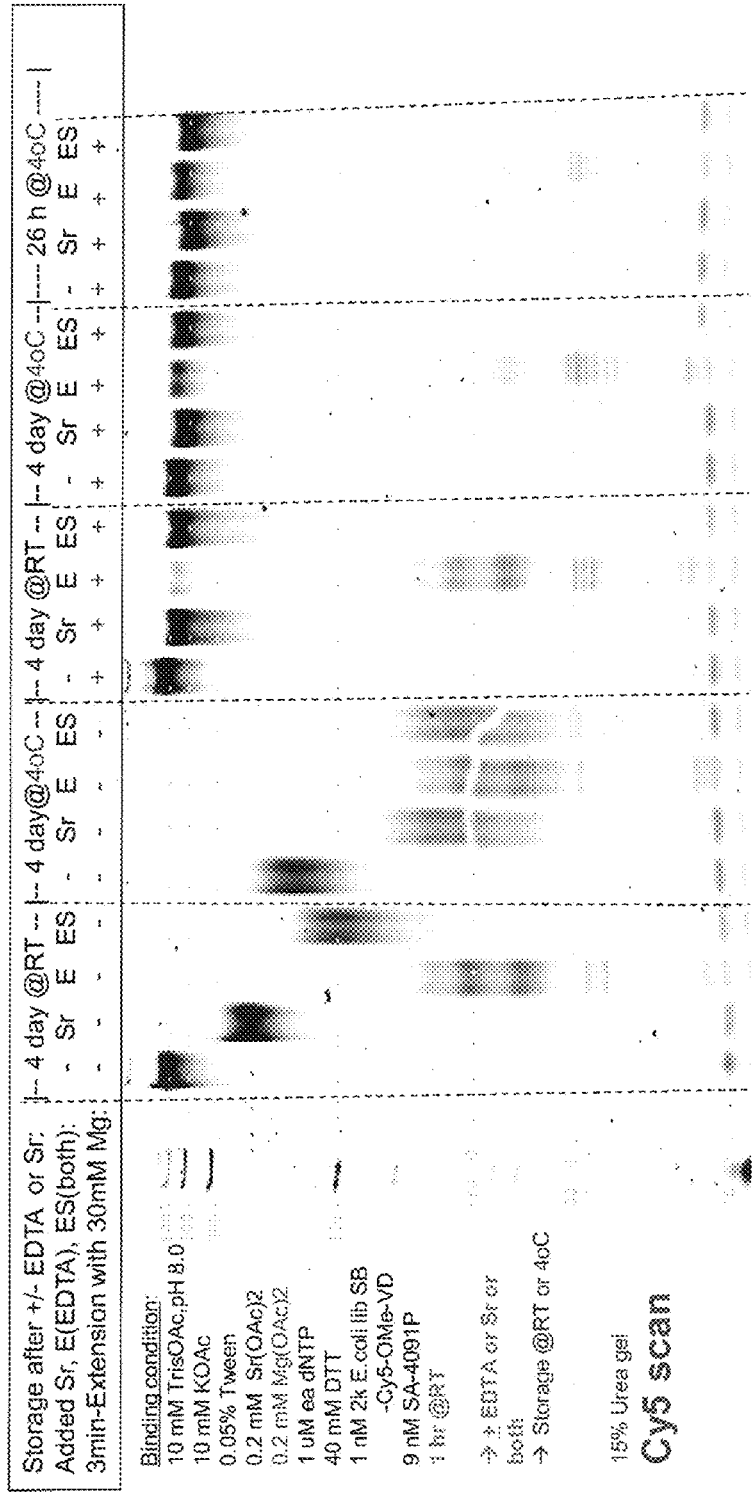
FIG. 16 shows the results of experiments showing that the reaction of polymerase nucleic acids can be halted, the complexes stored, then the reactions re-initiated.

A set of experiments was performed to determine the stability of isolated polymerase-nucleic acid complexes. A 2 Kb library of circular templates from $E.\ coli$ comprising double stranded regions flanked by hairpin adaptors at the ends was prepared. The templates were primed with primers that associate with the single stranded portion of the hairpin. The library was exposed to a Phi-29 type DNA polymerase enzyme under conditions to allow for primer extension. Primer extension was carried out for 1 hour at room temperature, then halted. The halting was done either with Sr++, EDTA, or a mixture of EDTA and Sr++. Gels were run to show the extent to which primer extension had occurred and been halted. After 4 days at room temperature and at 40° C., gels were run to measure the extent of crawling (continued primer extension) during that time. After this, the complexes were again exposed to conditions for primer extension including the addition of magnesium. Gels showed that in most cases, the complexes continued to extend, showing that the complexes were still active after storage. FIG. 16 shows the results of the stability experiment.

Example 9

Targeting Regions within the Double Stranded Portion of a Template

Figure 17:
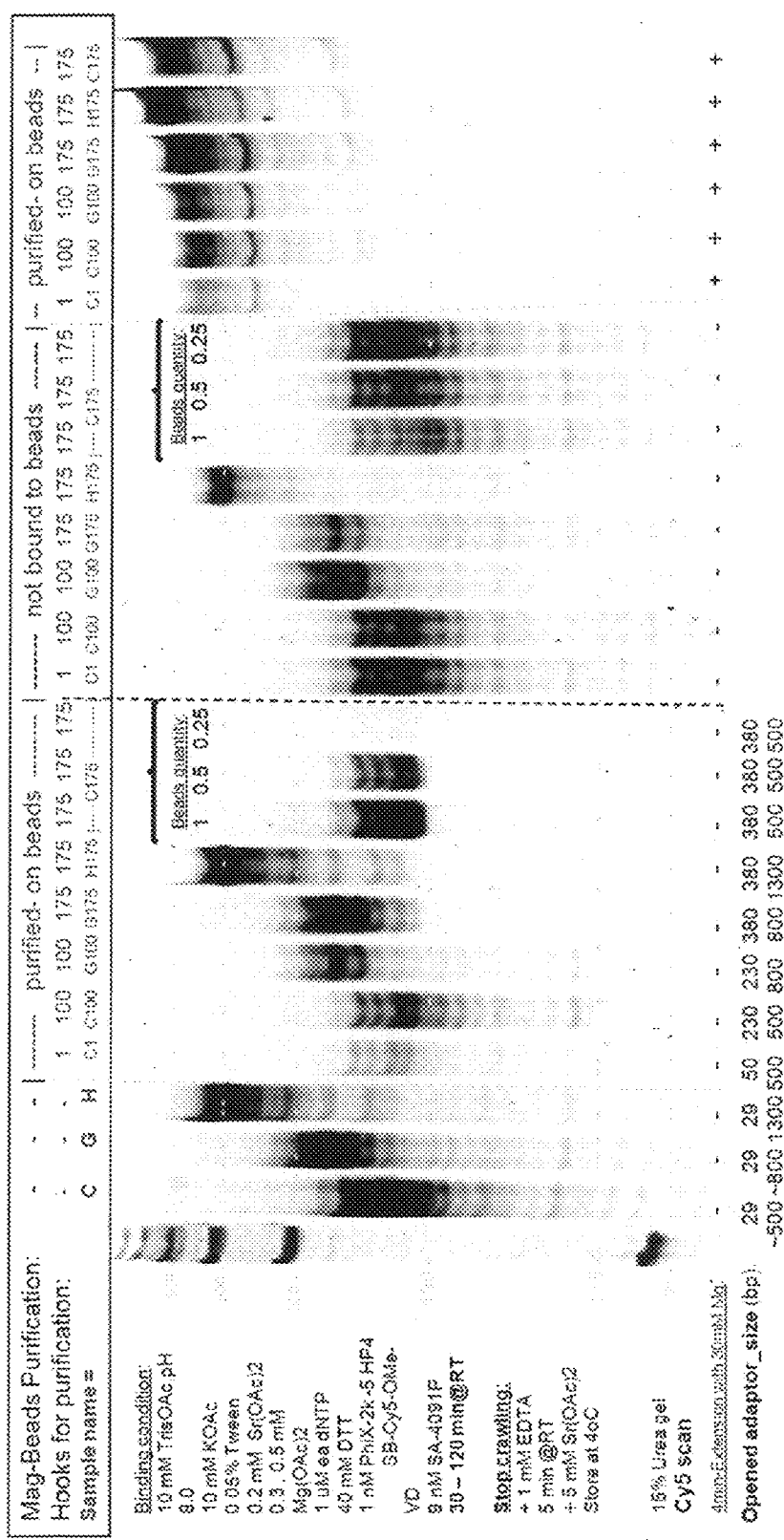
FIG. 17 shows the results of experiments showing how hooks can be used to enrich complexes having target-specific regions.

A double stranded template with a size of about 2 Kb having hairpin adaptors at each end was prepared. A series of hook oligomers was prepared which were complementary to different regions along the double stranded portion of the template. The hook oligomers targeted different portions of the double stranded region as depicted in FIGS. 5C and 5D. Hook oligomers had a 3' A(23) connected to a specific sequence of 13 to 15 bases that was complementary to a targeted region within the double stranded portion. The hook oligomers were designed to target a series of regions each extending a different number of bases from the primer site in the hairpin into the double stranded region. The series of hook oligomers was Hook-49, Hook-100, Hook-103, Hook-125, Hook-150, Hook-175, Hook-210, Hook-231, Hook-250, Hook-252, and Hook-317. For example, Hook-100 was a hook oligonucleotide with a 15 base specific capture region targeted to a portion about 100 bases into the double stranded region. A series of experiments were run in which a polymerase associated with the template was allowed to extend the primer to various extents by controlling the polymerase reaction conditions and the time. The hook oligomers were used to capture the polymerase-nucleic acid complexes that had extended deep enough into the double stranded region to expose the relevant sequence. The nucleic acid from the polymerase-nucleic acid complex was isolated and run onto a gel to characterize the molecular weight and the amount of product that was captured. The experiments demonstrated that hook oligonucleotides can be used to selectively capture specific regions of the template that are opened up by the polymerase by primer extension. FIG. 17 shows the results of a representative experiment.

Example 10

MagBead Complex Loading Versus Concentration

Figure 18:
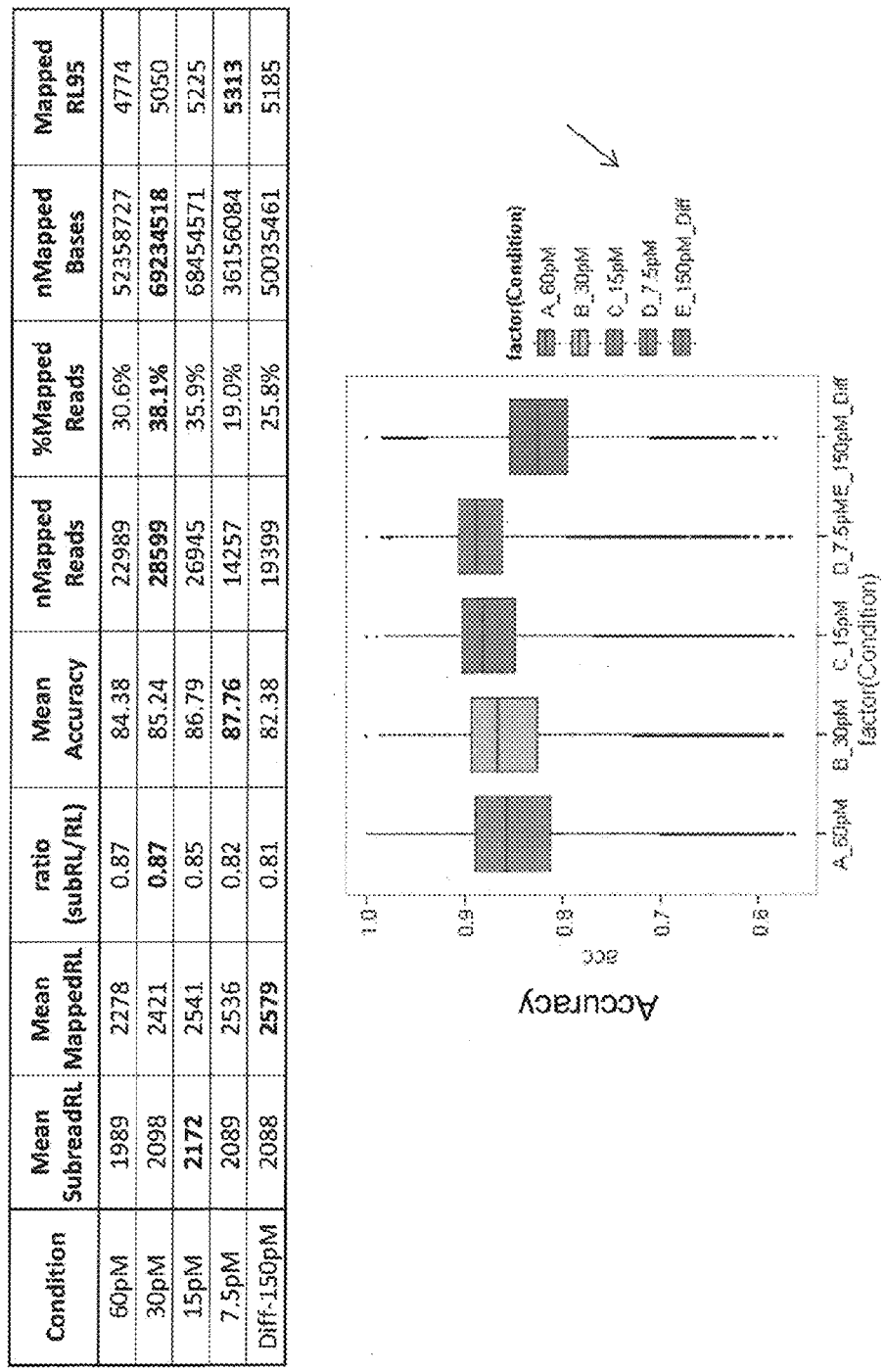
FIG. 18 shows experimental results of how magnetic bead loading can be used to load single polymerase-nucleic acid complexes into arrays of zero mode waveguides.

Polymerase-nucleic acid complexes made with 10 Kb templates SMRTbell templates and a phi-29 polymerase were attached to magnetic beads. A solution of the magnetic beads was dispensed onto a ZMW array chip, and a neodymium magnet was rotated below the chip to bring down the beads and move them with respect to the surface of the chip. This process was performed for 1 hour at four different concentrations of complex: 7.5 pM, 15 pM, 30 pM, and 60 pM. For comparison, chip loading by diffusion (no magnetic beads) was performed by exposing the chip to polymerase-nucleic acid complex in solution at 150 pM. Single-molecule sequencing was performed on the samples as described in Eid, J. et al., Science, 323(5910), 133-138 (2009)). FIG. 18 shows the sequencing results from the samples. The accuracy of the magnetic bead loaded samples was higher than that of the sample loaded by diffusion even though the diffusion sample was at a much higher concentration.

Example 11

Plasmid Digest Ladder

Figure 19:
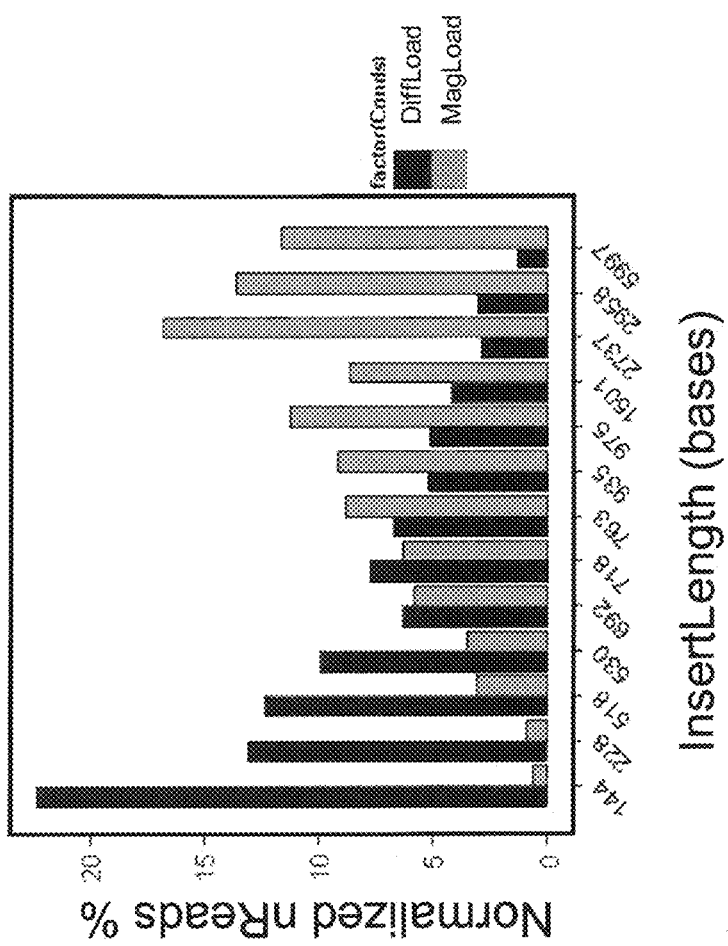
FIG. 19 are experimental result showing that magnetic bead loading results in a larger fraction of longer length templates into zero mode waveguides.

A plasmid was digested with restriction enzymes to generate a series of templates of various insert lengths. The templates were made into circular (SMRTbell™) templates by the ligation of hairpins onto the ends of the double stranded fragments. The templates were associated with a phi-29 polymerase, and a primer having a polyA tail was hybridized to the hairpin portion of the template. This sample was coupled to magnetic beads with polyT DNA attached. A solution of magnetic beads was dispensed onto a ZMW chip and a neodymium magnet below the chip was rotated to move the beads down and to move them with respect to the chip surface. Another sample of the polymerase-nucleic acid complex was loaded onto a ZMW chip by diffusion. The chips were used for single molecule sequencing as described in Eid, J. et al., Science, 323(5910), 133-138 (2009)). FIG. 19 shows the number of reads that was obtained as a function of the insert length. The data show that with diffusion loading there is a bias toward the smaller templates, whereas the samples loaded by magnetic bead demonstrated a higher loading of the larger templates than of the smaller templates. This data show how loading from beads can be extremely beneficial for measuring certain types of samples. In many cases, one desires to get the sequence of larger inserts, but if there is preferential loading of the small inserts, only a small fraction of the larger inserts are measured. Bead loading allows for efficient loading of these larger templates.

Example 12

Reduction of "Sticking" Pulses

Figure 20:
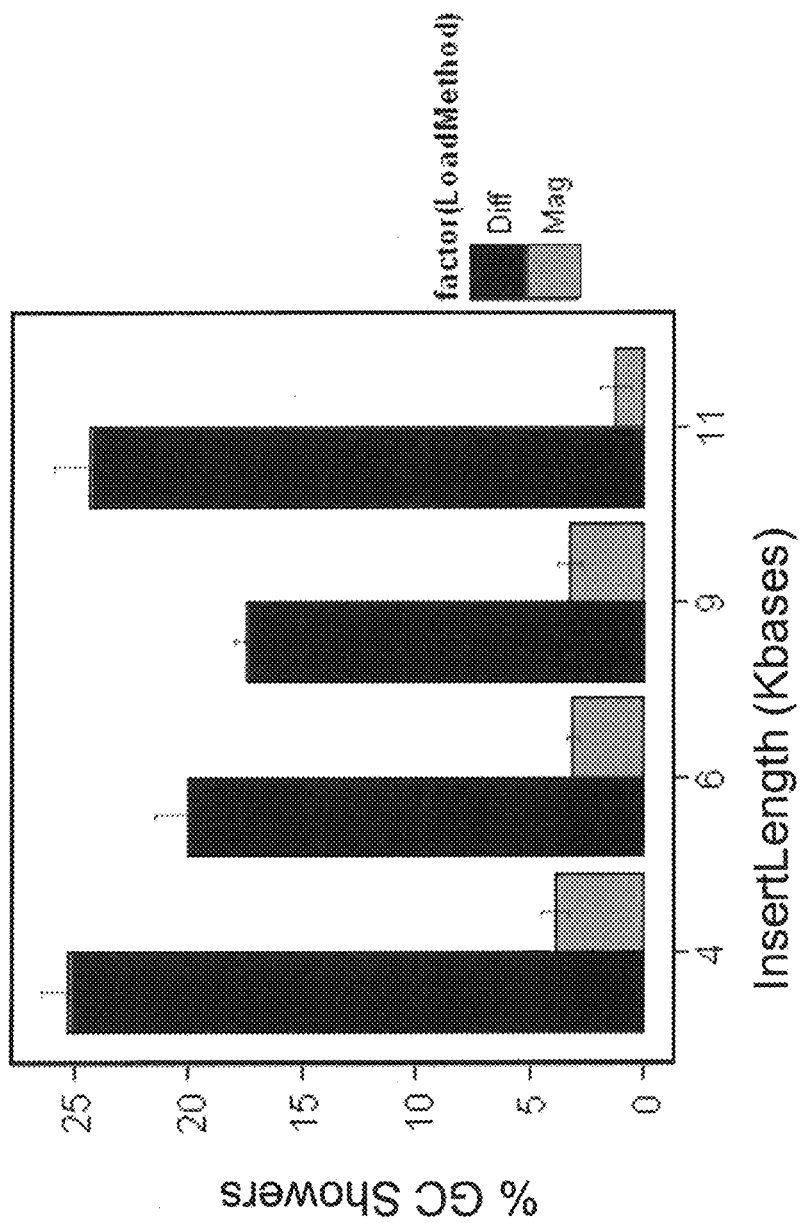
FIG. 20 shows single molecule sequencing results indicating lower levels of sticking from magnetic bead loaded complexes.

As described above, it is found that in some cases the samples loaded with magnetic beads show higher accuracy than comparable samples loaded by diffusion. FIG. 20 shows one reason why accuracy is better in the bead loaded samples. Here, the same samples are loaded by diffusion and by magnetic beads. FIG. 20 shows the percent of ZMWs that show GC showers. GC showers is a name for a phenomenon where a large number of non-sequencing peaks are detected. Another name for GC showers is "sticking" which can be caused by having fluorescently labeled nucleotide analogs stuck to the surface. We have found that the GC showers can be an indication of the presence of uncomplexed polymerase. The magnetic bead loaded samples can be rinsed free of excess polymerase prior to loading onto a chip, while it is difficult to remove such polymerases from a polymerase-nucleic acid complex solution produced for diffusion loading.

Example 13

Magnet Rotation and Chip Coverage

Figure 21:
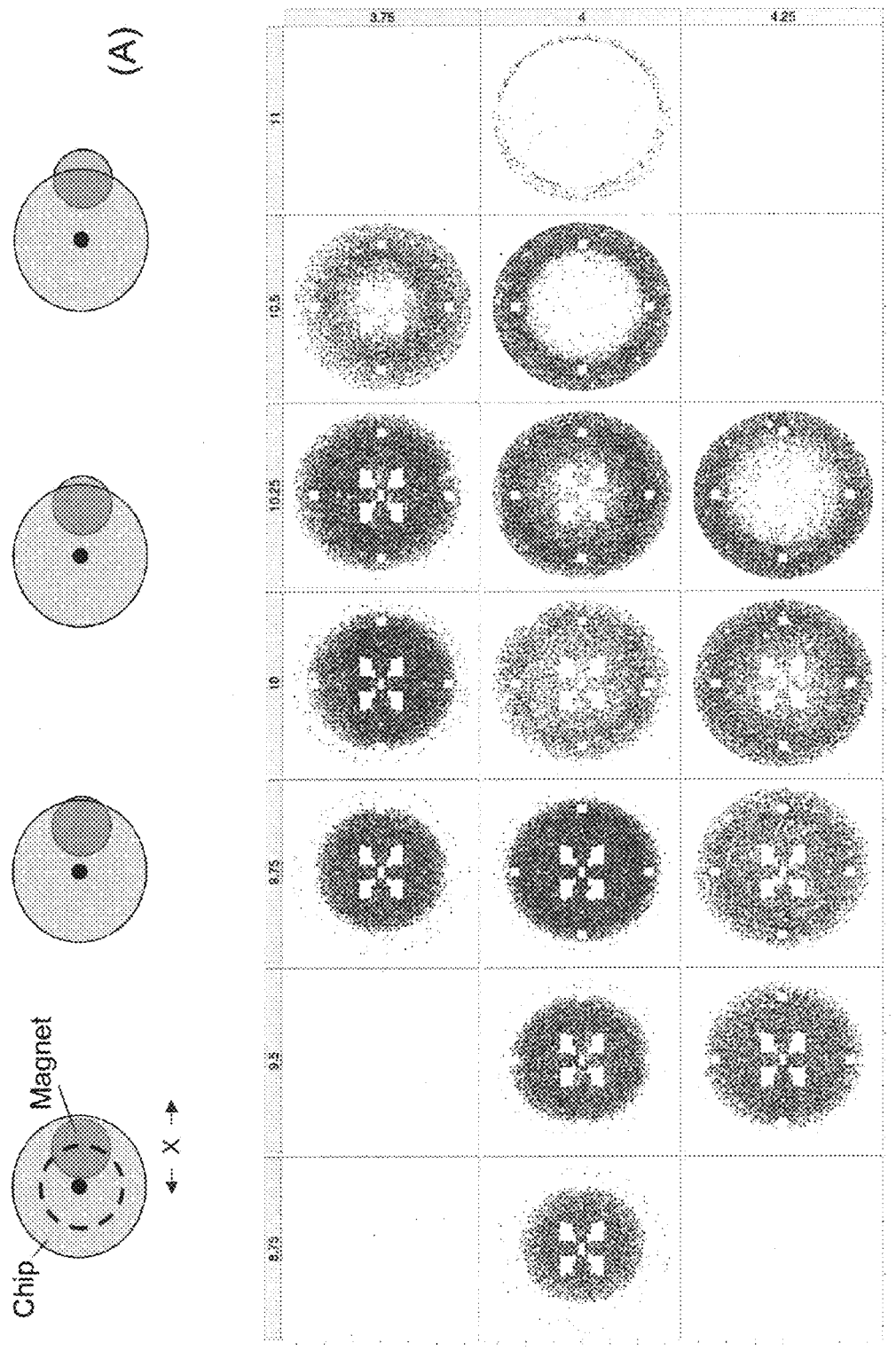
FIG. 21 shows the results of experiments in which the position of the magnet under the chip was varied in order to obtain broad and consistent loading of complexes across a ZMW chip.

FIG. 21(A) shows an illustration of how the magnet is moved relative to the chip in one embodiment. The is magnet underneath the chip and is rotated along the dotted line shown. The four representations in FIG. 21(A) illustrate how the magnet can be moved closer or farther away from the center along the x direction. An experiment was performed in which the position of the magnet along the radius (X shown in the figure) and the distance of the magnet below the chip (Y)

was varied. For various values of X and Y, the coverage across the chip was measured. FIG. 21(B) shows a measure of the loading across the chip as X and Y are varied (values in mm). It can be seen that by choosing the appropriate values a broad, relatively even coverage can be obtained.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. A method for isolating a polymerase-nucleic acid complex comprising:
    forming a polymerase-nucleic acid complex by mixing: (a) a polymerase enzyme comprising strand displacement activity, and (b) a nucleic acid comprising a double stranded portion comprising a first strand and a complementary second strand;
    initiating nucleic acid synthesis by the polymerase enzyme to produce a nascent strand complementary to the first strand, thereby displacing a portion of the second strand;
    halting or reducing the rate of nucleic acid synthesis;
    hybridizing a hook oligonucleotide to the complex through a capture region on the hook oligonucleotide that is complementary to at least some of the displaced portion of the second strand; and
    isolating the complex using the hook oligonucleotide.

2. The method of claim 1 further comprising loading the isolated complex onto a substrate.

3. The method of claim 2 further comprising carrying out single-molecule nucleic acid sequencing with the polymerase-nucleic acid complex on the substrate.

4. The method of claim 1 wherein the laic acid is a circular nucleic acid.

5. The method of claim 4 wherein the nucleic acid comprises a double stranded central region and single stranded hairpin end regions.

6. The method of claim 1 wherein the nucleic acid comprises a linear nucleic acid comprising a linear double-stranded adaptor.

7. The method of claim 1 wherein the hook oligonucleotide also has a retrieval region having a sequence that allows the hook oligonucleotide to be bound and retrieved from a reaction mixture.

8. The method of claim 7 wherein the retrieval region is complementary to a sequence attached to beads, and the beads are used for the isolation of the nucleic acid.

9. The method of claim 8 wherein the beads are magnetic beads.

10. The method of claim 8 wherein the retrieval region comprises poly(A), poly(dA), poly(T) or poly(dT).

11. The method of claim 1 wherein the hook oligonucleotide comprises a member of a binding pair providing for isolation of the complex comprising the hook oligonucleotide bound to the nucleic acid.

12. The method of claim 11 wherein the binding pair comprises biotin, digoxigenin, a protein, or an antibody.

13. The method of claim 1 wherein halting or rate reduction comprises adding a limiting amount of polymerase synthesis reagents.

14. The method of claim 13 wherein the limiting reagents comprise nucleotides or nucleotide analogs.

15. The method of claim 1 wherein halting or rate reduction comprises adding reagents to stop the polymerization reaction after a time.

16. A method comprising;
    fragmenting a double stranded DNA sample into double stranded fragments;
    ligating to each end of the double stranded fragments a hairpin to produce a population of circular DNA templates having a central double stranded region and hairpin regions on each end;
    exposing the population of circular DNA templates to a primer complementary to the single stranded portion of a hairpin region of the template and to a DNA polymerase enzyme having strand displacement activity under conditions in which a population of polymerase-template-primer complexes are formed;
    initiating polymerase mediated DNA synthesis to extend the primer, whereby the primer is extended into the double stranded region, displacing the portion of the double strand,
    halting or reducing the rate of synthesis of DNA;
    adding to the population of complexes a hook oligonucleotide comprising a capture region complementary to a displaced portion of the double strand under conditions under which hybridization between the hook oligonucleotide and the DNA templates occurs;
    using the hook oligonucleotide to isolate the complexes to which it hybridized;
    thereby isolating complexes having active polymerase enzyme from complexes that are not active.

17. The method of claim 16 wherein the hook oligonucleotide also has a retrieval region having a sequence that allows the hook oligonucleotide to be bound and retrieved from a reaction mixture.

18. The method of claim 17 wherein the retrieval region is complementary to a sequence attached to beads, and the beads are used for the isolation of the nucleic acid.

19. A method for DNA sequencing comprising isolating active complexes by the method of claim 16, loading the active complexes onto a substrate such that single complexes can be individually optically resolved comprising;
    exposing the active complexes to a plurality of differentially labeled nucleotide analogs whose labels are cleaved upon incorporation, and
    initiating DNA synthesis and observing each complex to determine the time sequence of nucleotides that are incorporated.

* * * * *

```
                              SEQUENCE LISTING

<160> NUMBER OF SEQ ID NOS: 12

<210> SEQ ID NO 1
<211> LENGTH: 44
<212> TYPE: DNA
<213> ORGANISM: Artificial Sequence
<220> FEATURE:
<223> OTHER INFORMATION: synthetic

<400> SEQUENCE: 1
tctctctctt ttcctcctcc tccgttgttg ttgttgagag agat              44

<210> SEQ ID NO 2
<211> LENGTH: 36
<212> TYPE: DNA
<213> ORGANISM: Artificial Sequence
<220> FEATURE:
<223> OTHER INFORMATION: synthetic

<400> SEQUENCE: 2
tctctctcaa caaaaaaaaa aaaaaaaaaa aaaaaa                       36

<210> SEQ ID NO 3
<211> LENGTH: 37
<212> TYPE: DNA
<213> ORGANISM: Artificial Sequence
<220> FEATURE:
<223> OTHER INFORMATION: synthetic

<400> SEQUENCE: 3
aatgcttact caagaaaaaa aaaaaaaaaa aaaaaaa                      37

<210> SEQ ID NO 4
<211> LENGTH: 37
<212> TYPE: DNA
<213> ORGANISM: Artificial Sequence
<220> FEATURE:
<223> OTHER INFORMATION: synthetic

<400> SEQUENCE: 4
atgaagtaat cacgaaaaaa aaaaaaaaaa aaaaaaa                      37

<210> SEQ ID NO 5
<211> LENGTH: 15
<212> TYPE: DNA
<213> ORGANISM: Artificial Sequence
<220> FEATURE:
<223> OTHER INFORMATION: synthetic

<400> SEQUENCE: 5
caacggagga ggagg                                              15

<210> SEQ ID NO 6
<211> LENGTH: 22
<212> TYPE: DNA
```

```
<213> ORGANISM: Artificial Sequence
<220> FEATURE:
<223> OTHER INFORMATION: synthetic

<400> SEQUENCE: 6
ggaccacctc ctgagagaga ga                                              22

<210> SEQ ID NO 7
<211> LENGTH: 46
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (21)..(30)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 7
tctctctctc aggaggtggt nnnnnnnnnn cctcctcctc cgttgn                    46

<210> SEQ ID NO 8
<211> LENGTH: 35
<212> TYPE: DNA
<213> ORGANISM: Artificial Sequence
<220> FEATURE:
<223> OTHER INFORMATION: synthetic

<400> SEQUENCE: 8
aggaggtggt ccaaaaaaaa aaaaaaaaaa aaaaa                                35

<210> SEQ ID NO 9
<211> LENGTH: 13
<212> TYPE: DNA
<213> ORGANISM: Artificial Sequence
<220> FEATURE:
<223> OTHER INFORMATION: synthetic

<400> SEQUENCE: 9
tctctctcaa caa                                                        13

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
aaaaaaaaaa aaaaaaaaaa                                                 20

<210> SEQ ID NO 11
<211> LENGTH: 15
<212> TYPE: DNA
<213> ORGANISM: Artificial Sequence
<220> FEATURE:
<223> OTHER INFORMATION: synthetic

<400> SEQUENCE: 11
aaaaaaaaaa aaaaa                                                      15

<210> SEQ ID NO 12
<211> LENGTH: 44
<212> TYPE: DNA
```

```
<213> ORGANISM: Artificial Sequence
<220> FEATURE:
<223> OTHER INFORMATION: synthetic

<400> SEQUENCE: 12
tctctctctt ttcctcctcc tccgttgttg ttgttgagag agat            44
```